(12) United States Patent
Self et al.

(10) Patent No.: US 8,703,492 B2
(45) Date of Patent: *Apr. 22, 2014

(54) OPEN PLATFORM HYBRID MANUAL-AUTOMATED SAMPLE PROCESSING SYSTEM

(75) Inventors: Brian Austin Self, Germantown, MD (US); Jonathan Matthew Miller, Burke, VA (US); Carl Theodore Edens, Highland, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 954 days.

This patent is subject to a terminal disclaimer.

(21) Appl. No.: 12/588,306

(22) Filed: Oct. 9, 2009

(65) Prior Publication Data
US 2010/0126286 A1    May 27, 2010

Related U.S. Application Data

(63) Continuation-in-part of application No. 12/062,950, filed on Apr. 8, 2008, now Pat. No. 7,985,375.

(60) Provisional application No. 60/910,565, filed on Apr. 6, 2007, provisional application No. 61/183,857, filed on Jun. 3, 2009, provisional application No. 61/113,855, filed on Nov. 12, 2008, provisional application No. 61/122,621, filed on Dec. 15, 2008, provisional application No. 61/185,081, filed on Jun. 8, 2009, provisional application No. 61/242,671, filed on Sep. 15, 2009.

(51) Int. Cl.
| G01N 35/02 | (2006.01) |
| G01N 1/18  | (2006.01) |
| G01N 1/10  | (2006.01) |
| G01N 21/31 | (2006.01) |

(52) U.S. Cl.
USPC ............... 436/47; 422/63; 422/65; 422/67; 436/43; 436/48; 436/174; 436/175; 436/176; 436/177; 436/178; 436/180

(58) Field of Classification Search
USPC ............ 436/47–50, 174–180, 43; 422/63–67
See application file for complete search history.

(56) References Cited

U.S. PATENT DOCUMENTS

| 2,360,978 A | 10/1944 | Putter |
| 2,979,210 A | 4/1961 | Patterson |

(Continued)

FOREIGN PATENT DOCUMENTS

| JP | 2184762 | 7/1990 |
| WO | WO2006/054964 | 5/2006 |

(Continued)

OTHER PUBLICATIONS

Curt Malloy, et al., "HPV DNA Testing: Technical and Programmatic Issues for Cervical Cancer Prevention in Low-Resource Settings," Alliance for Cervical Prevention; Dec. 2000, 27 pages.

*Primary Examiner* — Arlen Soderquist
(74) *Attorney, Agent, or Firm* — RatnerPrestia

(57) ABSTRACT

An automated sample processing system having a sample input adapted to simultaneously receive a number of sample containers, a reagent input adapted to receive one or more new reagent supplies, a consumable input adapted to receive one or more new consumable supplies, a solid waste output adapted to receive used consumable supplies, a liquid waste output adapted to receive one or more used reagent supplies, and a processing center. The processing center includes a decapper adapted to remove a lid from at least one sample container, an aspirator adapted to remove a specimen from the at least one sample container and transfer the specimen to an output vessel, and a capper adapted to replace the lid on the at least one sample container. The system also includes a sample output adapted to receive the output vessel, and a user interface adapted to receive an input from the user to indicate the identity of the at least one sample container, and control at least one operation based on a physical property of the at least one sample container.

25 Claims, 39 Drawing Sheets

(56) References Cited

U.S. PATENT DOCUMENTS

| | | | |
|---|---|---|---|
| 3,375,934 A | 4/1968 | Bates | |
| 3,379,315 A | 4/1968 | Broadwin | |
| 3,491,894 A | 1/1970 | Brown | |
| 3,589,103 A * | 6/1971 | Calvillo et al. | 53/381.4 |
| 3,744,665 A | 7/1973 | Spoto | |
| 3,905,482 A | 9/1975 | Knulst | |
| 3,918,920 A | 11/1975 | Barber | |
| 4,000,976 A * | 1/1977 | Kramer et al. | 422/65 |
| 4,039,286 A | 8/1977 | Keller et al. | |
| 4,068,798 A * | 1/1978 | Rohde | 494/20 |
| 4,096,965 A | 6/1978 | Lessnig et al. | |
| 4,124,122 A | 11/1978 | Emmitt | |
| 4,151,950 A | 5/1979 | Gunnewig | |
| 4,217,798 A * | 8/1980 | McCarthy et al. | 81/3.2 |
| 4,224,278 A * | 9/1980 | Hogen Esch | 422/65 |
| 4,283,950 A | 8/1981 | Tervamaki | |
| 4,338,279 A * | 7/1982 | Orimo et al. | 422/64 |
| 4,368,913 A | 1/1983 | Brockmann et al. | |
| 4,406,547 A * | 9/1983 | Aihara | 356/414 |
| 4,478,095 A | 10/1984 | Bradley et al. | |
| 4,482,522 A | 11/1984 | Baudisch et al. | |
| 4,483,927 A * | 11/1984 | Takekawa | 436/43 |
| 4,517,160 A | 5/1985 | Galle et al. | 422/65 |
| 4,534,465 A | 8/1985 | Rothermel et al. | |
| 4,535,585 A * | 8/1985 | Gardos | 53/247 |
| 4,544,193 A | 10/1985 | Dunn et al. | |
| 4,545,723 A | 10/1985 | Clark | |
| 4,609,017 A | 9/1986 | Coulter et al. | |
| 4,632,631 A | 12/1986 | Dunlap | |
| 4,692,308 A | 9/1987 | Riley et al. | |
| 4,696,144 A | 9/1987 | Bankuty et al. | |
| 4,740,025 A | 4/1988 | Nelson | |
| 4,766,082 A * | 8/1988 | Marteau D'Autry | 436/178 |
| 4,794,085 A | 12/1988 | Jassop et al. | |
| 4,798,095 A * | 1/1989 | Itoh | 73/863.01 |
| 4,805,772 A | 2/1989 | Shaw et al. | |
| 4,855,110 A | 8/1989 | Marker et al. | |
| 4,856,073 A * | 8/1989 | Farber et al. | 382/128 |
| 4,861,553 A * | 8/1989 | Mawhirt et al. | 422/65 |
| 4,876,926 A * | 10/1989 | Muszak | 81/3.2 |
| 4,938,369 A | 7/1990 | Carilli | |
| 4,968,077 A | 11/1990 | Redmon et al. | |
| 4,970,053 A | 11/1990 | Fechtner | |
| 4,974,460 A | 12/1990 | Baxter | |
| 4,982,553 A * | 1/1991 | Itoh | 53/246 |
| 5,008,081 A | 4/1991 | Blau et al. | |
| 5,008,082 A * | 4/1991 | Shaw | 422/65 |
| 5,013,529 A * | 5/1991 | Itoh | 422/511 |
| 5,063,790 A | 11/1991 | Freeman et al. | |
| 5,075,082 A | 12/1991 | Fechtner | |
| 5,080,232 A | 1/1992 | Leoncavallo et al. | |
| 5,080,864 A * | 1/1992 | Shaw | 422/62 |
| 5,087,423 A * | 2/1992 | Ishibashi | 422/67 |
| 5,116,578 A | 5/1992 | Baxter | |
| 5,137,693 A | 8/1992 | Mawhirt | |
| 5,174,762 A | 12/1992 | Hoppal et al. | |
| 5,202,262 A | 4/1993 | Lemonnier | |
| 5,203,236 A | 4/1993 | Anderson | |
| 5,232,665 A * | 8/1993 | Burkovich et al. | 422/65 |
| 5,255,574 A * | 10/1993 | Wuerschum | 81/3.2 |
| 5,270,210 A | 12/1993 | Weyrauch et al. | |
| 5,271,897 A * | 12/1993 | Wurschum et al. | 422/63 |
| 5,313,858 A | 5/1994 | Stitt | |
| 5,332,549 A | 7/1994 | MacIndoe, Jr. | |
| 5,340,544 A * | 8/1994 | Nishikawa et al. | 422/500 |
| 5,341,854 A | 8/1994 | Zazulka et al. | |
| 5,366,896 A * | 11/1994 | Margrey et al. | 436/48 |
| 5,374,395 A | 12/1994 | Robinson et al. | |
| 5,389,339 A * | 2/1995 | Petschek et al. | 422/64 |
| 5,397,542 A | 3/1995 | Nelms et al. | |
| 5,417,922 A | 5/1995 | Markin et al. | |
| 5,437,838 A | 8/1995 | DeMoranville et al. | |
| 5,445,037 A * | 8/1995 | Itoh | 73/864.25 |
| 5,456,887 A | 10/1995 | Calvo et al. | |
| 5,463,895 A | 11/1995 | Brantz | |
| 5,472,669 A * | 12/1995 | Miki et al. | 422/63 |
| 5,479,969 A | 1/1996 | Hardie et al. | |
| 5,481,946 A | 1/1996 | Nishikawa et al. | |
| 5,490,321 A * | 2/1996 | Kaneko | 29/714 |
| 5,491,067 A | 2/1996 | Setcavage et al. | |
| 5,493,849 A * | 2/1996 | Itoh | 53/489 |
| 5,499,545 A | 3/1996 | Kimura et al. | |
| 5,503,036 A | 4/1996 | Nguyen et al. | |
| 5,525,298 A | 6/1996 | Anami | |
| 5,536,056 A | 7/1996 | Clarke et al. | |
| 5,537,880 A | 7/1996 | Takeda et al. | |
| 5,540,081 A | 7/1996 | Takeda et al. | |
| 5,540,890 A | 7/1996 | Clark et al. | |
| 5,550,059 A | 8/1996 | Bogar et al. | |
| 5,551,828 A | 9/1996 | Iles | |
| 5,578,494 A | 11/1996 | Clark et al. | |
| 5,579,929 A | 12/1996 | Schwartz | |
| 5,585,068 A * | 12/1996 | Panetz et al. | 422/64 |
| 5,589,137 A | 12/1996 | Markin et al. | |
| 5,604,101 A | 2/1997 | Hanlay et al. | |
| 5,627,522 A | 5/1997 | Walker et al. | |
| 5,637,275 A | 6/1997 | Carey et al. | |
| 5,639,599 A * | 6/1997 | Ryder et al. | 435/5 |
| 5,646,049 A * | 7/1997 | Tayi | 436/518 |
| 5,651,941 A | 7/1997 | Stark et al. | |
| 5,652,568 A | 7/1997 | Ko | |
| 5,658,532 A | 8/1997 | Kurosaki et al. | |
| 5,675,715 A | 10/1997 | Bernstein et al. | |
| 5,687,849 A | 11/1997 | Borenstein et al. | |
| 5,700,429 A | 12/1997 | Buhler et al. | |
| 5,721,384 A | 2/1998 | Tanihata | |
| 5,723,289 A | 3/1998 | Eaton et al. | |
| 5,730,276 A * | 3/1998 | Itoh | 198/465.1 |
| 5,736,102 A | 4/1998 | Seaton et al. | |
| 5,737,498 A * | 4/1998 | Murray | 700/246 |
| 5,753,186 A | 5/1998 | Hanley et al. | |
| 5,772,962 A * | 6/1998 | Uchida et al. | 422/67 |
| 5,775,755 A | 7/1998 | Covert et al. | |
| 5,778,740 A | 7/1998 | Tya | |
| 5,814,276 A * | 9/1998 | Riggs | 422/65 |
| 5,819,508 A * | 10/1998 | Kraft et al. | 53/492 |
| 5,851,042 A | 12/1998 | Bankuty et al. | |
| 5,861,563 A | 1/1999 | Boyd et al. | |
| 5,872,361 A | 2/1999 | Paoli et al. | |
| 5,876,670 A | 3/1999 | Mitsumaki et al. | |
| 5,882,596 A * | 3/1999 | Breeser et al. | 422/65 |
| 5,897,835 A | 4/1999 | Seaton et al. | |
| 5,915,282 A | 6/1999 | Merriam et al. | |
| 5,919,706 A | 7/1999 | Tajima | |
| 5,928,952 A | 7/1999 | Hutchins et al. | |
| 5,948,360 A | 9/1999 | Rao et al. | |
| 5,965,828 A | 10/1999 | Merriam | |
| 5,966,309 A | 10/1999 | O'Bryan et al. | |
| 5,985,219 A | 11/1999 | Lind | |
| 5,985,672 A | 11/1999 | Kegelman et al. | |
| 5,988,857 A | 11/1999 | Ozawa et al. | |
| 5,996,818 A | 12/1999 | Boje et al. | |
| 6,022,747 A | 2/2000 | Gherson et al. | |
| 6,060,022 A | 5/2000 | Pang et al. | |
| 6,060,320 A | 5/2000 | Dorenkott et al. | |
| 6,065,617 A | 5/2000 | Cohen et al. | |
| 6,071,477 A | 6/2000 | Auclair et al. | |
| 6,076,330 A | 6/2000 | Thomas et al. | |
| 6,100,094 A | 8/2000 | Tajima | |
| 6,105,343 A | 8/2000 | Grove et al. | |
| 6,111,238 A | 8/2000 | Fix, Sr. et al. | |
| 6,117,398 A | 9/2000 | Bienhaus et al. | |
| 6,121,049 A | 9/2000 | Dorenkott et al. | |
| 6,123,205 A | 9/2000 | Dumitrescu et al. | |
| 6,126,903 A | 10/2000 | Preston et al. | |
| 6,141,602 A * | 10/2000 | Igarashi et al. | 700/226 |
| 6,142,039 A | 11/2000 | Herring, Sr. | |
| 6,156,275 A | 12/2000 | Dumitrescu et al. | |
| 6,161,759 A | 12/2000 | Moss et al. | |
| 6,170,232 B1 | 1/2001 | VandaGaijn | |
| 6,190,619 B1 * | 2/2001 | Kilcoin et al. | 506/33 |
| 6,202,278 B1 * | 3/2001 | Nakayama et al. | 29/426.3 |
| 6,203,760 B1 | 3/2001 | Van Der Plaats et al. | |
| 6,216,340 B1 | 4/2001 | Fassbind et al. | |

(56) References Cited

U.S. PATENT DOCUMENTS

| | | | |
|---|---|---|---|
| 6,227,053 B1 | 5/2001 | Purpura et al. | |
| 6,232,464 B1* | 5/2001 | Lange | 536/25.4 |
| 6,257,091 B1 | 7/2001 | Cohen et al. | |
| 6,274,092 B1 | 8/2001 | Itoh | |
| 6,290,907 B1* | 9/2001 | Takahashi et al. | 422/65 |
| 6,293,750 B1 | 9/2001 | Cohen et al. | |
| 6,299,840 B1* | 10/2001 | Watanabe et al. | 422/63 |
| 6,321,619 B1* | 11/2001 | Itoh | 81/3.2 |
| 6,326,147 B1 | 12/2001 | Oldham et al. | |
| 6,331,437 B1* | 12/2001 | Cohen et al. | 436/43 |
| 6,332,636 B1 | 12/2001 | Cohen et al. | |
| 6,335,166 B1 | 1/2002 | Ammann et al. | |
| 6,347,552 B1 | 2/2002 | Purpura et al. | |
| 6,358,474 B1 | 3/2002 | Doblar et al. | |
| 6,370,942 B1 | 4/2002 | Dunfee et al. | |
| 6,415,669 B1 | 7/2002 | Carl | |
| 6,417,008 B2 | 7/2002 | Tyberg et al. | |
| 6,426,228 B1 | 7/2002 | Cohen et al. | |
| 6,432,365 B1* | 8/2002 | Levin et al. | 422/509 |
| 6,435,582 B1 | 8/2002 | DaSilva et al. | |
| 6,436,349 B1 | 8/2002 | Carey et al. | |
| 6,444,472 B1 | 9/2002 | Cohen et al. | |
| 6,449,827 B1* | 9/2002 | Clarke et al. | 29/559 |
| 6,458,324 B1 | 10/2002 | Schinzel | |
| 6,484,556 B1 | 11/2002 | Jabobs et al. | |
| 6,498,037 B1 | 12/2002 | Carey et al. | |
| 6,499,364 B1 | 12/2002 | Suovaniemi | |
| 6,521,183 B1 | 2/2003 | Burri et al. | |
| 6,531,096 B1* | 3/2003 | Deveney et al. | 422/65 |
| 6,553,824 B1 | 4/2003 | Lutze | |
| 6,558,628 B1* | 5/2003 | Reo | 422/569 |
| 6,562,299 B1 | 5/2003 | Ostgaard et al. | |
| 6,562,568 B1 | 5/2003 | Kleiber et al. | |
| 6,565,809 B1* | 5/2003 | Itoh | 422/67 |
| 6,572,824 B1* | 6/2003 | Ostgaard et al. | 422/67 |
| 6,573,088 B2 | 6/2003 | Gemmell et al. | |
| 6,576,477 B1 | 6/2003 | Tokiwa et al. | |
| 6,581,647 B1 | 6/2003 | Leidlein et al. | |
| 6,598,474 B2 | 7/2003 | Purpura et al. | |
| 6,599,476 B1* | 7/2003 | Watson et al. | 422/63 |
| 6,604,337 B2 | 8/2003 | Close et al. | |
| 6,604,903 B2 | 8/2003 | Osborne et al. | |
| 6,605,213 B1 | 8/2003 | Ammann et al. | |
| 6,620,585 B1 | 9/2003 | Zyskind | |
| 6,622,578 B2 | 9/2003 | Carl | |
| 6,651,305 B2* | 11/2003 | Fassbind et al. | 29/426.1 |
| 6,656,724 B1* | 12/2003 | Heimberg et al. | 435/286.4 |
| 6,669,910 B1* | 12/2003 | Bienhaus et al. | 422/547 |
| 6,689,318 B1 | 2/2004 | Spork et al. | |
| 6,691,748 B1 | 2/2004 | Tajima | |
| 6,721,615 B2* | 4/2004 | Fava et al. | 700/99 |
| 6,723,289 B2 | 4/2004 | Iheme et al. | |
| 6,730,517 B1* | 5/2004 | Koster et al. | 436/47 |
| 6,734,424 B2 | 5/2004 | Lennon et al. | |
| 6,743,398 B2* | 6/2004 | Itoh | 422/73 |
| 6,764,649 B2 | 7/2004 | Ammann | |
| 6,772,650 B2* | 8/2004 | Biwa et al. | 73/864.24 |
| 6,773,927 B2 | 8/2004 | Osawa et al. | |
| 6,793,887 B2* | 9/2004 | Itoh | 422/63 |
| 6,805,294 B2* | 10/2004 | Itoh | 235/462.01 |
| 6,810,757 B2 | 11/2004 | Carl | |
| 6,829,954 B2* | 12/2004 | Katagi | 73/864.25 |
| 6,838,051 B2 | 1/2005 | Marquiss et al. | |
| 6,843,357 B2 | 1/2005 | Bybee et al. | |
| 6,849,236 B2* | 2/2005 | Spitz et al. | 422/62 |
| 6,852,283 B2 | 2/2005 | Acosta et al. | |
| 6,864,100 B1* | 3/2005 | Ribbe et al. | 436/178 |
| 6,871,566 B2* | 3/2005 | Niwayama et al. | 81/3.2 |
| 6,887,432 B2 | 5/2005 | Kansy et al. | |
| 6,890,742 B2 | 5/2005 | Ammann et al. | |
| 6,919,044 B1 | 7/2005 | Shibata et al. | |
| 6,919,175 B1 | 7/2005 | Bienhaus et al. | |
| 6,926,058 B2* | 8/2005 | Sato et al. | 156/556 |
| 6,932,942 B2 | 8/2005 | Itoh | |
| 6,938,504 B2 | 9/2005 | Camenisch | |
| 6,943,181 B2 | 9/2005 | Sundermann et al. | |
| 6,956,055 B2 | 10/2005 | Sundermann et al. | |
| 6,959,952 B2 | 11/2005 | Williams | |
| 6,978,689 B2 | 12/2005 | Carl | |
| 6,984,527 B2* | 1/2006 | Miller | 436/180 |
| 6,985,828 B2* | 1/2006 | Itoh | 702/173 |
| 6,998,094 B2* | 2/2006 | Haslam et al. | 422/65 |
| 7,000,785 B2 | 2/2006 | Jafari et al. | |
| 7,078,698 B2* | 7/2006 | Itoh | 250/357.1 |
| 7,087,607 B2 | 8/2006 | Gerlach et al. | |
| 7,117,902 B2 | 10/2006 | Osborne | |
| 7,118,892 B2 | 10/2006 | Ammann et al. | |
| 7,141,213 B1* | 11/2006 | Pang et al. | 422/65 |
| 7,150,190 B2 | 12/2006 | Krufka et al. | |
| 7,152,504 B2* | 12/2006 | Itoh | 81/3.2 |
| 7,152,736 B1 | 12/2006 | Menichini | |
| 7,159,489 B2* | 1/2007 | Itoh | 81/3.2 |
| 7,207,241 B2* | 4/2007 | Itoh | 81/3.2 |
| 7,220,385 B2* | 5/2007 | Blecka et al. | 422/64 |
| 7,227,622 B2* | 6/2007 | Itoh | 356/39 |
| 7,233,838 B2 | 6/2007 | Barry et al. | |
| 7,251,921 B2 | 8/2007 | Galimberti et al. | |
| 7,282,182 B2 | 10/2007 | Dale et al. | |
| 7,284,900 B2 | 10/2007 | Mayer | |
| 7,287,792 B2 | 10/2007 | Tye | |
| 7,322,170 B2 | 1/2008 | Tomalesky et al. | |
| 7,340,324 B2* | 3/2008 | Heath et al. | 700/266 |
| 7,377,027 B2 | 5/2008 | Mayer | |
| 7,409,809 B1* | 8/2008 | Degen et al. | 53/381.4 |
| 7,416,706 B2 | 8/2008 | Brunner et al. | |
| 7,421,831 B2* | 9/2008 | Neeper et al. | 53/381.4 |
| 7,425,305 B2* | 9/2008 | Itoh | 422/65 |
| 7,435,387 B2 | 10/2008 | Itoh | |
| 7,477,997 B2 | 1/2009 | Kaplit | |
| 7,501,094 B2 | 3/2009 | Bysouth et al. | |
| 7,514,042 B2 | 4/2009 | Lihl et al. | |
| 7,537,735 B2 | 5/2009 | Hiemer et al. | |
| 7,556,777 B2* | 7/2009 | Victor | 422/560 |
| 7,572,638 B2 | 8/2009 | Pressman et al. | |
| 7,575,937 B2 | 8/2009 | Wiggli et al. | |
| 7,579,190 B2* | 8/2009 | Ostgaard et al. | 436/43 |
| 7,581,660 B2 | 9/2009 | Nay et al. | |
| 7,597,846 B2 | 10/2009 | Walter et al. | |
| 7,610,115 B2 | 10/2009 | Rob et al. | |
| 7,634,378 B2 | 12/2009 | Kaplit | |
| 7,635,246 B2* | 12/2009 | Neeper et al. | 414/280 |
| 7,681,466 B2 | 3/2010 | Miller et al. | |
| 7,694,591 B2 | 4/2010 | Leibfried | |
| 7,783,383 B2 | 8/2010 | Eliuk et al. | |
| 7,792,647 B1 | 9/2010 | Ding et al. | |
| 7,846,384 B2 | 12/2010 | Watson et al. | |
| 7,858,033 B2* | 12/2010 | Itoh | 422/65 |
| 7,985,375 B2* | 7/2011 | Edens et al. | 422/64 |
| 8,099,928 B2 | 1/2012 | Yuyama | |
| 2002/0001542 A1* | 1/2002 | Itoh | 422/64 |
| 2002/0025064 A1* | 2/2002 | Itoh | 382/134 |
| 2002/0041828 A1* | 4/2002 | Spitz et al. | 422/64 |
| 2002/0086431 A1 | 7/2002 | Markham et al. | |
| 2002/0090320 A1 | 7/2002 | Burow et al. | |
| 2002/0125230 A1 | 9/2002 | Haight et al. | |
| 2002/0164269 A1 | 11/2002 | Ngo et al. | |
| 2002/0186363 A1 | 12/2002 | Samsoondar et al. | |
| 2003/0061911 A1* | 4/2003 | Niwayama et al. | 81/3.2 |
| 2003/0069699 A1 | 4/2003 | Ekins et al. | |
| 2003/0092186 A1* | 5/2003 | Pressman et al. | 436/46 |
| 2003/0213313 A1 | 11/2003 | Katagi | 73/864.25 |
| 2003/0215362 A1* | 11/2003 | Sato et al. | 422/63 |
| 2004/0022682 A1* | 2/2004 | Itoh | 422/64 |
| 2004/0029135 A1 | 2/2004 | Ramberg | |
| 2004/0076546 A1 | 4/2004 | Bissett | |
| 2004/0171168 A1* | 9/2004 | Itoh | 436/174 |
| 2004/0184958 A1* | 9/2004 | Itoh | 422/72 |
| 2004/0184959 A1* | 9/2004 | Itoh | 422/72 |
| 2004/0209374 A1 | 10/2004 | Kopf-Sill et al. | |
| 2005/0037502 A1* | 2/2005 | Miller | 436/43 |
| 2005/0047966 A1* | 3/2005 | Itoh | 422/99 |
| 2005/0069913 A1 | 3/2005 | Mian et al. | |
| 2005/0158212 A1* | 7/2005 | Yavilevich | 422/100 |
| 2005/0252342 A1* | 11/2005 | Itoh | 81/3.2 |

(56) References Cited

U.S. PATENT DOCUMENTS

| | | |
|---|---|---|
| 2006/0115889 A1 | 6/2006 | Nakashima et al. |
| 2006/0136095 A1 | 6/2006 | Rob et al. |
| 2006/0210432 A1* | 9/2006 | Victor ............................. 422/63 |
| 2007/0000352 A1* | 1/2007 | Itoh ................................. 81/3.2 |
| 2007/0006550 A1 | 1/2007 | Kemper et al. |
| 2007/0020764 A1 | 1/2007 | Miller |
| 2007/0059209 A1* | 3/2007 | Pang et al. ....................... 422/72 |
| 2007/0095024 A1* | 5/2007 | Neeper et al. ................... 53/485 |
| 2007/0172396 A1* | 7/2007 | Neeper et al. .................. 422/104 |
| 2007/0254277 A1* | 11/2007 | Scrabeck et al. .................. 435/4 |
| 2008/0019878 A1 | 1/2008 | Trump |
| 2008/0022808 A1 | 1/2008 | Owen et al. |
| 2008/0038827 A1 | 2/2008 | Miller et al. |
| 2008/0069730 A1* | 3/2008 | Itoh ................................. 422/65 |
| 2008/0090288 A1 | 4/2008 | Hibino et al. |
| 2008/0160539 A1 | 7/2008 | Murphy et al. |
| 2008/0160599 A1 | 7/2008 | Weber-Matthiesen et al. |
| 2008/0170967 A1* | 7/2008 | Itoh ............................... 422/104 |
| 2008/0247914 A1 | 10/2008 | Edens et al. |
| 2009/0003981 A1 | 1/2009 | Miller |
| 2009/0028754 A1 | 1/2009 | Robb |
| 2009/0068062 A1 | 3/2009 | Jafari et al. |
| 2009/0098022 A1 | 4/2009 | Tokhtuev et al. |
| 2009/0117620 A1 | 5/2009 | Fritchie et al. |
| 2009/0266149 A1 | 10/2009 | Kaplit |
| 2009/0305392 A1* | 12/2009 | Alfredsson et al. ........ 435/286.1 |
| 2009/0318276 A1 | 12/2009 | Miller |
| 2010/0015007 A1 | 1/2010 | Pedrazzini |
| 2010/0105060 A1 | 4/2010 | Eder et al. |
| 2010/0159463 A1 | 6/2010 | Eder et al. |
| 2010/0215548 A1 | 8/2010 | De Luca et al. |
| 2010/0241270 A1 | 9/2010 | Eliuk et al. |

FOREIGN PATENT DOCUMENTS

| | | | |
|---|---|---|---|
| WO | WO2006/081612 | | 8/2006 |
| WO | WO 2007/048042 | | 4/2007 |
| WO | WO 2008/123882 | * | 10/2008 |
| WO | WO2009/068555 | | 6/2009 |
| WO | WO2010/038852 | | 4/2010 |
| WO | WO2010/057861 | | 5/2010 |
| WO | WO2010056884 | | 5/2010 |
| WO | WO2010056890 | | 5/2010 |
| WO | WO2010056903 | | 5/2010 |
| WO | WO2010141040 | | 9/2010 |
| WO | WO2011063139 | | 5/2011 |

* cited by examiner

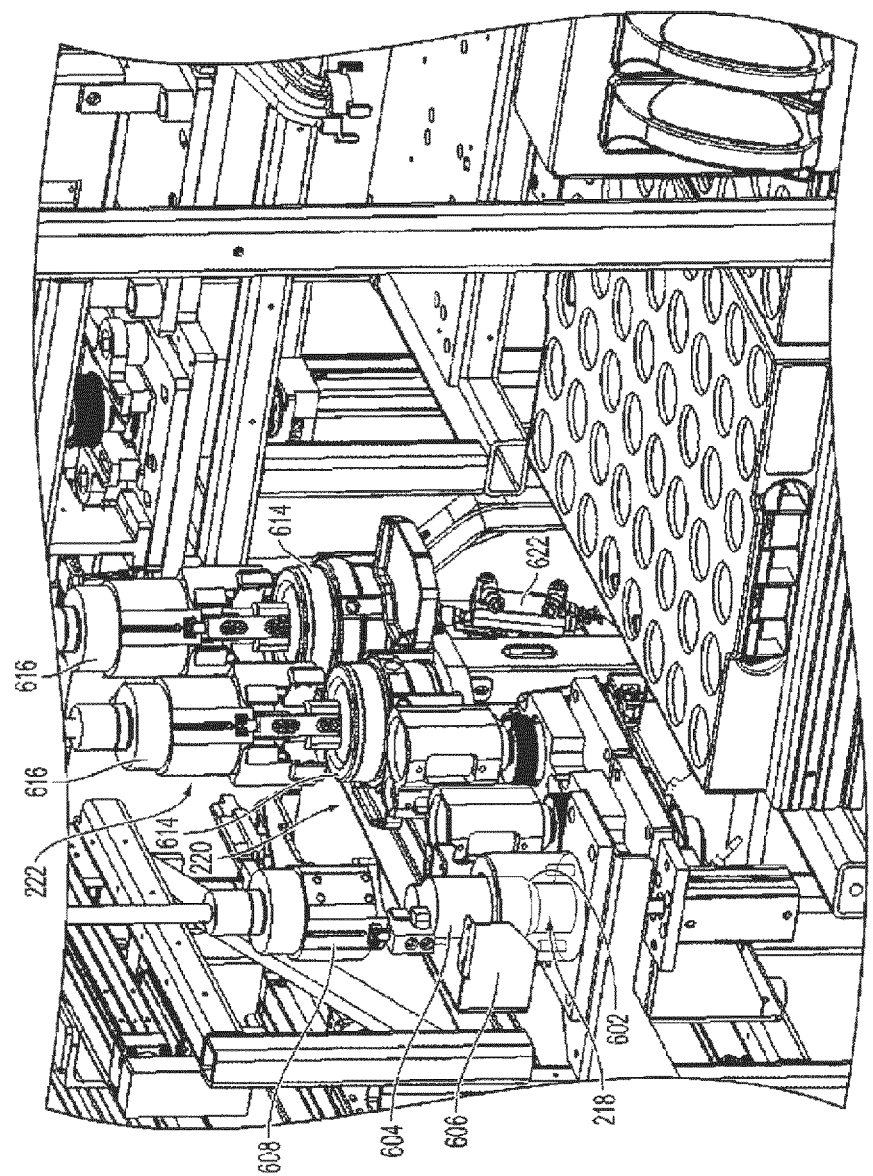

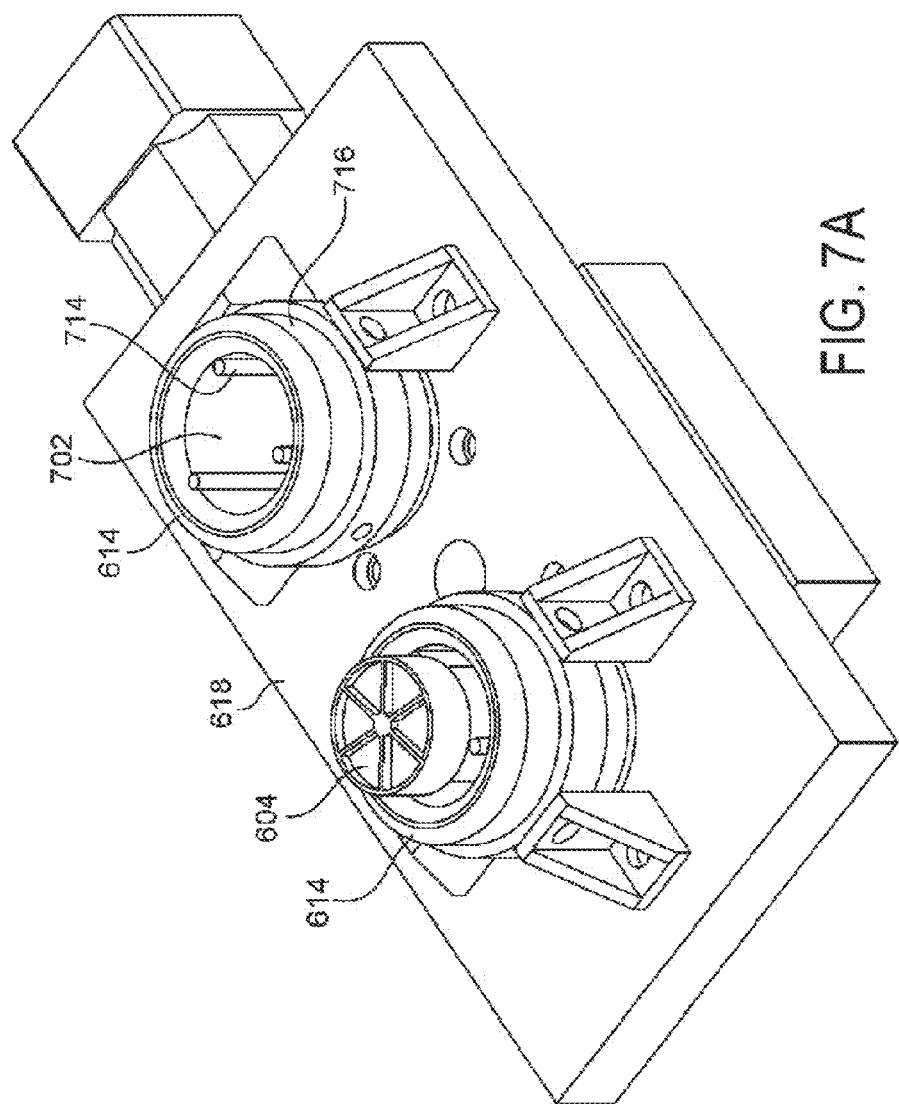

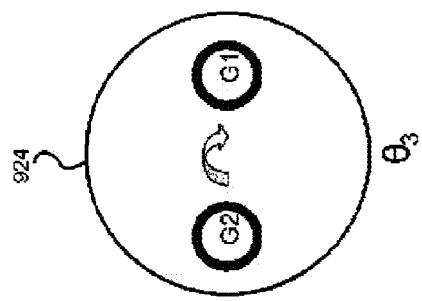
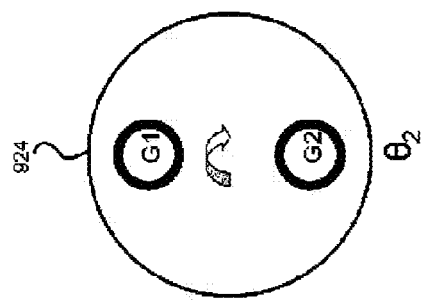
Fig. 9B
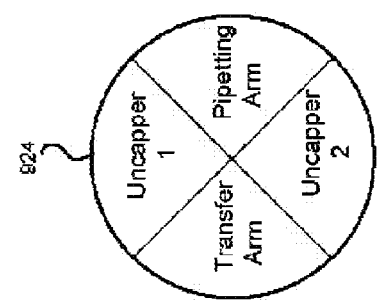
Fig. 9C
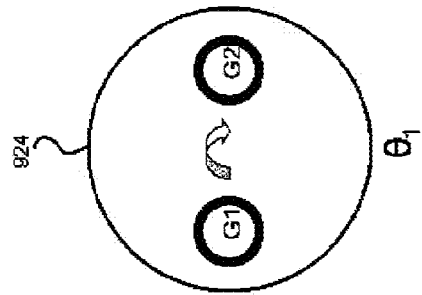

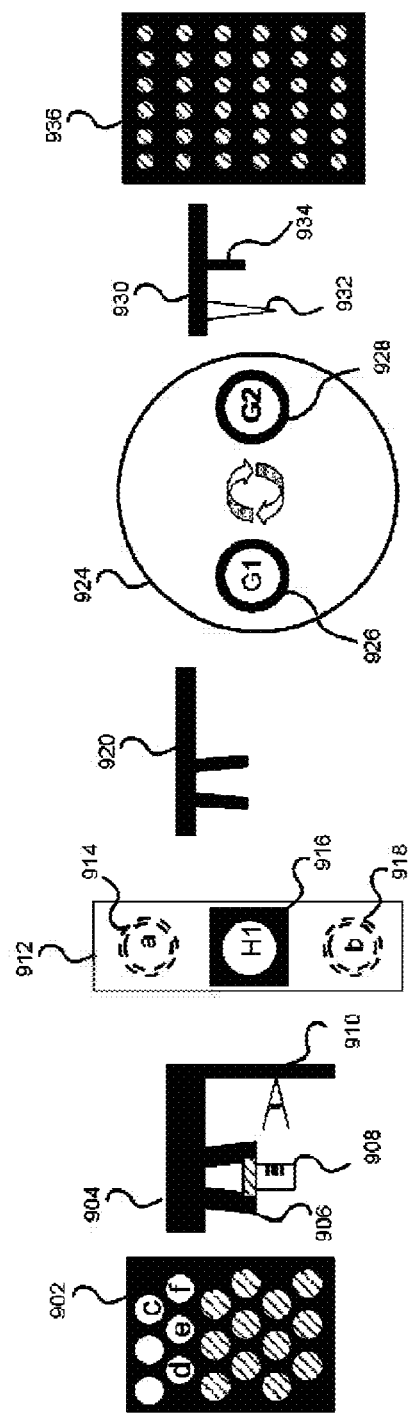

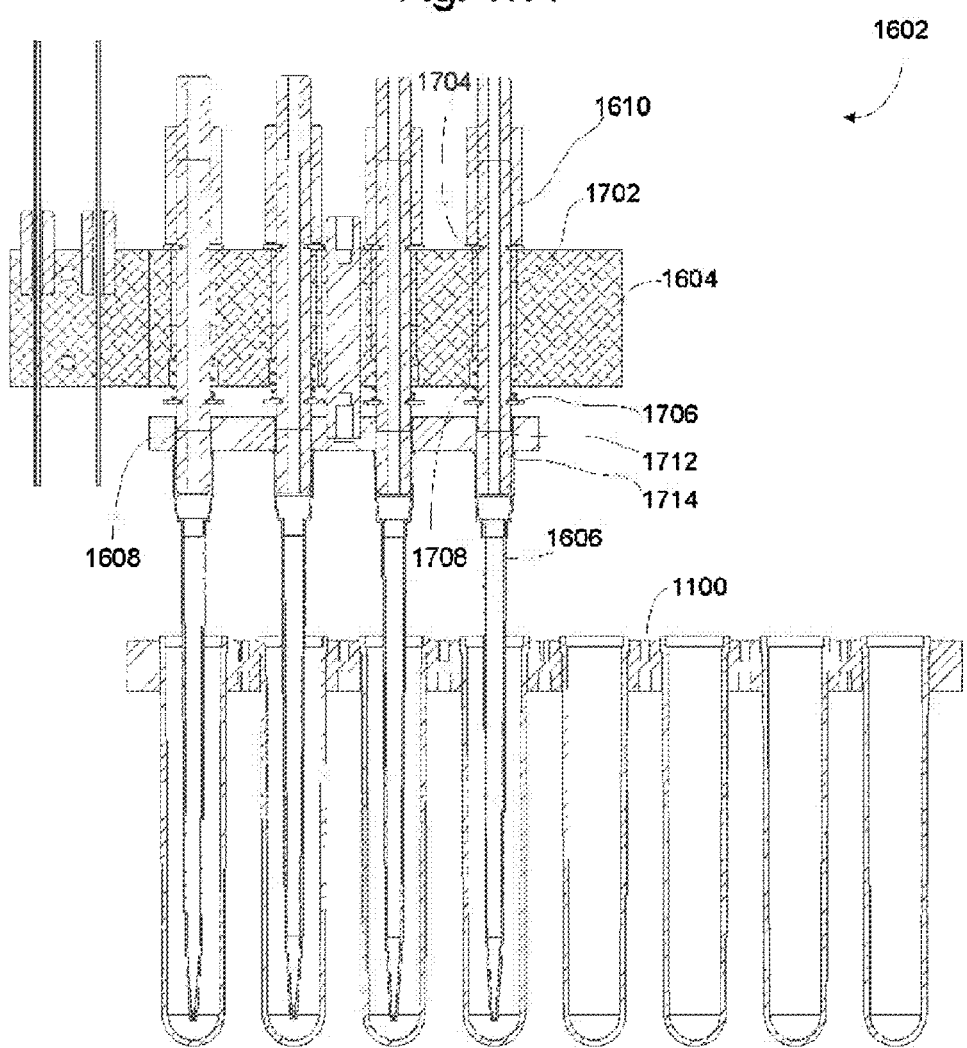

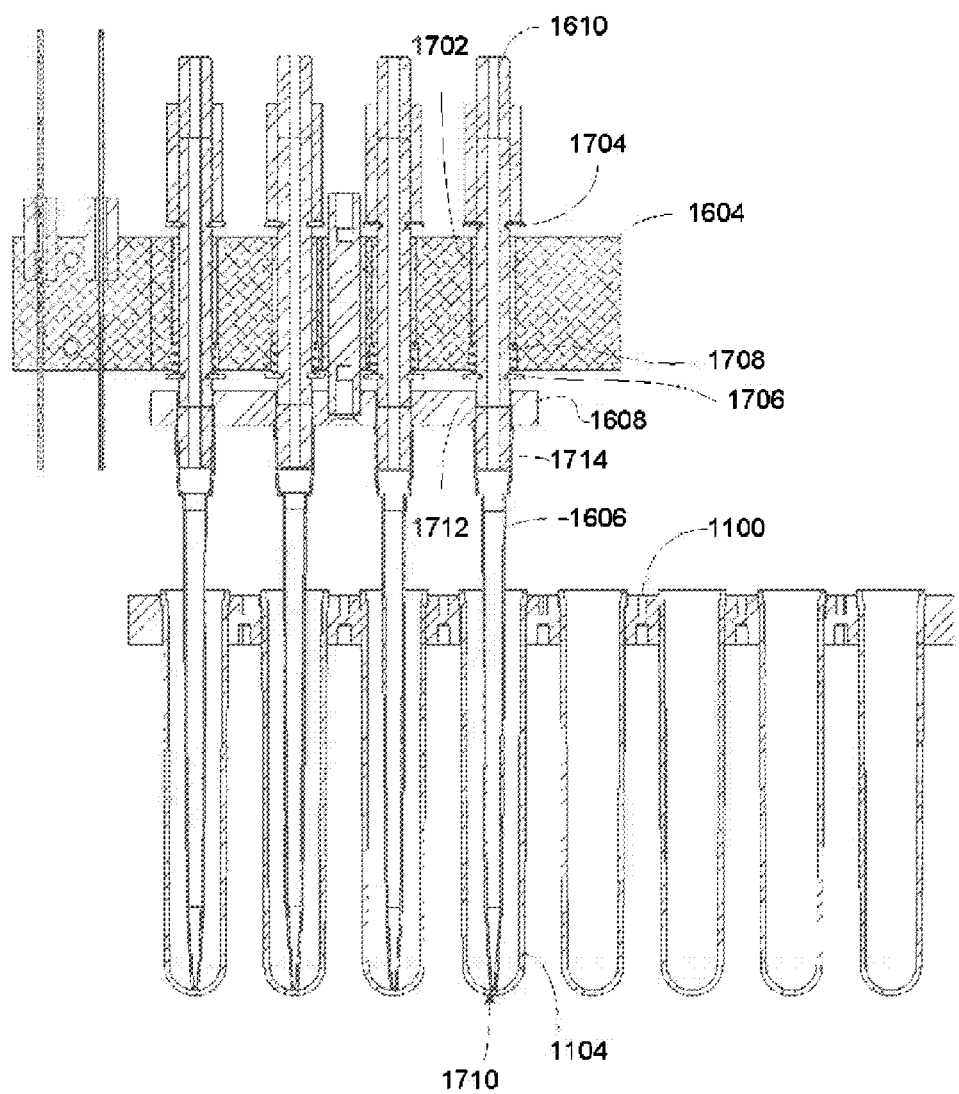

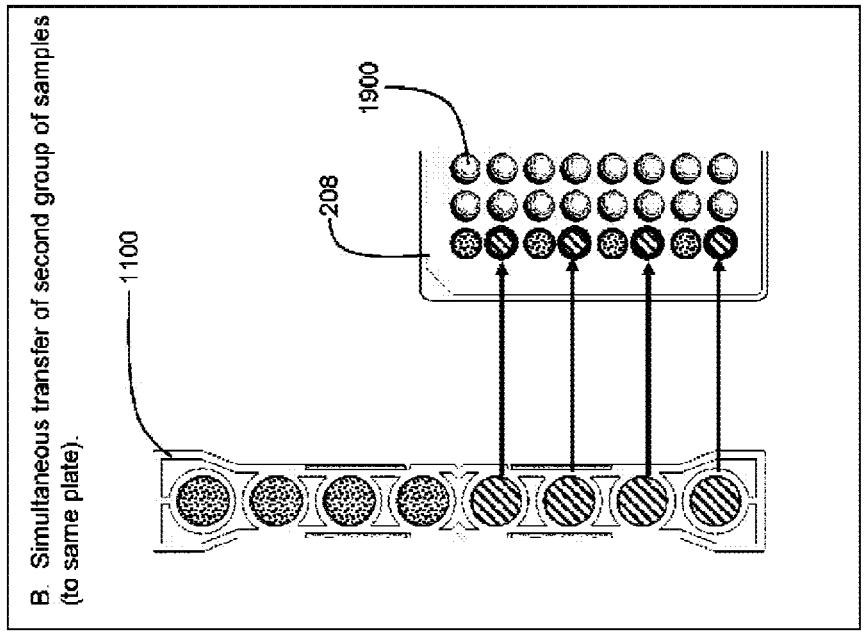
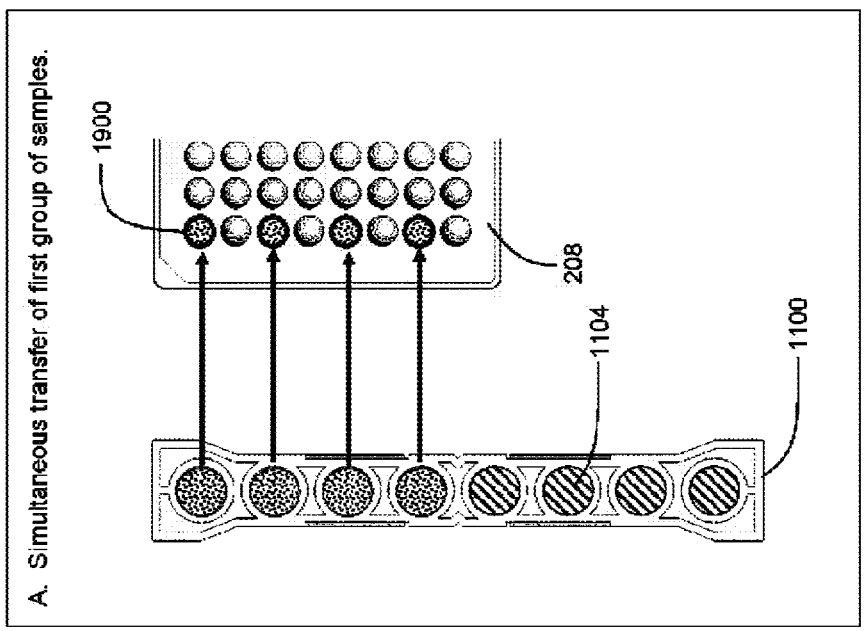

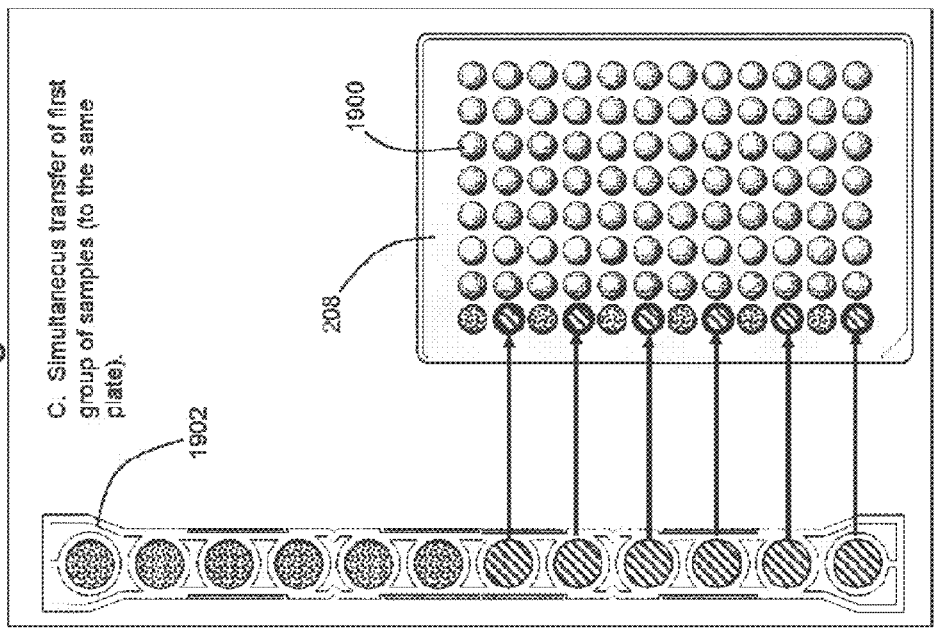
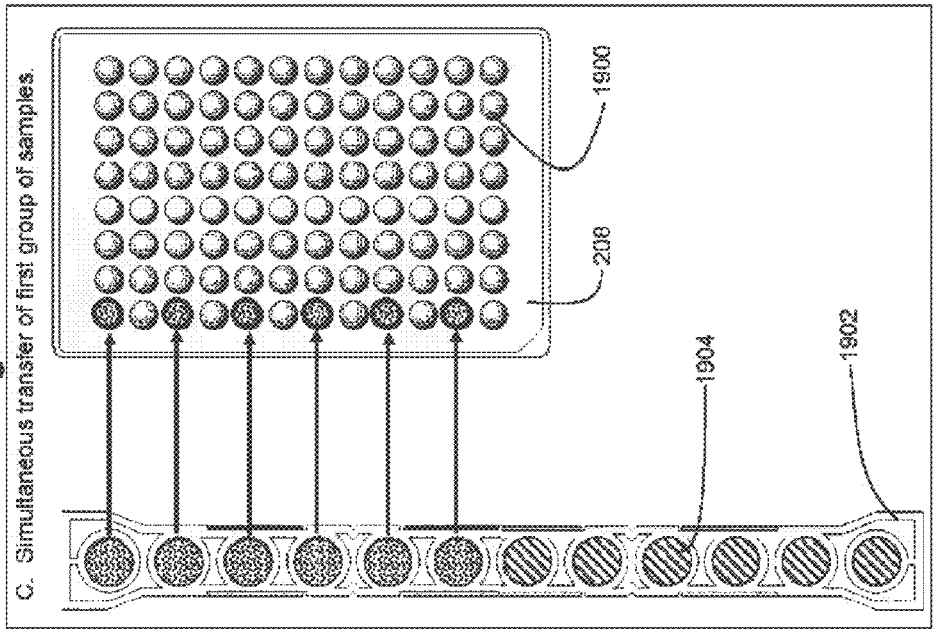

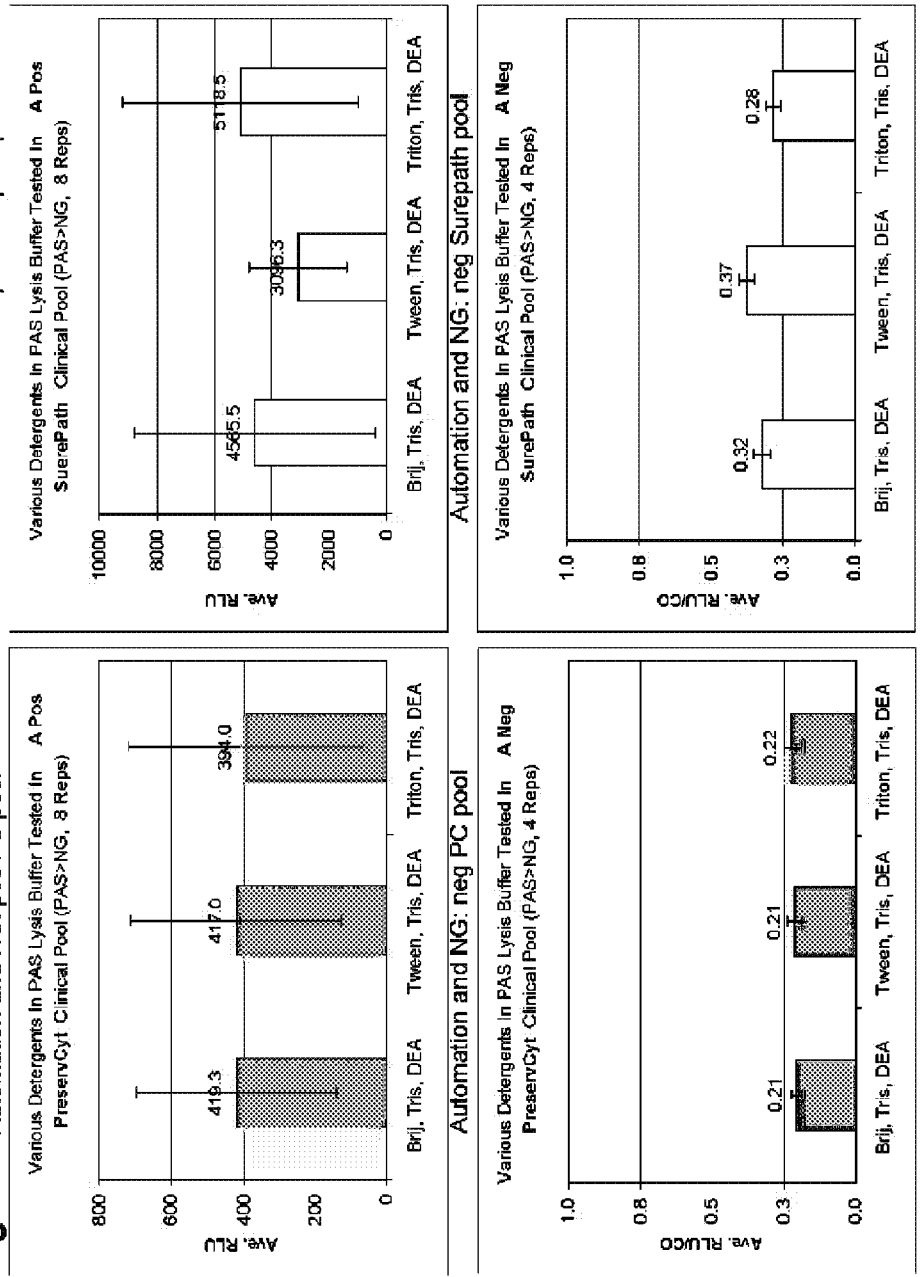
Fig. 24 Automation and NG: pos PC pool

Fig. 25 Assay agreement in total of 150 SurePath specimens, automated processing>Manual NG versus hc2

Before genotyping

|  | HC2 + | HC2 - |
|---|---|---|
| PAS>NG+ | 33 | 0 | 41 |
| PAS>NG- | 4 | 115 | 119 |
|  | 37 | 123 | 160 |

|  | Lower | Upper |
|---|---|---|
| Pos agreement % | 89.189% | (75.291% | 95.715%) |
| Negative agreement % | 93.496% | (87.690% | 96.668%) |
| total agreement % | 92.500% | (87.349% | 95.658%) |
| kappa =0.797 | | | |

Adjudicated after genotyping

|  | HC2 + | HC2 - | Indeterminate |
|---|---|---|---|
| PAS>NG+ | 33 | 7 | 1 |
| PAS>NG- | 1 | 115 | 3 |
|  | 37 | 123 | |

|  | Lower | Upper |
|---|---|---|
| Pos agreement % | 97.059% | (85.08% | 99.479%) |
| Negative agreement % | 94.262% | (88.629% | 97.193%) |
| total agreement % | 94.872% | (90.208% | 97.379%) |
| kappa =0.859 | | | |

OPEN PLATFORM HYBRID MANUAL-AUTOMATED SAMPLE PROCESSING SYSTEM

CROSS-REFERENCE TO RELATED APPLICATIONS

This application is a continuation-in-part of U.S. patent application Ser. No. 12/062,950, filed Apr. 4, 2008, now U.S. Pat. No. 7,985,375, which claims the benefit of U.S. Provisional Patent Application Ser. No. 60/910,565 filed Apr. 6, 2007. This application is also related to U.S. Provisional Patent Application Ser. No. 61/183,857, filed Jun. 3, 2009. This application is also related to U.S. Provisional Patent Application Ser. No. 61/113,855, filed Nov. 12, 2008, and U.S. Provisional Patent Application Ser. No. 61/122,621, filed Dec. 15, 2008. This application is also related to U.S. Provisional Patent Application Ser. No. 61/185,081, filed Jun. 8, 2009, entitled "Automated Human Papillomavirus Assay and System". The present application claims the benefit of, claims priority to, and incorporates herein by reference each of the foregoing references. This application also claims the benefit of U.S. Provisional Patent Application Ser. No. 61/242,671, filed Sep. 15, 2009, entitled "Automated assay and system." This application is also related to U.S. patent application Ser. No. 12/588,304, filed Oct. 9, 2009, now U.S. Pat. No. 8,357,538.

BACKGROUND

1. Field of the Art

The present disclosure relates to automated sample processing systems, and provides systems and methods that permit high-throughput specimen processing. Systems according to the invention may permit greatly increased sample processing throughput, decrease the number of samples that can not be assayed because of inadequate sample volume for assay detection, decrease the need for manual labor and allow for productive use of an operator's "walk-away time" during sample processing. Aspects of the disclosed systems may be used independently or in other systems.

2. Description of Related Art

Historically, biological samples being tested in the context of medical services have been processed using labor-intensive manual methods, or semi-automated methods requiring careful supervision by a laboratory technician. Such systems can be prone to operator error in many forms, such as improper testing (e.g., using an improper reagent or misreading the results), sample loss (e.g., spilling a sample), and identity loss (e.g., losing the patient name or associating the sample with the incorrect patient). While semi-automated methods may help reduce labor costs and operator error, many automated systems are cumbersome to use. For example, many "automated" systems are actually only semi-automated, and may require labor-intensive pre-processing steps to transfer the input samples into a format, such as a particular sample container, that the machine can accept. Others perform a subset of processing steps but require an operator to manually perform the others. It has also been found that existing semi-automated systems may lack safety controls, require frequent stopping for service, operate inefficiently or slowly, or have other problems or shortcomings.

There exists a need in the art for alternative automated and semi-automated processing systems, processing systems that can accept samples in various formats, and processing systems that can simultaneously process different kinds of samples. There also is a need for alternative sample processing methods. There also is a need for alternative sample processing equipment and sub-systems that may be used to assist with sample processing tasks in fully-automated, semi-automated and manually-operated systems.

SUMMARY

In one aspect, there is provided an automated sample processing system having a sample input adapted to simultaneously receive a number of sample containers, a reagent input adapted to receive one or more new reagent supplies, a consumable input adapted to receive one or more new consumable supplies, a solid waste output adapted to receive used consumable supplies, a liquid waste output adapted to receive one or more used reagent supplies, and a processing center. The processing center includes a decapper adapted to remove a lid from at least one sample container, an aspirator adapted to remove a specimen from the at least one sample container and transfer the specimen to an output vessel, and a capper adapted to replace the lid on the at least one sample container. The system also includes a sample output adapted to receive the output vessel, and a user interface adapted to receive an input from the user to indicate the identity of the at least one sample container, and control at least one operation based on a physical property of the at least one sample container.

BRIEF DESCRIPTION OF THE DRAWINGS

FIGS. 6A and 6B are isometric partial views of a barcode reader, shaker unit and decapper/capper unit shown in the decapping position in FIG. 6A, and the aspirating position in FIG. 6B.

FIG. 7A is an isometric view of an exemplary bellows gripper for use in one embodiment of a DCU.

FIGS. 9A-9C are schematic diagrams of a DCU system showing various aspects of its operation and capabilities.

FIGS. 10A-10F are schematic diagrams of a DCU system showing various aspects of its operation and capabilities.

FIGS. 17A and 17B are cross-section side elevation views of the pipettor of FIG. 16 shown before being fully inserted into an ETU in FIG. 17A, and after being fully inserted in FIG. 17B.

FIGS. 19A-19D are schematic drawings illustrating two exemplary final transfer operations between an ETU and a sample tray.

FIGS. 23-25 are charts illustrating the results of an exemplary assay protocol.

DETAILED DESCRIPTION

Figure 1:
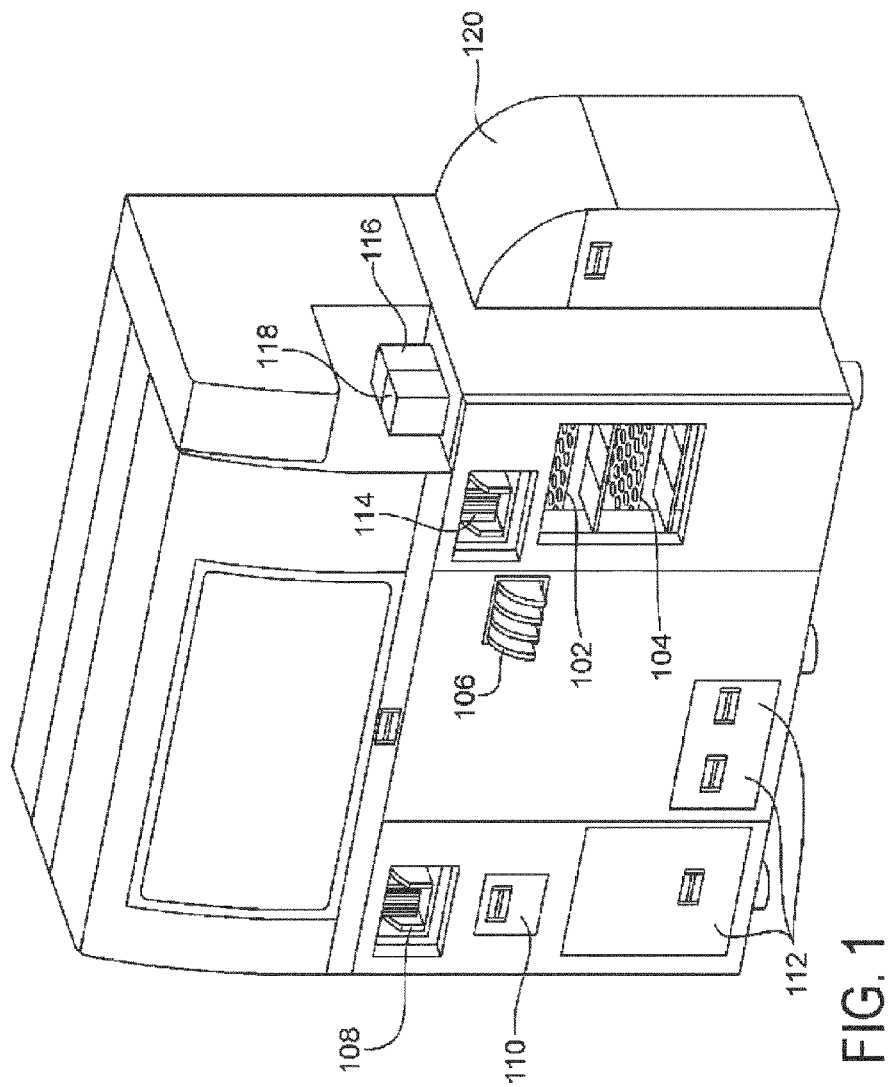
FIG. 1 is an isometric view of an exemplary automated sample processing system according to one embodiment of the invention.

The present disclosure provides various exemplary embodiments of automated or semi-automated sample processing systems, methods for automated, high-throughput sample processing, control systems for coordinating and controlling the operations of a high-throughput specimen processing systems, and various devices that may be used in the foregoing sample processing systems or in other processes, devices or systems. Preferred embodiments of the invention may provide faster, more reliable, and cheaper methods and machines for high-throughput patient sample processing, but other benefits may be realized instead of or in addition to these.

As noted above, exemplary embodiments of these systems may provide greatly increased sample or specimen processing throughput. For example, one embodiment of a system described herein may process about 1,400 biological samples through a ten-step protocol during a single 8-hour shift, producing purified DNA in a convenient 96-well format from animal cells provided in standard sample collection tubes. Another exemplary embodiment of an automated system may generate up to 2000 clinical results per 8-hour shift. Embodiments of the invention also may decrease the need for manual labor and allow productive use of an operator's "walk-away time" during sample processing. For example, walk-away time may be increased and efficiently used by providing large reservoirs of required materials (including samples), as well as by providing continuous or periodic access to inputs and outputs. These features allow flexible time windows for re-stocking the machine, allowing the machine to operate at full capacity while the operator attends to other tasks until required to resupply or remove completed samples from the machine during a restocking window.

In other aspects, embodiments of the invention may provide improved extraction of a sample volume from a tube or vial containing the sample during high throughput processing. This may result in fewer incidences of samples that can not be analyzed due to inadequate sample volume being available for detection, which, in turn, minimizes the need to collect additional samples from patients. Still further, embodiments may use unique sample processing logic to avoid unnecessarily processing samples that have too little volume to test reliably.

The systems described herein can be used to perform steps required in many common clinical or research laboratory methods. Exemplary embodiments can be used with a DNA analysis assay, such as the Next Generation Hybrid Capture® High Risk assay developed by QIAGEN Gaithersburg, Inc., of Gaithersburg, Md. ("Qiagen"). This assay may maintains high clinical sensitivity for high grade cervical disease established by the Hybrid Capture 2 during numerous large scale clinical studies, while creating a highly specific result. Examples of this and other assays that can be performed by embodiments of the systems described herein are disclosed in U.S. Provisional Application Ser. Nos. 61/231, 371, filed Aug. 5, 2009, entitled "METHODS AND KITS FOR ISOLATING NUCLEIC ACIDS USING AN ANION EXCHANGE MATRIX" and 61/147,862, filed Jan. 28, 2009, entitled "SEQUENCE SPECIFIC LARGE VOLUME SAMPLE PREP SOLUTION UTILIZING HYBRID CAPTURE TECHNOLOGY," which are incorporated herein by reference in their entireties.

It will be understood that the foregoing assays are exemplary and that the subject system may be used for performing other clinical processes or detecting other moieties such as other nucleic acids, proteins, small molecules, cells, viruses and the like. Indeed, while laboratory protocols are often quite diverse in their particular steps, many generally rely on various common underlying operations, such as the addition of reagents, mixing, incubating, and so on. Embodiments of the invention described herein may be adapted to provide the ability to perform a diverse set of common laboratory operations in a standard tube format, with different systems readily constructed from combinations of processing stations to perform steps required in virtually any protocol. The systems provided herein may be utilized, for example, for high-throughput preparation of DNA, RNA, protein, plasmids, chromosomes, antibodies, or organelles. Other systems may be used to perform all or part of methods such as: transformation; mating (e.g., of yeast, nematodes, or other small organisms); cloning; dot blotting (for DNA, RNA, protein, enzyme, etc.); mutagenesis; preparation for sequencing; nucleic acid amplification; primer synthesis; ELISA; enzyme assays; X-gal staining; immunohistochemistry; immunofluorescence; sample fixing; flow cytometry; in-situ hybridization; in vitro transcription and/or translation; sample purification from agarose; peptide synthesis; combinatorial library preparation; and so on. Processes using embodiments of the invention may employ samples of virtually any origin including, for example: prokaryotic cells; eukaryotic cells; tissue samples from multicellular organisms; whole organisms (e.g., flies, worms, or other similarly small organisms); conditioned media; environmental samples; and so on. Exemplary protocols that may be performed include those shown in the texts "Molecular Cloning: A Laboratory Manual" (Third Edition, Cold Spring Harbor Press) or "Condensed Protocols From Molecular Cloning: A Laboratory Manual" (First Edition, Cold Spring Harbor Press), the disclosures of which are hereby incorporated by reference in their entireties. Further, embodiments of the invention may be adapted to provide any suitable output format, in addition to the 96-well and 384-well formats described below, such as outputs to a membrane or blotting paper, bacterial, yeast or mammalian cell culture plate, and so on.

Figure 2:
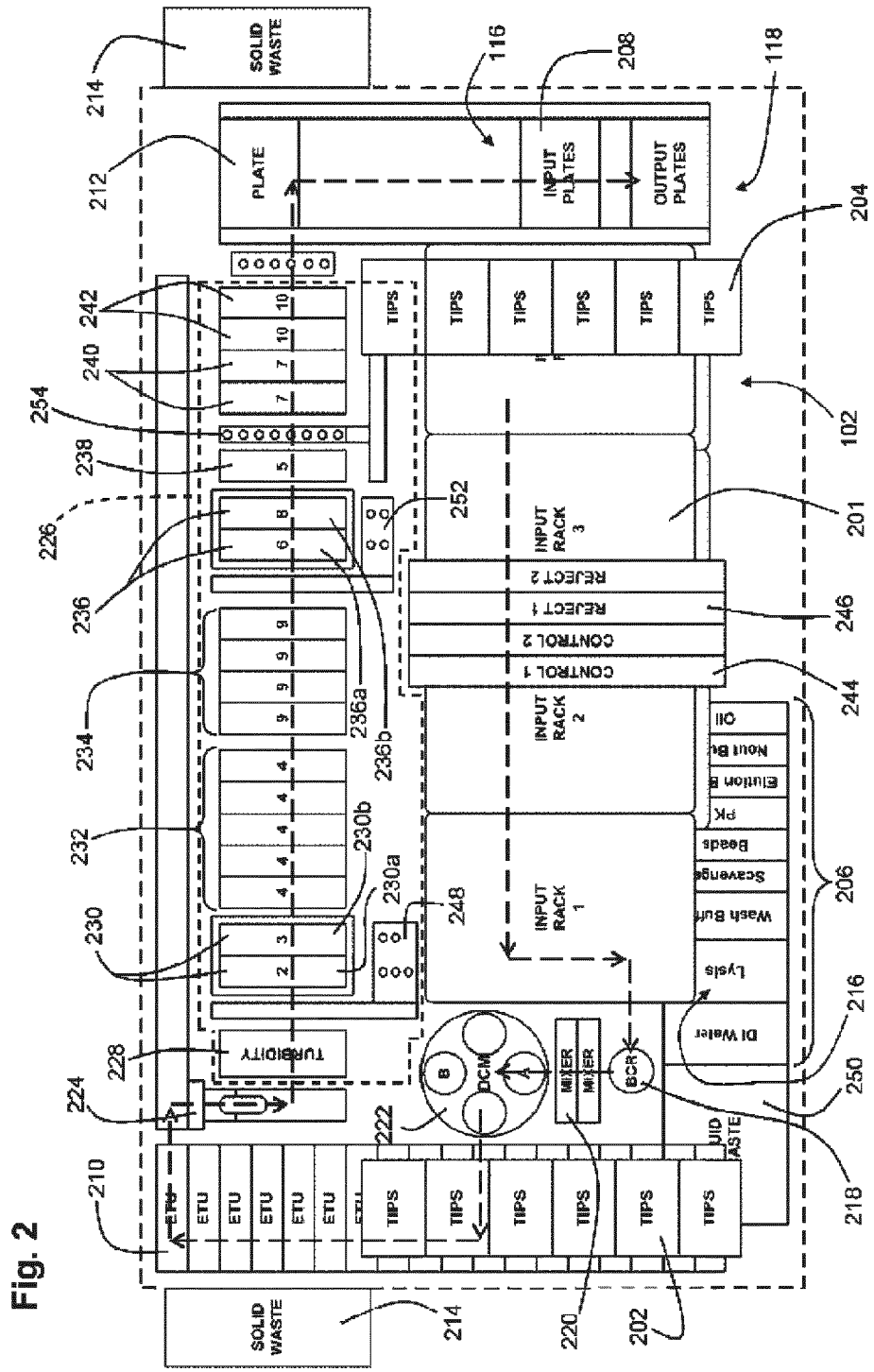
FIG. 2 is a schematic top plan view of the embodiment of FIG. 1, with the bottom of the figure corresponding to the front of the machine.
Figure 3:
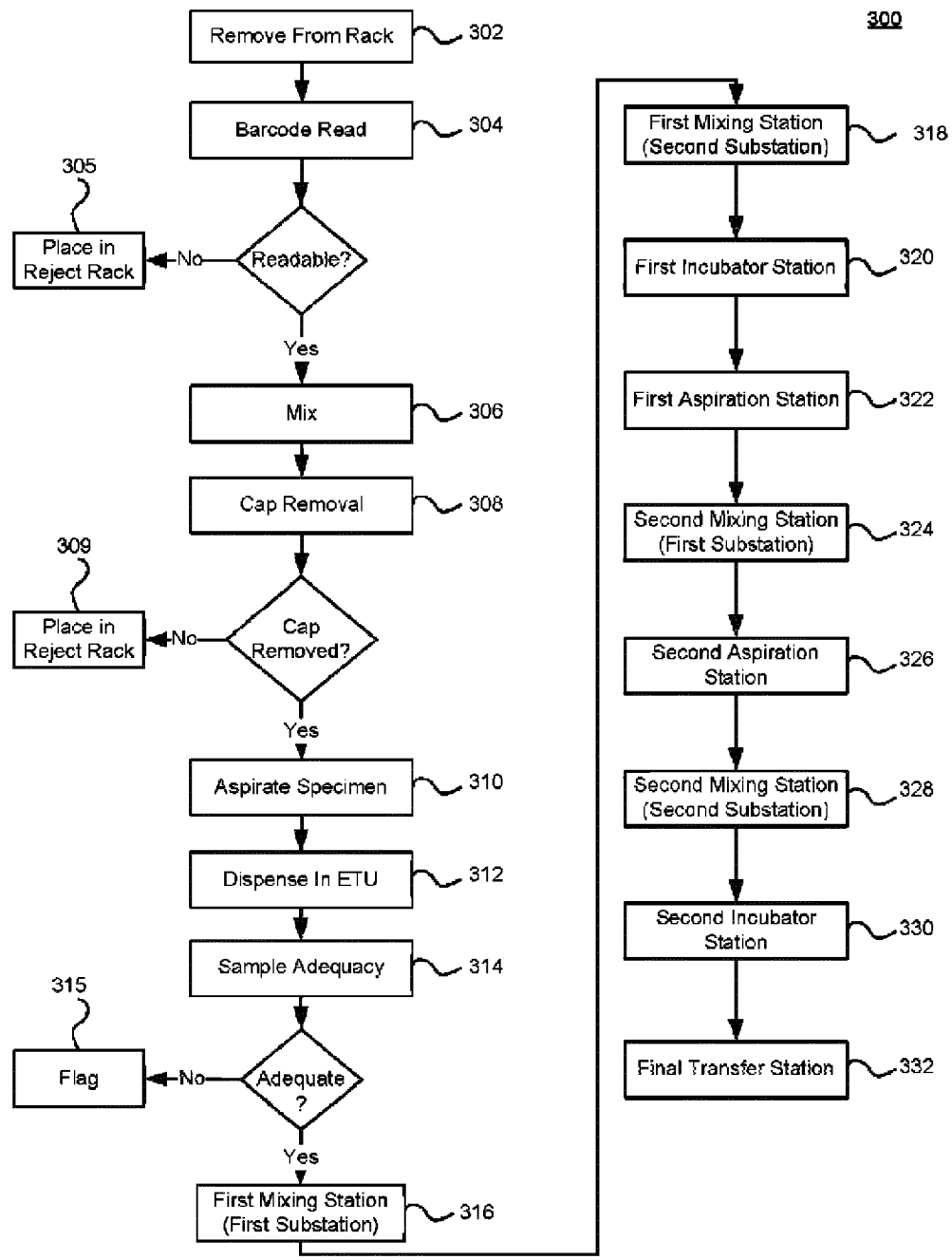
FIG. 3 is a schematic diagram of an exemplary assay protocol that may be conducted using the embodiment of FIG. 1.

Referring now to FIGS. 1 and 2, an exemplary embodiment of an automated system in the form of a pre-analytic system ("PAS") 100 is described in detail. FIG. 1 is an isometric view of the PAS 100 showing the device with its exterior coverings in place. FIG. 2 is an overhead schematic view of the PAS 100, in which some features are partially or fully obscured by items located above those features, but their location and operations still will be clear from the Figures and following discussion. This embodiment of a PAS 100 extracts DNA from patient samples, such as cervical samples taken from a so-called "pap smear," cervical cell samples taken into a sample collection medium such as that described in provisional application 61/108,687 filed Oct. 27, 2008 (which is incorporated by reference herein), that described in U.S. application Ser. No. 12/605,605 filed Oct. 26, 2009 or any other source of patient cells.

The PAS 100 or other embodiments of a pre-analytic system may be used in conjunction with an analytical system that analyzes or tests the samples (such as by analyzing DNA that may be present in the sample). For example, an exemplary analytical system may be capable of carrying out the steps of a nucleic acid detection assay such as those described in Qiagen's Hybrid Capture 2 assay or Next Generation Hybrid Capture® Assay protocols. Such steps may include sample loading, target nucleic acid denaturation, probe hybridization, target capture, signal production, signal detection and assay result reporting. An exemplary analytical system that may be used to perform these or other assays is the QIAensemble JE2000, available from Qiagen.

A central control unit (CCU) may be used to control and/or monitor the PAS 100 and/or a downstream analytical system, and an exemplary CCU may provide a processing interface between the PAS and the analytical system. For example, a CCU may be combined with a PAS and an analytical system to perform all of the steps necessary to pre-process and test a sample according to the Hybrid Capture 2 or Next Generation Hybrid Capture® protocols.

The exemplary PAS 100 is a generally self-contained unit having various input and output locations at which an operator can provide supplies and remove waste and processed samples. In the exemplary embodiment, the PAS 100 includes a sample rack input 102, a sample rack output 104, a control vial and reject vial access point 106, a first pipette tip input 108, an ETU input 110, reagent trays 112, a second pipette tip input 114, a sample plate input 116, a sample plate output 118, and one or more solid waste outputs 120. The functions of these various inputs and outputs are described in more detail below. The PAS 100 also may include a suitable electrical interface (not shown) for connecting to a CCU that controls the device. Of course, the CCU, or various parts of it, may be integrated into the PAS 100 itself, in which case the PAS 100 may be provided with a human interface to receive operating instructions and/or display system status. Such an interface may include various interface elements known in the art, such as a monitor, touch-screen monitor, keyboard, mouse, microphone, speaker, barcode reader, and so on. While the shown arrangement of inputs and outputs has been selected for this embodiment, it will be understood that other arrangements may be used in other embodiments.

The exemplary PAS is adapted to process biological samples, including liquid-cased cytology (LBC) samples into standard 96-well plates containing the extracted sample nucleic acid. During processing, the samples are taken from standard sample containers, and processed in a strip of test tubes, called the extraction tube unit ("ETU"). An example of an ETU is described below in detail with respect to FIG. 11. Each ETU may have any suitable number of test tubes, but in one embodiment the ETU has eight test tubes to conveniently correspond to a row of a 96-well plate.

Exemplary System Preparation

The PAS 100 is prepared for operation by loading it with samples to be processed, and consumable elements, such as pipette tips 202, 204, reagents 206, sample plates 208, and ETUs 210.

In the shown embodiment, the pipette tips 202, 204 are loaded into the first and second pipette tip inputs 108, 114. The pipette tips 202, 204 may be provided in any suitable form or carrier. In the shown embodiment, the pipette tips 202, 204 are provided in racks that each hold multiple tips 202, 204 in a vertical orientation to facilitate their retrieval by an automated pipettor. Multiple pipette racks, which are represented by rectangles in FIG. 2, may be loaded into the PAS 100 at one time, and advanced to the automated pipettor location by conveyors, robot arms, or other suitable devices as known in the art. In this embodiment, the pipette tip inputs 108, 114 comprise simple rectangular openings that feed into the pipette rack conveyors. If desired, doors or other covers may be provided over these openings. The racks may be deposited into one or more solid waste containers 214 once all of the pipettes are removed. In addition, used pipettes may be deposited in the racks before they are discarded to minimize solid waste volume.

Reagents 206 are loaded into one or more reagent trays 112. The trays 112 may be mounted on racks to slide out from the front of the PAS 100 to facilitate loading and unloading. In addition, each tray 112 may hold multiple reagent bottles, which are connected to fluid lines to convey the reagents to the necessary locations. If necessary, the trays 112 may include clamps, straps, or appropriately-sized pockets to hold the bottles in place. As used in this context, the reagents may comprise any fluid or other material that is used in the processing steps undertaken within the PAS 100, such as chemical solutions, deionized water, lysis, buffers, oils, capture bead suspensions, and the like.

Sample plates 208, such as standard 96-well sample plates known in the art, are loaded into the sample plate input 116. In the shown embodiment, multiple sample plates 208 are stacked on top of each other at the sample plate input 116. During operation, the lowermost plate 208 is advanced to a sample plate loading position 212 by a conveyor or other suitable means. Once filled, the sample plate 208 is returned to the sample plate output 118, and added to the bottom of a stack of previously-filled sample plates 208. The filled sample plates 208 are raised upwards to the sample plate output 116, where they are retrieved by an operator.

ETUs 210 are loaded into the ETU input 110. The ETU input 110 leads to an ETU rack that holds the ETUs. Conveyors or robot arms advance the ETUs 210 to a first position at which the ETUs 210 are filled, and a second position at which they are removed from the rack and conveyed for further processing. As explained below, the ETUs comprise may be constructed to facilitate their movement along a conveyor or by a robotic arm or other mechanism.

Samples are introduced into the PAS 100 by loading them into a sample rack 201 (FIG. 2), and sliding the sample rack 201 into the sample rack input 102. The sample rack 201 is moved by a conveyor from the sample rack input 102 to a processing location 216, and then back to the sample rack output 104 located below the sample rack input 102. Any suitable conveyor system may be used for this purpose. For example, a conveyor belt, robotic arms, or powered rollers may be used to move the sample racks 202 laterally, and an elevator may be used to lower the sample racks 202.

As shown in FIG. 2, as number of sample racks 202 may be loaded in the PAS 100 at any given time. While it would be possible to scale embodiments such that the rack 202 includes only a single sample (or to simply eliminate the rack and use the original sample container as the sample carrier), higher productivity is likely to be achieved by including a number of samples on each rack. In one embodiment, each sample rack 201 may include forty-two or forty-eight sample positions arranged in a rectangular array. Where the number of sample positions is increased, it may be necessary to provide greater accuracy to the equipment (such as a robotic arm) used to extract the sample containers. In addition, each sample position may be configured to hold sample containers of one or more different sizes, which is particularly helpful where the PAS 100 is used to process samples that typically come from various different sources. As one example, the sample rack 201 may be adapted to hold sample vials typically used in the known PreservCyt, SurePath, and/or DCM testing kits.

Exemplary Processing Overview

The PAS 100 processes the samples generally along a path designated by the dotted arrow line. There are three general processing stages: an initial transfer stage in which each sample is transferred to a processing vessel (and in which some other processing may occur), a second stage in which the samples are analyzed or processed into an analyzable format, and a final stage in which the samples are transferred to a standardized output vessel. The output vessel—here shown as an exemplary 96-well plate—may then be removed and analyzed.

In a preferred embodiment, the PAS 100 uses a processing system in which the various steps are timed according to a repeating, fixed-length internal clock cycle. The clock cycle may be arbitrary, or it may be based on processing parameters, such as the durations of particular processing steps. For example, if one processing step takes 100 seconds, with transport time to that step taking 20 seconds, and the remaining processing steps can be completed within that 120-second time frame or a multiple of that time frame, the clock cycle may be set at 120 seconds. In the exemplary embodiment, the clock cycle is about 150 seconds (2½ minutes). In this embodiment, each process or combination of processes generally occurs during one full clock cycle or a multiple of the clock cycle time. In most cases, each ETU is moved to the next processing step once per clock cycle. In some instances, a processing step can be carried out over multiple clock cycles, which may be accommodated by having multiple stations able to perform the same step in parallel. It will be appreciated that some variation in the execution time of each step may exist due to transport times, and some processes may take less than a full clock cycle and sit idle until the next process begins. It will also be understood that the clock cycle may be universal across all processing stations (that is, the clock cycle at each station is measured based on a single universal timer), or the clock cycle may be relative at each station (for example, the clock cycle at each station may begin once a sample is placed in it). The latter system may be useful where transportation times occupy a significant portion of the clock cycle, which may be the case where a single ETU transport mechanism is used. Using the foregoing system, throughput can be increased by processing multiple samples in a parallel manner—simultaneously performing each processing step on multiple samples. The processing steps may be grouped with similar steps to create processing stations or modules, which may improve efficiency and reduce system size.

In the initial stage, the samples, provided in the sample racks 202, are moved towards a transfer station having a barcode reader 218, a mixing unit 220, and a decapper/capper unit 222. Each sample is processed at the first transfer station, as shown by arrow segment A2, by removing the sample container from the sample rack 201, reading a barcode on the sample container using the barcode reader 218, mixing the sample container in the mixing unit 220 to homogenize the contents, and decapping the sample container at the decapper/capper unit 222. Next, an automated pipettor (not shown) transfers an aliquot of sample from the sample container to an ETU 210. When it is full, the ETU 210 is advanced to a transfer unit 224 that moves the ETU from the ETU rack into a processing area 226.

In the shown embodiment, the processing area 226 comprises one or more processing stations. The type and number of processing stations may vary depending on the particular use for which the PAS 100 is employed. For example, the processing area 226 may include a sample adequacy station 228, a first mixing station 230, a first incubation station 232, a second incubation station 234, a second mixing station 236, a first aspiration station 238, a second aspiration station 240, and a final transfer station 242. Stations may include multiple ETU receptacles or be duplicated to permit an operation to continue across multiple clock cycles, as further described below. The processing stations may be provided in a row within a single continuous chamber. This arrangement may simplify the construction or operation of the PAS 100 in various ways. For example, is may be possible to use a single transport mechanism, such as a robotic arm, to move the samples along the processing stations. Also, access to all of the processing stations may be conveniently available from the back of the machine. While the foregoing linear arrangement is believed to provide certain benefits, it is not required in all embodiments, and in other instances a carousel-like arrangement or other arrangements may be used.

The use of a fixed clock cycle and the various input and output features on the PAS 100 enable continuous operation with relatively little user input. During operation, samples are periodically added at the sample rack input 102, and processed racks are removed from the sample rack output 104. Four racks may be loaded into the device for processing, and there is space for three processed racks. Without user intervention, processing may stop once a fourth rack is completed processing (although processing may continue for a short while even after the fourth rack is completed by providing an access arm that obtains samples from a fifth rack, as explained below). Thus, the exemplary embodiment can be said to operate on a four-rack service interval. All four processed racks may be removed during servicing to permit continuous operation to process four more racks without intervention. To minimize the amount of service time necessary to operate the system, it may be possible to load the PAS with sufficient supplies of reagents, pipette tips, ETUs and sample trays to process four or more full racks before requiring further service. In addition, throughout operation, solid and liquid waste containers 214, 250 receive expended pipette tips, ETUs, ETU racks, aspirated liquids, and so on. The sizes of these containers may be selected to be approximately filled during the four-rack service cycle, but other sizes are possible.

While the foregoing features may be provided in some embodiments, the use of convenient access points preferably permits a user to continuously add supplies and remove waste at virtually any time during operation. This maximizes the ability to service the device while performing other tasks while the machine operates. Input racks may be added and removed as samples are processed. As the system processes an input rack in approximately 15 minutes, additional racks may be added (and completed racks removed) at any time between 15 minutes and 1 hour after operations commence, allowing greater utilization of walk-away time. Two control holders and two reject holders permit operations to continue even when user attention is required, as one control holder may be filled (or reject holder emptied) while the other is kept available for use. Embodiments also may employ a visual indicator to show when attention to a control or reject holder is required, and can lock the control or reject holders or other access points to prevent user access of a holder that is reserved for use or prevent access when internal operations are being performed at the access point.

Various sensors may be used to detect the quantity of supplies, and such information may be displayed on a user interface or otherwise communicated to an operator. For example, ultrasonic sensors or other devices known in the art may detect the number of pipette tips, ETUs, and output plates available, and the levels of solid and liquid wastes, and report these levels to the control unit. In order to prevent unnecessary stops during processing, the control unit can be programmed not to permit sample processing to begin unless sufficient supplies/waste capacity are available for processing to proceed to completion. A visual indicator may be used to show levels of supplies, waste, and input samples. Optionally an audible alarm may be sounded to warn of critically low levels of supplies, and/or to warn of cessation of operations due to low reagent levels or malfunctions. The audible alarm may include voice prompts to help identify the fault or specific supplies needed.

As with the other consumables, one or more of the reagents may be monitored by sensors to detect their levels. The reagents may be added in containers, with a siphon extending down into each reagent container, and pumps to draw reagents to on-board reservoirs. Liquid level sensors determine the amount of reagent present in each reservoir, allowing the control system to only begin processing a sample when sufficient reagents are on-board for complete processing. Additionally, the on-board reservoir acts as a "bubble trap" because any air that enters the transport line between a reagent container and its reservoir will float to the top of the reservoir and not be drawn into the dispensing system, which uses a separate inlet in the reservoir and an associated pump to draw fluid from each reservoir. The use of an intermediate reservoir also allows reagent bottles to be changed without interrupting the reagent supply to the PAS. In some cases, certain reagents may require periodic mixing. For example, some reagents containing macroscopic particles (e.g. capture beads, solid catalysts, etc.) that are prone to settling and/or forming clumps may need to be mixed periodically. The system keeps such reagents sufficiently mixed by recirculating the reagent between its reservoir and reagent container or within the reservoir itself. Additionally, when the system is expected to be inactive for a period of time (e.g., at the end of a shift, for maintenance, etc.) such reagents can be pumped out of the dispensing lines back into their input container. High cost reagents are likewise conserved by being pumped back into their input container when the system is expected to be inactive for a period of time.

Processing Example

An exemplary embodiment of a processing method is now described with reference to FIGS. 2 and 3A-3F. While the following processing method helps explain the processing operation of one exemplary PAS 100, as well as the operation of the foregoing exemplary processing stations, it will be understood that it does not limit the disclosure in any way.

In the embodiment of FIGS. 3A-3F, the PAS 100 is configured to perform two different assay protocols: the "PC" and the "Surepath" protocol. These protocols are intended to prepare the samples to be tested for the presence of human papilloma virus ("HPV") DNA. In this embodiment, two protocols are used because the samples may be provided in different bottles and/or mediums.

Beginning in step 302, a sample container is removed from a sample rack 201 by a robotic arm or other suitable mechanism. In some cases, such as where it may be desired to verify test results or system operation, the sample container may instead be removed from a control sample rack 244 that holds a number of control samples. In step 304, a barcode reader 218 reads a barcode on the sample container to identify and/or track the sample. If no barcode is present or the barcode does is not associated with a patient or otherwise recognized by the system, the sample container may continue through processing or, more preferably, be removed to a reject vial rack 246 as shown by step 305. The reject vial rack 246 must be manually emptied by the user, which helps ensure that failures are noticed by the operator and any appropriate follow-up action is taken. Samples can be rejected for many reasons, including: quantity not sufficient (QNS), unable to remove cap, barcode unreadable or not recognized, etc. For example, unremovable caps may be manually loosened or the sample transferred to another container; samples having unrecognized or unreadable barcodes can be manually identified; and QNS samples may be manually processed (optionally with addition of an agent that facilitates sample extraction) or may be reported to a care provider or patient as having been unassailable.

In step 306 the sample is mixed to homogenize the contents of the sample container. The samples can be mixed or agitated by various methods and devices known in the art, and it is not necessary to explain the details of such mixing means here. Examples of shakers include orbiting shakers, vertical shakers, inversion shakers (suitable for closed sample containers), platform shakers, combination shakers (e.g., shakers similar to those used as commercial paint mixers), paddle-style mixers, vibration mixers, ultrasonic mixers, and any combination thereof. The means of agitation may vary on factors such as the shape of the container in which the sample is held, the nature of the specific samples being analyzed and the moiety therein which is being detected.

In step 308, the cap is removed from the sample container. If the cap can not be removed, the sample container is removed to the reject rack 309 and addressed as noted above. With the cap removed, a specimen of any suitable size (e.g., 2000 ul in the PC protocol and 1500 ul in the Surepath protocol) is removed from the sample container in step 310. In step 312, this specimen is dispensed into a test tube for further processing. After the sample is removed, the cap is returned to the sample container, and the sample container is replaced on the sample rack 201, preferably to its original position. Any suitable device may be used to transfer the specimen to the ETU. For example an automated pipetting system such as those available from STRATEC Biomedical Systems AG of Germany may be used. As noted above, the test tube may be part of an ETU having multiple tubes, but any other suitable vessel may be used to hold the specimen in other embodiments.

In the exemplary embodiment, the ETU has eight test tubes, and therefore accommodates eight samples. As explained below, each ETU is processed downstream according to the exemplary 150-second clock cycle. As such, steps 302, 304 and 308 are conducted eight times during each clock cycle (i.e., once every 18.75 seconds) so that the ETU is filled and moved into place to be ready as each clock cycle begins. Of course, these steps may occur more quickly, provided a delay is included to prevent them from exceeding the rate at which the remaining operations occur.

Next, the ETU containing the specimen is placed in the sample adequacy station 228, where it is tested in step 314 to determine the adequacy of the sample for further processing. In an exemplary embodiment, step 314, including transportation to the sample adequacy station 228 may take approximately one full 150-second clock cycle to complete. Any suitable sample adequacy testing device may be used. For example, the sample adequacy station 228 may comprise an optical measuring system, in which the turbidity of the sample is optically measured to determine whether the sample contains an adequate amount of cells. One example of such a device is shown in U.S. application Ser. No. 12/588, 305, entitled "Ensuring Sample Adequacy Using Turbidity Light Scattering Techniques" and filed on Oct. 9, 2009, which is incorporated herein by reference in its entirety. An exemplary turbidity measurement preferably is performed within about ten minutes of after the sample is dispensed in the ETU to prevent inaccuracy that may be caused by the sample settling. Optionally, the ETU may be agitated, such as by the device that moves it to the sample adequacy station 228, or by a shaker mounted to the station 228, to help ensure an accurate turbidity measurement. Turbidity also may be measured again after an interval of time to determine how much of the turbidity initially measured is due to classes of non-cellular material with a different (faster or slower) settling profile than cells (e.g., hair, mucus, bacteria), which may provide greater sample accuracy assurance. If it is determined that the sample is not adequate for further testing (e.g., too few cells are present in the sample), the PAS 100 control system may flag the sample in step 315. Flagged samples may continue to move through the processing area 226, but reagents will not be deposited into the sample to prevent the unnecessary waste of valuable consumables. For simplicity, however, an inadequate sample may simply progress as if it were an adequate sample, but the results will be noted as being based on an inadequate sample. In other embodiments, if the sample adequacy measurement indicates that a sample contains insufficient cells, the system may be configured pipette the sample back to its original container and move the container to the reject rack 246.

In step 316, the ETU 210 containing the samples is moved to the first mixing station 230. The first mixing station may have two separate substations, 230a, 230b, each of which is sized to hold one ETU. It will be understood that, in other embodiments, the first mixing station may have a single station, or more than two substations. The substations 230a, 230b may be separate from one another, but preferably are connected to a common platform and a single shaker unit. The ETU is positioned in the first sub-station, where suitable amounts of a first reagent (60 ul for both protocols) and a buffer (1000 ul for the PC protocol and 1200 ul for the Surepath protocol) are added to the samples, and the samples are is mixed (e.g., for 15 seconds at 1000 rpm). While still in the first sub-station 230a, a second reagent may be added (e.g., 25 ul), and the sample may be further mixed (e.g., 30 seconds at 1000 rpm). The ETU remains in the first substation 230a for one full clock cycle (less time necessary for transport). Any suitable agitator or shaker unit may be used at the mixing station 230 to mix the samples. Examples of such devices are described briefly above, and need not be described here.

In step 318, the ETU is moved to the second substation 230b of the first mixing station 230. Here, the samples are mixed (e.g., for 15 seconds at 1000 rpm), a third reagent may be added (none for the PC protocol, and 100 ul of a third reagent for the Surepath protocol), and the samples are mixed again (e.g., for 30 seconds at 1000 rpm). The ETU remains in the second substation 230b for one full clock cycle (less time necessary for transport). It will be understood that it is not strictly necessary to move the ETU from the first substation 230a to the second substation 230b in all embodiments.

One or more dispensers, such as a movable dispensing unit 248, may be provided to add the buffers and reagents to the samples in substations 230a, 230b. The dispensing unit 248 may be controlled to dispense the correct amount of reagents or buffers in accordance with the type of sample located in each test tube along the ETU. Reagents can be dispensed through fluid systems using pumps, pistons, and other means known in the art. Reagents can be dispensed through a nozzle that is in contact with a liquid sample into which it is to be dispensed, in which case it may be desirable for the nozzle to be disposed of or be washed between dispenses into different samples, thereby decreasing sample carryover. Reagents can also be dispensed in drops or streams from a nozzle not in contact with the sample. The nozzle may have an opening with a diameter less than or equal to the diameter of the fluid transfer lines that transport the sample to the nozzle. Optionally the nozzle may simply be a continuation of the fluid transfer line. The nozzle may be made of a hydrophobic or superhydrophobic material, whereby droplets of sample are prevented from clinging to the nozzle and dispense location and volume are better assured. Reagent dispensers can be single-channel or multi-channel, for example, permitting a reagent to be dispensed in parallel into multiple containers. The details of such dispensers are known in the art, and no explanation of the same is necessary here.

In some embodiments, it may be desirable to dispense reagents containing macroscopic particles (e.g., capture beads, solid catalysts, etc.) into the sample. Macroscopic particles can be difficult to accurately and consistently dispense due to their tendency to become stuck in dispensing lines and on nozzles. To help address these potential difficulties, in one embodiment the PAS 100 may dispense a macroparticle suspension (for example, 60 ul) into the dispensing line for a larger-volume reagent that is added in the same processing step (for example, 1000 ml or 1200 ul of buffer). This helps flush the macroparticles through the dispensing line and ensure that the correct volume of beads is added. This methodology also may help prevent the macroparticles from drying out which could otherwise cause stickiness and clumping, leading to inconsistent results or machine downtime. In the embodiment shown, the first reagent may comprise 60 ul of fluid having a suspension of macroscopic capture beads. To obtain accurate dispensing of this fluid, the dispensing arm 248 may be positioned at the desired ETU position, and then the macroscopic particle suspension is dispensed into the buffer flow path at a simple T-junction (i.e., the suspension is injected generally at a right angle to the straight buffer flow path). The macroscopic particle suspension may be injected before the buffer flow begins, which may cause some of the buffer in the flow path to flow out of the dispensing nozzle. Once the suspension is in the flow path, the relatively large volume of buffer is dispensed horizontally through the T-junction, flushing out the beads and dispensing them into the ETU. As the reagent volume is larger than the volume of the flow path, the beads are completely dispensed into the ETU. In the embodiment shown, the flow path may be lined with Teflon™ (polytetrafluoroethylene) to help prevent the macroparticles from sticking.

Of course, other methods may be employed to introduce the macroparticles into the larger volume reagent path. For example, the macroparticles can be added via an injection loop of a standard HPLC injector which is then rotated to be in line with the buffer dispensing line; or they can be added to the dispensing line through a controlled or one-way valve. Because the macroparticle suspension is added to another reagent, it can be dispensed through a shorter path than if it were added directly to the samples; thus, the length of tubing dedicated to the macroparticles (which may require more frequent maintenance or replacement than the remainder of the system due to macroparticle accumulation or clogging) is decreased.

If desired, a system may be provided at the first mixing station 230 (or at any other stations at which fluid is added to the samples or measurement of the sample volume may be helpful) to help ensure that the reagents are fully dispensed into the ETUs. For example, one or more ultrasonic rangefinders may be used to measure the fluid levels in the ETU tubes after the reagents are dispensed therein. Such devices are well-known in the art and need not be described here. If the fluid level of any sample is found to be higher or lower than a predetermined tolerance range, an alert may be raised and the sample may be flagged as described above in step 315. If the fluid levels in a number of ETU tubes is deficient or otherwise outside a predetermined tolerance range, this may indicate a supply loss or problem with the supply lines, and the system may initiate a failure mode in which processing of additional samples is halted (although the system may be configured to continue processing samples that have adequate reagent volume to completion or to some predefined safe stopping points). The system may also be programmed with a feedback system to attempt to add reagents to under-filled samples (provided the type of missing reagent can be determined), or to actively measure the fluid level during dispensing to ensure proper fill levels during the dispensing process.

In step 320, the ETU is moved to the first incubation station 232, where the samples are incubated for a suitable time (e.g., 10 minutes at 60 degrees Centigrade for both protocols). As shown in FIG. 2, the first incubation station 232 may include multiple cells or substations, each of which can hold an ETU. Multiple cells are provided because the ETUs remain in the first incubation station 232 four times longer than the 150-second clock cycle. Thus, providing at least four cells allows ETUs to be inserted into and removed from the first incubation station 232 every 150 seconds, while each ETU is still properly incubated for 10 minutes. As shown, the first incubation station 232 may include one or more extra cells. If greater incubation time is desired, a greater number of positions in the heating block may be employed to provide sufficient space to accommodate ETUs for the corresponding number of clock cycles. Furthermore, assuming the incubation time remains 10 minutes, the addition of extra cells also allows the rest of the system to operate at faster clock cycles; for example, adding one extra cell, as shown, permits a 120-second clock cycle for the rest of the system.

The first incubation station 232 may use any suitable heating system to incubate the samples. For example, the first incubation station 232 may comprise one or more aluminum or steel heating blocks having cutouts that match the shape of the ETU and into which the ETU test tubes snugly fit to receive heat from the block. The heating blocks may be heated by electric resistance heaters or other means. In a preferred embodiment, the heating blocks ensure temperature uniformity within about one degree of the set point even as ETUs are being installed and removed. This may be accomplished by using feedback control mechanisms to control the temperature of the heating block, by providing insulation surrounding the heating blocks, by providing sufficient heating block mass to resist excessive temperature changes, or by any combination of these or other techniques. Additionally, the mass and shape of the heating block may be chosen to ensure that the temperature remains generally uniform and is not unacceptably perturbed when samples are inserted into or removed from the block. The design of suitable incubators (of the heating block type or other types) for the first incubation station 232 is well known in the art, and may be determined mathematically or through routine testing. If desired, a safety cut-off may be provided to cut power to the heating element if the temperature rises above a predetermined level, such as about 85 degrees Centigrade. Of course, higher or lower safety cut-off temperatures could be chosen depending on the particular application. For example, if a higher set temperature is used, a correspondingly higher safety cutoff temperature may be required; alternatively, a lower safety cutoff temperature may be desirable where volatile solvents or solvents with a particularly low flash point are used.

In step 322, the ETU is moved to the first aspiration station 238. The first aspiration station 238 comprises a magnet station that is adapted to hold the ETU and has one or more magnets that are positioned next to the ETU test tubes. Suitable magnet stations are known in the art. The magnets may be fixed in place or moved into position when the ETU is in place, and may comprise any suitable kind of magnet or electromagnet. Such magnets are known in the art, and embodiments of magnet arrangements are described subsequently herein with respect to FIGS. 14A and 14B. The magnets attract paramagnetic macroscopic beads mixed into the sample as the first reagent (see above), and capture these beads and any attracted material in place adjacent a sidewall of the tube. In an exemplary embodiment, a horizontal bar may be located opposite the magnets and slightly above them to cause a slight interference with the ETU test tubes that presses them against the magnets. Minimizing the distance between the ETU test tubes and the magnets in this way may provide a stronger and more consistent application of the magnetic field to the beads, and increase the speed and effectiveness of magnetic bead attraction. While the beads are magnetically captured, one or more aspirators are lowered into the tubes to remove fluids. Any suitable aspirator, such as known in the art or described subsequently herein with reference to FIGS. 15A and 15B, may be used to aspirate the fluid from the ETU test tubes. In an exemplary embodiment, the aspirator tips are made of a nonmagnetic material to avoid magnetic attraction of the aspirator tips to the side of the tube. In the exemplary embodiment, the magnets are applied to the ETU tubes for 90 seconds, and then the aspirator is activated to remove the fluid to a liquid waste receptacle 250. The magnets remain applied during aspiration, and preferably are simply fixed in place and applied at all times. An ultrasonic sensor may be used to verify that all of the liquid has been removed from the ETU test tubes after aspiration is complete; such devices are known in the art. The ETU remains in the first aspiration station for one full clock cycle (less time necessary for transport). After aspiration, the magnetic beads and the cells that are being tested remain in the ETU test tubes, possibly along with some small amount of fluid that was not removed during aspiration.

After aspirating the ETU test tubes in step 322, the aspirator may be cleaned (or the tips may be replaced) to prevent carryover from one sample to the next. Washing may be accomplished by lowering the aspirator into a bath 254 containing water and/or other cleaning solutions (e.g., bleach followed by water), and aspirating a quantity of water. Washing may be done during the initial 90-second magnet application in step 322, and preferably does not take a full clock cycle to complete. It is believed that this washing technique is sufficient to prevent sample carryover in the context of an exemplary HPV nucleic acid assay. Optionally, the aspirator may be cleaned by dipping it in and out of a wash solution while vacuum is applied, creating greater turbulence and shear force due to the intermittent drawing of air, which is expected to provide greater cleaning ability. The foregoing protocol may also attain sufficient cleaning with less production of liquid waste. If desired, testing may be routinely performed to ensure that washing is sufficient to achieve acceptably low levels of sample carry-over. If greater cleaning is desired, detergents, organic solvents, salts, and/or heating of the cleaning solution may be employed. The bath 254 also may use a continuously or intermittently flowing cleaning solution or water supply to prevent the accumulation of contaminants therein.

In step 324, the ETU is moved to the second mixing station 236. Like the first mixing station 230, the second mixing station may have two substations 236a, 236b that are mounted on a common platform with a common shaking mechanism. For step 324, the ETU is placed in the first substation 236a, and a suitable amount of a second buffer is dispensed into the ETU test tubes (1000 ul for both protocols) by another dispensing unit 252. This dispensing unit may be constructed as described above or in any other suitable way, as known in the art. After the buffer is dispensed, the ETU is mixed (e.g., for 30 seconds at 1500 rpm). The ETU remains in the first substation 236a of the second mixing station 236 for one full clock cycle (less time necessary for transport).

Next, in step 326, the ETU is moved to the second aspiration station 240, where a magnet is used to attract the paramagnetic beads for 120 seconds, and the fluid is aspirated to waste using an aspirator. The aspirator may be the same aspirator used in step 322, and the aspirator may be cleaned, such as described above, immediately after this aspiration step. The use of a 120 second magnet application before aspirating in this step may allow more complete capture of the magnetic beads, and may help provide sufficient time for the aspirator to be used in step 322, cleaned, and then used in step 326 on an ETU that is further along in the process path. The ETU remains in the second aspiration station for one full clock cycle (less time necessary for transport). If there is insufficient time to perform the both aspiration steps (i.e., step 322 and 326) one or both of the aspiration stations may include a second substation in which a second ETU can be placed. This allows the aspiration in step 326 to overlap clock cycles or occur at the beginning of a second clock cycle.

In step 328, the ETU is moved to the second substation 236b of the second mixing station 236. Here, a suitable amount of a third buffer is dispensed into the ETU test tubes (30 ul for both protocols), and the contents of the ETU test tubes are once again mixed (e.g., for 30 seconds at 1500 rpm). The ETU remains in the second substation 236b for one full clock cycle (less time necessary for transport).

The ETUs next are conveyed to the second incubation station 234, where, in step 330, the samples are incubated for a suitable time (e.g., 10 minutes at 68.5 degrees Centigrade for both protocols). The second incubation station may comprise any incubator, as known in the art. As shown in FIG. 2, the second incubation station 234 may include multiple cells, each of which can hold an ETU. Additional or fewer cells may be provided, as necessary.

After the second incubation is complete, the samples are moved to the final transfer station 242 where the samples are transferred to a sample tray 208 in step 332. Here, the ETUs are placed in mounts that hold them in place and magnets are once again applied to the sides of the ETU test tubes to attract and capture the paramagnetic macroscopic beads. The magnets may be applied, for example, for 120 seconds before the samples (which in this case may comprise concentrated nucleic acid) are aspirated from the ETU test tubes and transferred to respective wells in, for example, a 96-well sample plate 208. In another embodiment, which uses a 120-second clock cycle, the magnets may be applied for about 50 seconds. Complete sample transfer may be verified by ultrasonic measurement of the liquid level in the plate, as known in the art. Additional reagents or substances, such 20 ul of buffer solution and 45 ul of oil, may be added to each well in addition to each sample. Once the sample plate 208 is full, it is conveyed to the sample plate output 118 for eventual removal.

Any suitable device may be used to transfer the samples to the sample plate 208. For example one or more pipettors may be used to accomplish the final transfer of step 332. Examples of such devices are known in the art. In a preferred embodiment, however, a four-channel, fixed width pipettor may be used to aspirate samples from the eight ETU test tubes into a row of eight wells on a standard 96-well plate. This embodiment is described in more detail with reference to FIGS. 16-17B. Using this device, the pipettor secures new disposable pipette tips, aspirates samples from four adjacent ETU test tubes, dispense the samples into every other well along a row of a standard 96-well plate, then ejects the used pipette tips into the emptied ETU tubes. The pipettor repeats this operation for the remaining four ETU test tubes to fill all eight wells on the sample plate 208. This entire two-part operation is completed to fully process an ETU once every clock cycle. To provide some flexibility in when this process starts and stops, the final transfer station 242 may have multiple substations that each hold an ETU. This permits the final transfer step 332 to start and stop between system clock cycles.

The used pipettes and ETUs are transferred to a solid waste container 214. Ejecting the pipettes into the ETU test tubes decreases solid waste volume, and allows the system to operate for a greater intervals before emptying the solid waste output 214.

In the context of certain assays, the foregoing exemplary process and system is expected to permit sample throughput of up to about 1,400 patient samples per day, providing uncapping, a ten-step sample preparation process (beginning with the sample adequacy step), and output of purified DNA in a convenient 96-well format that can be processed in existing analytical equipment. The first group of samples (i.e., the first ETU full of samples) is processed about 50 minutes after starting the system, with additional ETUs completed in 2.5 minute intervals thereafter. Consequently, the first 96-well output plate is produced in about 77.5 minutes, with 30 minute intervals to complete subsequent plates. In other embodiments, the expected throughput of the system may be about 35 minutes to the completion of the first ETU with subsequent ETUs completed at about 2 minute intervals. This results in a time to complete the first 96-well plate is about 57 minutes and with every subsequent plate taking about 24 minutes to complete afterwards. Of course, the interval time and throughput rate will vary in other embodiments, depending on the number of processing steps, the sample processing volume (i.e., number of samples being processed at any given time), and so on.

It will be understood from the foregoing example that embodiments may provide a significant benefit by being adapted to perform multiple different assay protocols on samples. A random mix of such samples may even be provided on a single sample rack. During processing, the sample type may be identified by recognizing an identifying a characteristic of the sample container, reading an indicating feature on a barcode, or by other means. Alternatively, the type of samples on a rack may be mapped and associated with a barcode on the rack that is read when it is placed in the system, or a user may simply manually enter the sample types into the system. Regardless of the means for identifying the sample type, the system may be set up and programmed to process different types of samples according to different protocols, such as described above regarding the PC and Surepath protocols. As such, mixed groups of PreservCyt and SurePath samples can be simultaneously accommodated even in the same ETU. The system can automatically track which type of sample is in which position and can seamlessly accommodate the protocol differences (e.g., differences in quantity or type of reagent added). In the foregoing example, the clock cycle accommodates both protocols, and in other embodiments the clock cycle and processing steps can be modified to accommodate various protocols.

While the foregoing example requires little additional processing for the two protocols, in other embodiments, additional reagents and processing stations may be provided, if necessary, to provide the required disparate processing steps. In still other embodiments, it may be possible to modify the processing protocols of two different sample types to minimize or eliminate any disparate processing steps. For example, it may be possible to use a more similar or even identical protocols for PC and Surepath test samples, such as by pre-treating samples of one or both types at an early processing stage (e.g., by adding buffer to provide uniform processing volumes). Other variations will be apparent in view of the present disclosure. It will also be apparent that the nature of the particular reagents, buffers, test samples, and the like, will vary depending on the desired use of the particular embodiment, and the details of any particular protocol sought to be followed during processing. As such, an understanding of the exact nature of particular materials that may be used in exemplary embodiments is not believed to be necessary to facilitate or illuminate the understanding of the invention, and it is not necessary in this description to specifically identify such elements.

Exemplary Embodiments of Processing Equipment and Related Methods

As suggested above, it will be appreciated that any suitable machinery or equipment may be used to move the samples through the PAS 100 and its various processing steps. For example, the systems employed herein can use a variety of robotics known in the art to automate the movement of samples, reagents, and other system components. Exemplary robotic systems have capabilities to move samples on one, two, or three axes and/or to rotate samples about one, two, or three axes. Exemplary robotics move on a track which may be situated above, below, or beside the workpieces. Typically a robotic component includes a functional component, e.g., an arm able to grip and/or move a workpiece, insert a pipettor, dispense a reagent, aspirate, etc. Robotics may be translated on a track, e.g., on the top, bottom, or side of a work area, and/or may include articulating segments which allow the arm to reach different locations in the work area. Robotics may be driven by motors known in the art, which may be, for example electrically, pneumatically, or hydraulically powered. Any suitable drive control system may be used to control the robotics, such as standard PLC programming or other methods known in the art. Optionally the robotics include position feedback systems that optically or mechanically measure position and/or force, and allow the robot to be guided to a desired location. Optionally robotics also include position assurance mechanisms, such as mechanical stops, optical markers or laser guides, that allow particular positions to be repeatedly obtained.

In view of the present disclosure, the design of suitable embodiments is within the skills of the person of ordinary skill in the art without undue experimentation. Nevertheless, it has been found that various subsystems having particular designs may be used at various locations within the PAS 100 or other processing systems to provide suitable or improved operation. Examples of such systems are described below.

Exemplary Intake and Initial Transfer Equipment

Figure 4:
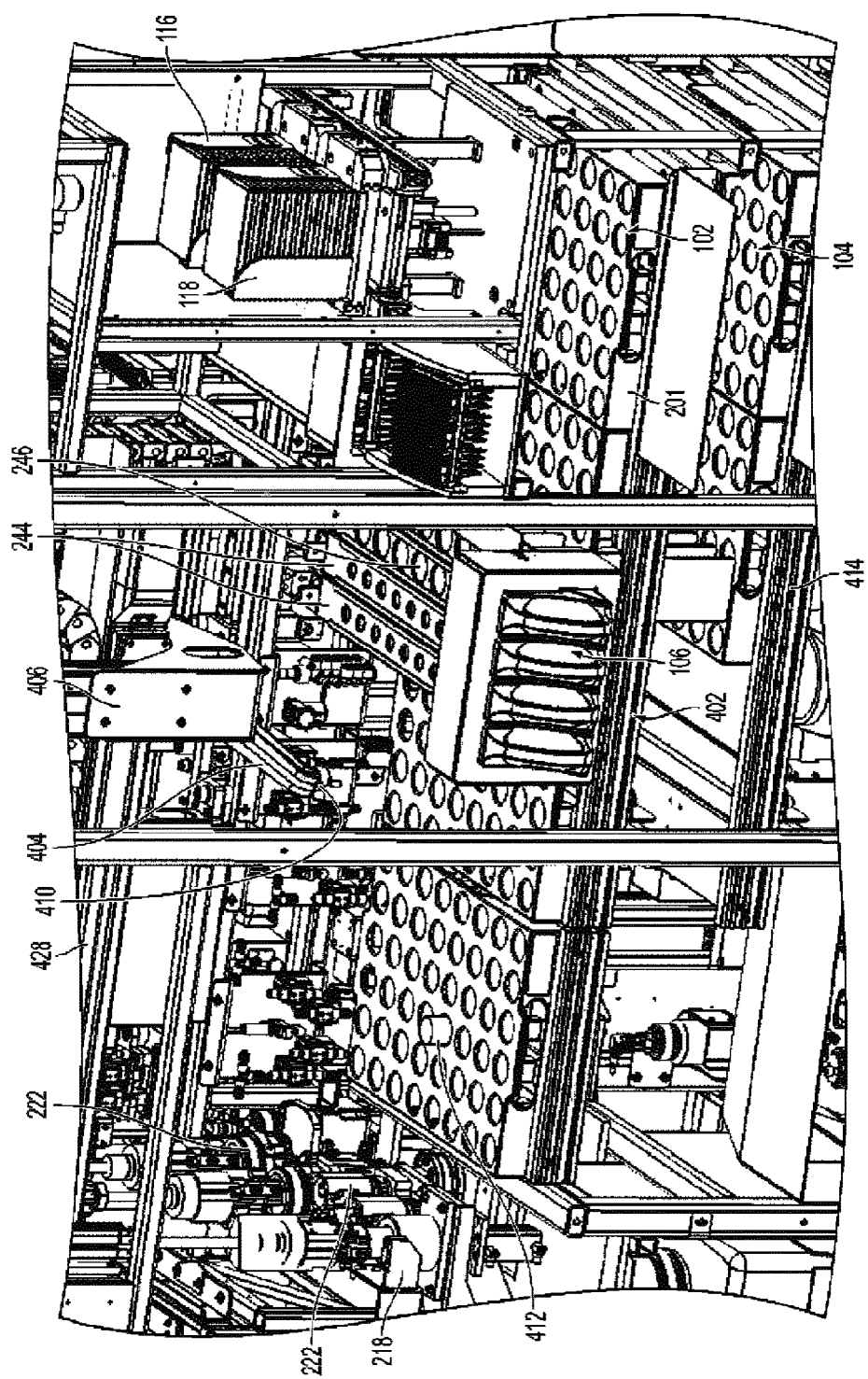
FIG. 4 is an isometric partial view of the sample intake and initial transfer area of the embodiment of FIG. 1.

FIG. 4 provides an isometric partial view of the sample intake and initial transfer area of the embodiment of FIG. 1. Here, it can be seen that the sample rack input 102 leads to a laterally-traversing track 402 upon which the sample racks 201 travel to the barcode reader 218, mixers 220 and decapper/capper unit 222. The sample rack 201 that is advanced furthest along the track 402 may be positioned on an elevator, such as a servo-operated counterweighted platform. Once all of the samples on the sample rack 201 have been processed, the elevator lowers the sample rack 201 to a lower laterally-traversing track 414 which conveys the sample racks 201 to the sample rack output 104. Any suitable conveyor, such as powered rollers, endless belts, robotic shuttle arms, and so on, may be used to move the racks 201 along the tracks 402, 414.

Two control sample racks 244 and two reject vial racks 246 are installed at the control vial and reject vial access point 106 located at the front of the device. These racks 244, 246 are mounted on corresponding tracks within the PAS 100. Suitable racks and tracks for this purpose are known in the art and need not be described here.

Figure 5:
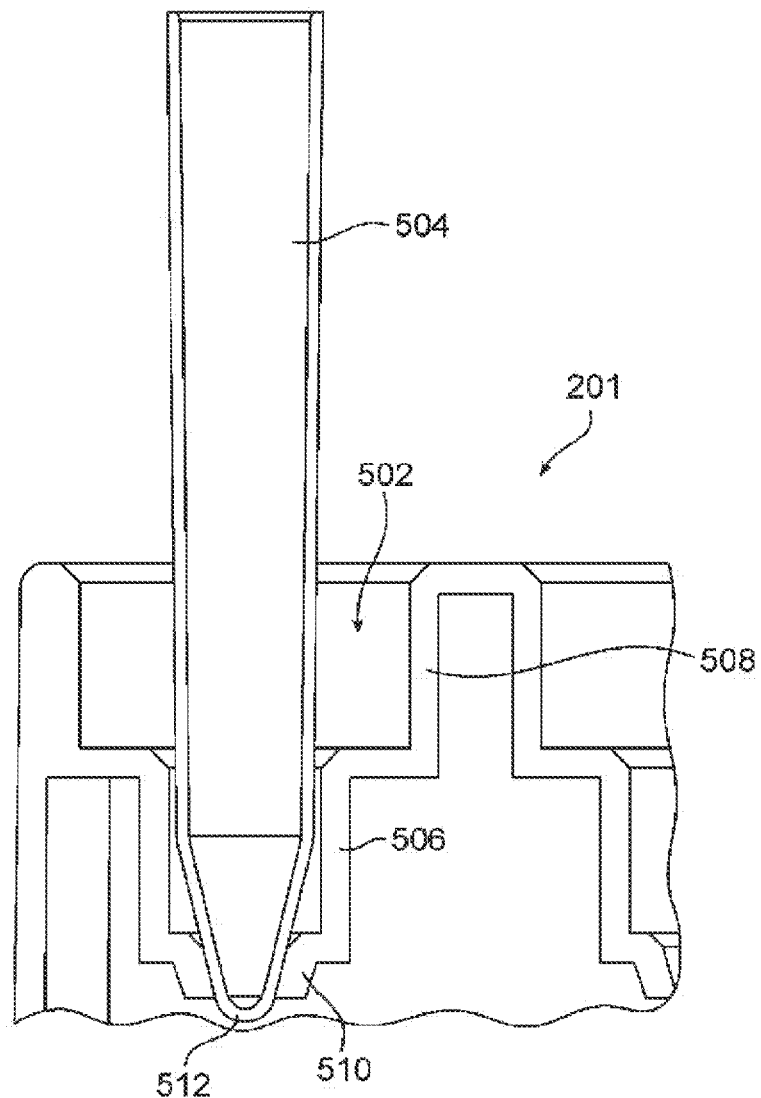
FIG. 5 is a cross-section side elevation view of a portion of an exemplary embodiment of a sample rack.

Referring to FIG. 5, the sample racks 201 may comprise any suitable rack having any number of sample holders 502. Each sample holder 502 may be adapted to hold sample bottles 504 of various different sizes. For example, each holder 502 may have a relatively small diameter at its lower end 506 that is adapted to hold smaller bottles 504, and a relatively large diameter at its upper end 508 to hold larger bottles (not shown). A depressed area or opening 510 may be provided at the bottom of the holder 502 to help center and hold bottles 504 having a pointed, rounded or conical end 512, such as the shown bottle 504.

Referring back to FIG. 4, an access arm 404 is pivotally and vertically mounted on a shuttle 406 that, in turn, is adapted to move laterally along an access arm track 408 located above the sample racks 201. By selectively rotating the access arm 404 about the shuttle 406, raising and lowering the access arm 404, and traversing the shuttle along the track 408, the access arm 404 can access to the all of the samples located on the sample rack 201 nearest the barcode reader 218. In addition, to provide continuous operation when the elevator is moving the racks down to the lower track for removal, the access arm 404 may be further adapted to access at least some of the samples located on the next sample rack 201. Any suitable drive mechanisms and control systems may be used to manipulate the access arm 404, and such devices are well known in the art and need not be described here. The access arm 404 may alternatively be replaced by a multi-pivot robotic arm the can access all of the necessary sample rack locations without requiring a moving shuttle. In other embodiments, the racks 201 may be moved to assist the access arm with picking up and depositing sample bottles 412. Other variations on an access arm 404 or other kinds of transfer mechanisms may be used in other embodiments.

At its distal end, the access arm 404 has a gripper 410 that is adapted to grasp and move sample bottles 412 having various sizes. The gripper includes a contact surface that transmits force to the sample bottle to control its positioning and movement. The gripper may include multiple elements that apply differential forces to the sample bottle. For example, one element may hold the bottle body, and another may hold the bottle's lid and apply a force to remove it. Many different grippers are well known in the art and may be used within the spirit and scope of the present disclosure; accordingly the following descriptions of exemplary grippers should be understood to be illustrative, rather than limiting. In the shown example, the gripper 410 may comprise an expandable chuck or finger-style having a jaws that accommodate generally circular sample bottles 412. The jaws may be stepped to grasp bottles having different diameters at each step location. One or more of the jaws may be moveable such as by being pneumatically actuated, hydraulically actuated, driven by a motor, or being coupled to a spring or a flexible material. The movement may be translational and/or pivoting. An example of another suitable gripper is provided in U.S. Patent Publication No. 2008/0247914, which is incorporated herein by reference.

Other suitable grippers maybe used as well. For example, a bellows gripper may be used, or a strap gripper may be used (i.e., a grippers having a flexible material, such as metal, leather, rubber, plastic, etc., forming a loop that is tightened around a workpiece). A suction cup gripper may be used as well. Suction cup grippers have a contact surface able to form an air-tight seal against a workpiece, allowing the workpiece to be held by a vacuum. A vacuum seal may be formed by evacuating air (using a pump or by pressing the suction cup against the workpiece) out of a chamber defined by the workpiece surface and the gripper surface. Alternatively, or in addition, the volume of the chamber may be increased by applying a force that pulls the gripper surface, also resulting in partial vacuum. Once a partial vacuum is established, the workpiece is held against the gripper by atmospheric pressure. The workpiece may then be released by restoring ambient pressure within the chamber, which breaks the seal, such as by opening of a passage through the gripper, deformation of the contact surface between the gripper and workpiece, or allowing air or another fluid to pass out of or through the workpiece into the chamber. A magnetic gripper also may be used. Magnetic grippers include a magnetized portion able to apply force to a workpiece. The magnetic force may be controllably released, for example by use of an electromagnet that is turned on and off, and/or by having a magnetized portion that is able to move relative to a contact surface, such that the magnetized portion can be moved away from a workpiece to facilitate release. Alternatively, a magnetic gripper may release a workpiece by having the workpiece grabbed by another gripper, whereby the workpiece is released when the magnetic gripper is withdrawn.

The access arm 404 is programmed to remove each sample bottle 412 from the sample rack 201, place the bottle 412 in the barcode reader 218, remove the bottle 412 from the barcode reader 218 after a sample is taken, and return the bottle 412 to the location on the rack 201 from which it was taken. In addition, the access arm 404 may be adapted to remove control samples from the control sample racks 244, and place rejected samples on the reject vial racks 246.

Exemplary DCU Equipment

Figure 6B:
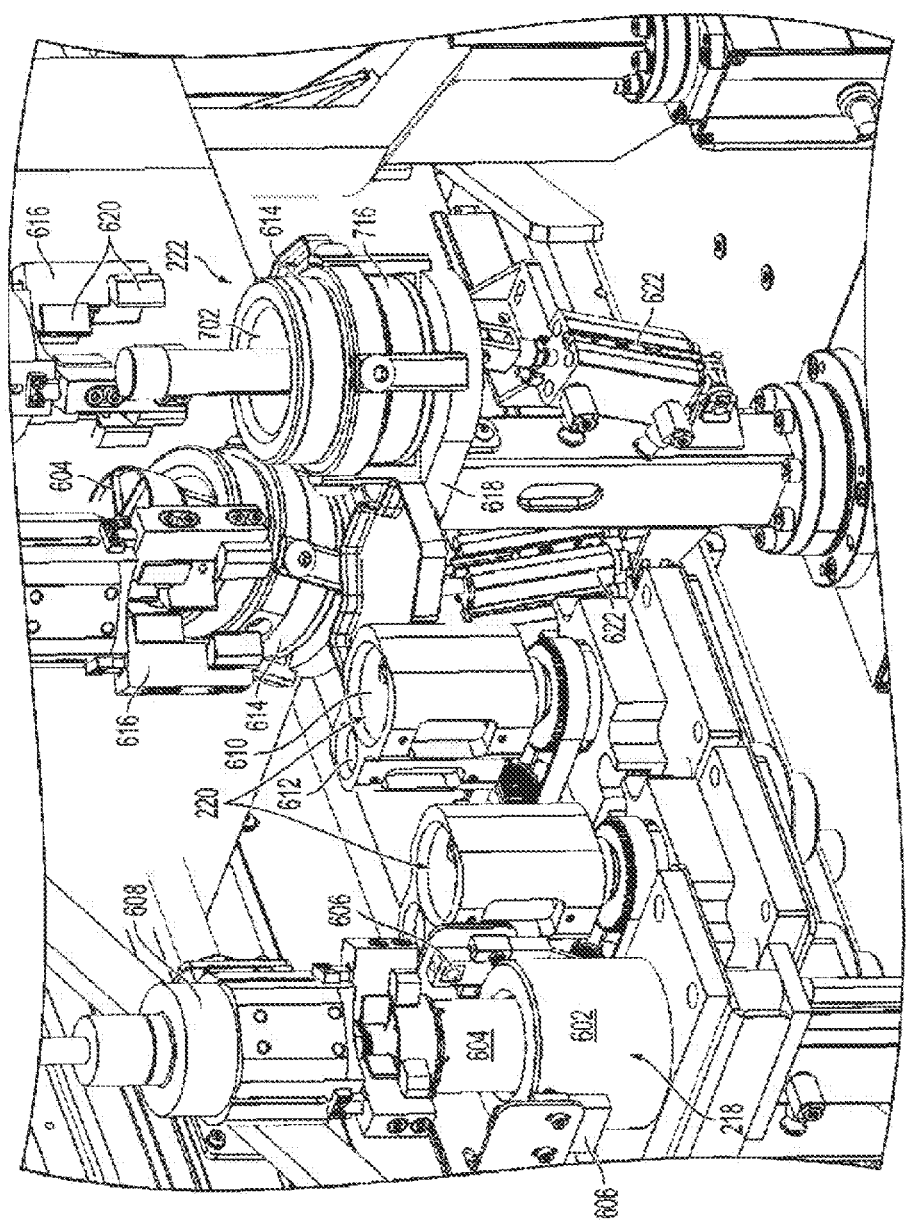

FIGS. 6A and 6B illustrate an exemplary barcode reader 218, shaker unit 220 and decapper/capper unit 222 in greater detail. Collectively, these are referred to herein as the "DCU," but a DCU may also comprise only some of these elements and/or other elements. The DCU may be used according to the processes described herein, or in other ways, to provide high volume processing of specimens in various contexts and to reduce the need to rely on labor intensive processes that may subject personnel to exposure to samples and repetitive motion injuries. For example, the DCU may be used as an open platform system that can be integrated into various processing systems, or used as a separate self-contained unit. Various applications exist for a DCU such as the ones described herein, and particular application may be found in liquid cytology processes, such processing cervical specimens, PAP smear testing, HPV DNA testing, and so on.

Figure 7B:
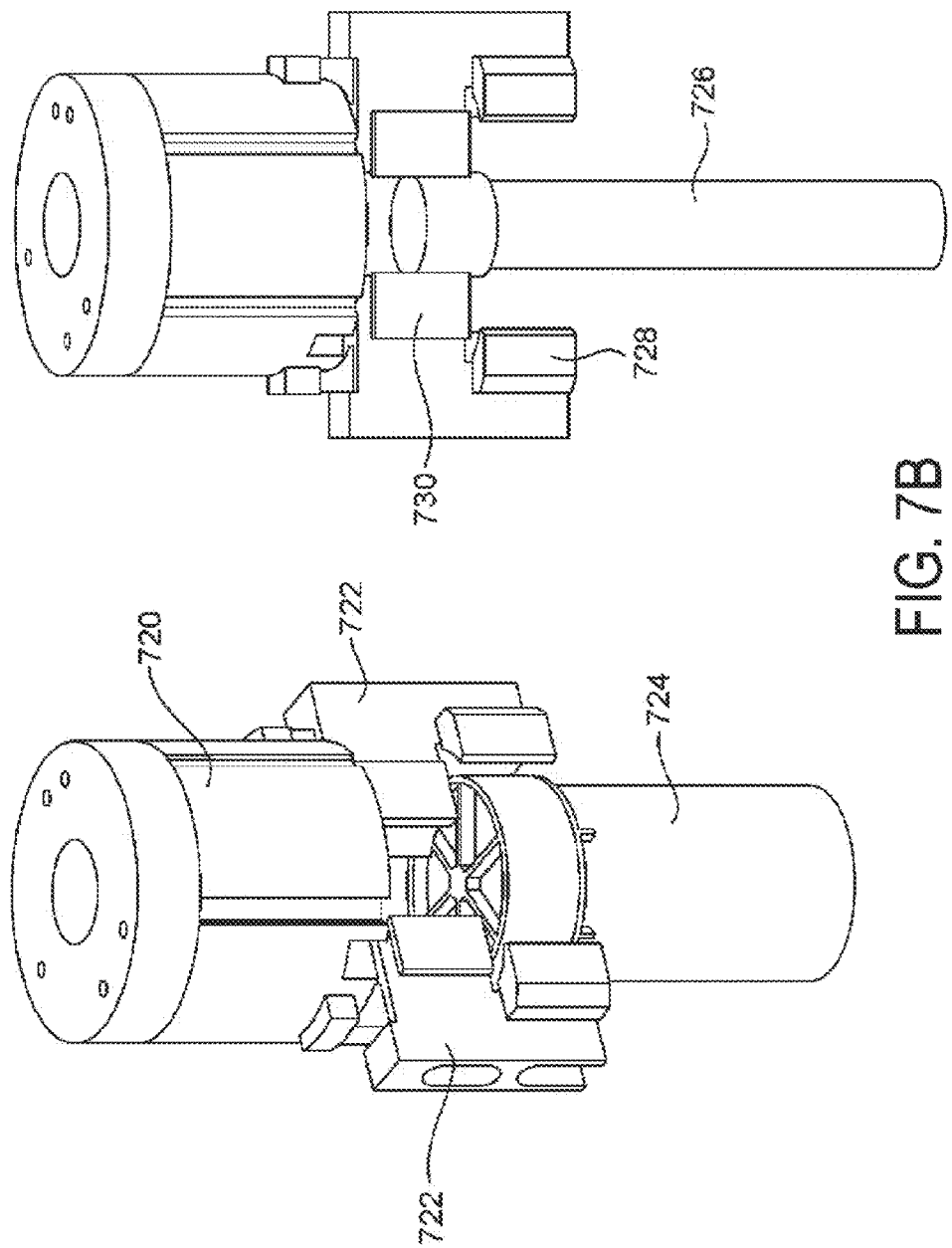
FIG. 7B is an isometric view of an exemplary gripper that may be used with a DCU, shown addressing two different size bottles.

In the exemplary embodiment, a barcode reader 218 may comprise a cylindrical chamber 602 into which an access arm or other device inserts a sample bottle 604. The chamber 602 may be adapted to hold various different types of sample bottles 604, such as discussed elsewhere herein. One or more barcode scanners 606 are provided around the periphery of the barcode reader 218. the chamber 602 may be adapted to rotate to bring a barcode on the bottle 604 into view of one or both scanners 606 to read the code. In other embodiments, a transport arm 608 may be used to hold and rotate the bottle 604. The transport arm 608 may comprise any suitable gripper and drive mechanisms, and may be adapted to convey the bottle 604 to the shaker unit 220 and/or decapper/capper unit 222. An example of a suitable transport arm gripper is shown in FIG. 7B, which illustrates a chuck 720 having two jaws 722 mounted to it. The chuck 720 is mounted on a spindle and driven by a suitable motor to rotate it. The jaws 722 are adapted to move radially in an out relative to the rotating axis of the chuck 720 in order to grip the bottles 724, 726, although in other embodiments other gripping movements may be used, as known in the art. As shown in the two illustrations, at least two different size bottles 724, 726 may be manipulated by the chuck 720. This may be facilitated by providing the jaws 722 with steps 728, 730 that correspond to different bottle sizes, such as shown. In other embodiments, different bottle sizes may be accommodated by providing the jaws 722 with a large range of travel, or by other means. While the shown barcode reader 218 may be suitable in some embodiments, it will be appreciated that it may be moved or replaced by a barcode reader mounted on an access arm that loads samples directly into the shaker unit 220 or decapper/capper unit 222. A reader also may be placed in other locations, such as described elsewhere herein.

Figure 7C:
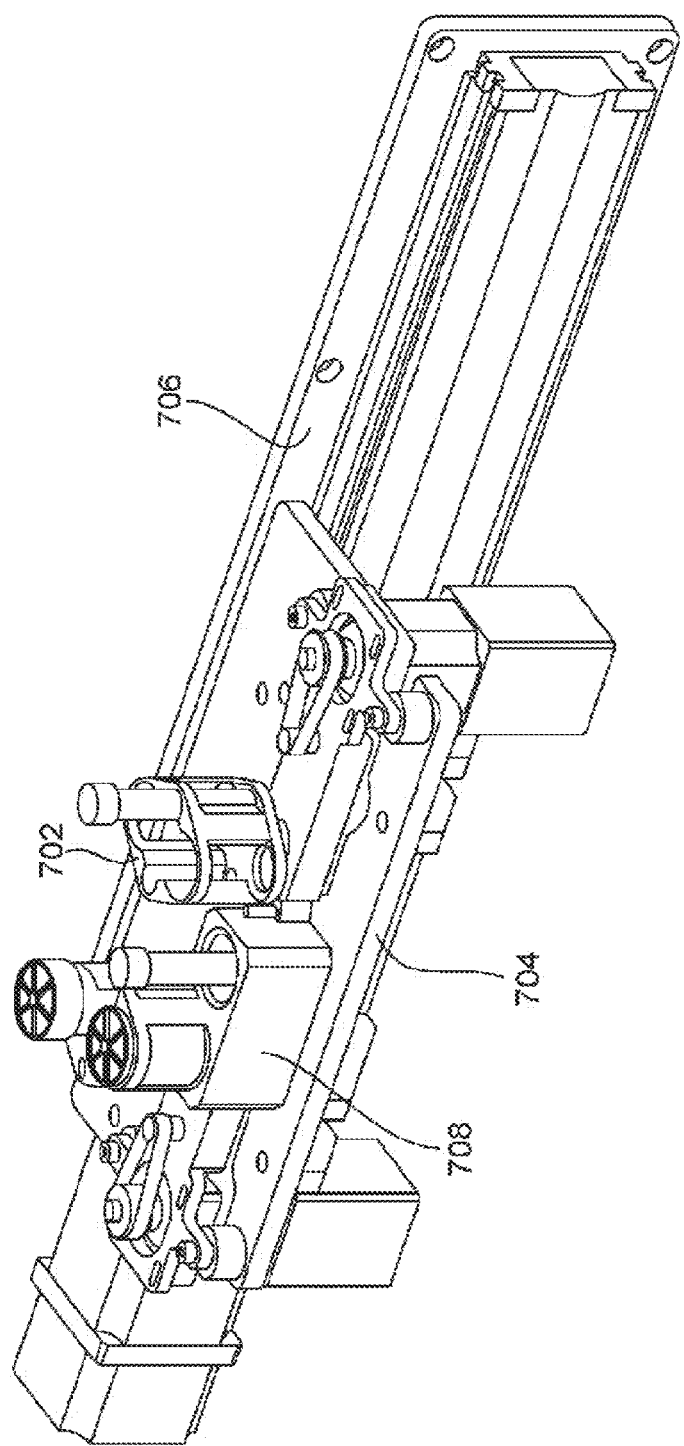
FIG. 7C is an isometric view of an exemplary combined shaker and transport mechanism.

The shaker unit 220 may comprise any suitable arrangement of one or more sample mixers. Such devices are typically operated by an offset drive system or other mechanism, and are generally well-known in the art. In the shown embodiment, two shakers are provided in the shaker unit 220. Each shaker comprises a pair of adjacent cylindrical chambers 610, 612, each of which is adapted to hold bottles having one or more different sizes. In one embodiment, shown in FIG. 7C, the a pair of shakers 702 may be mounted on a platform 704 that is adapted to move along a track 706 before, after or during the shaking operation. These shakers 702 may include multiple joined chambers for holding different size bottles. In addition, an idle holding chamber 708 that does not shake, but is associated with the DCU and used to hold one or more sample bottles at intermediate transport stages may be provided on the platform 704 or elsewhere in this or other embodiments.

The decapper/capper unit 222 is located adjacent the shaker unit 220. The exemplary decapper/capper unit 222 comprises two bottle grips 614 that are adapted to hold the bottoms of the sample bottles 604 (preferably regardless of the size or shape), and two cap grips 616 that are adapted to grip and turn the bottles' caps. The bottle grips 614 may be mounted on a rotating platform 618, the purpose of which is described below. Referring to FIG. 7A, and exemplary bottle grip 614 may comprise a bellows grip. The bellows grippers are pneumatically or hydraulically actuated devices that have an inflatable bladder 712 that can be inflated to press into contact with the bottle 604. The bladder 712 is shaped generally like a cylinder, torus, or elongated torus, and is located inside a rigid cylinder 716 against which it presses to generate a griping force when it is inflated. In other embodiments, the bladder 712 may have other shapes, and may operate by pressing the bottle 604 against a stationary surface or by other means. The bladder 712 may be made of any material able to expand when the actuating substance is pressurized, such as rubber, plastic, or other elastomeric material. The bladder's surface may be used to contact and grip the bottle 604.

In the shown exemplary embodiment, a number of ribs 714 are disposed at various locations around the inner circumference of the bladder 712 and secured to the bladder 712 by adhesives, stitches, or other means. The ribs 714 are believed to help orient the bottle 604 in an upright orientation, and may improve grip on the bottle 604. The ribs 714 may help grip different size bottles, but it also may be desirable in other embodiments to remove the ribs to possibly facilitate a larger range of bottle sizes. The ribs 714 may be smooth rods, or they may be treated to increase their frictional contact with the bottle. Even with the ribs 714 present, some of the bladder's surface may still contact the bottle 604 when the bladder is inflated. The bladder 712 may include other features in other embodiments. For example, the bladder 712 may have circumferential steps to help center and hold different size sample bottles 604. While the foregoing bellows grips 614 may be preferred in some embodiments, other grips, such as expanding chucks or jaws, strap grips, and the like, may be used in other embodiments.

As noted above, the decapper/capper unit 222 also includes a pair of cap grips 616. The cap grips may comprise any suitable mechanism having a grip to hold the appropriate size bottle caps, and a drive mechanism to rotate the grip. The cap grips 616 also may have a vertical movement component to raise them and lower them as needed to grasp and remove the bottle caps. An embodiment of such a grip is discussed above with respect to FIG. 7B. Of course, other designs may be used in other embodiments, such as those described elsewhere herein or as known in the art. For example, the embodiments of FIGS. 6A and 6B are similar to that shown in FIG. 7B, but may use three stepped jaws 620 instead of two. The cap grips 616 may be mounted on a traversing arm or a rack so that they can be moved laterally. In such an embodiment, the cap grips 616 may be used to pick up bottles from the shaker unit 220 and move them to the bottle grips 614.

In use, a transfer mechanism, which may be the transport arm 608 used to rotate the bottles in the barcode reader 218 or some other mechanism, such as the cap grips 616, conveys bottles to the bottle grips 614 and lowers them into place. The bellows in the bottle grips 614 preferably are inflated before the transfer mechanism lets go of the bottle 604, to thereby expand the bladder 712 and securely hold the bottle 604 centered in the bellows. This centering action helps ensure that the bottles are centered and that the cap grips 616 will be able to effectively grasp the bottle caps. The bellows is kept inflated to ensure that proper alignment is retained during subsequent steps and until recapping is completed. Each bellows 614 preferably may be independently inflated, but this is not strictly necessary.

During uncapping, the bottle grip 614 holds the bottom of the bottle 604, and the cap grip 616 holds the bottle cap. The cap grip 616 is rotated and uncapping can be detected by measuring displacement as a function of time, with a screw cap being fully unscrewed when the displacement no longer increases with further rotation. At this point the cap gripper 616 may be actively raised to clear the rest of the bottle 604. Uncapping can also be performed by applying an upward force that immediately separates the base and cap once the threads are no longer engaged. Screw caps on cervical sample bottles such as those used on standard SurePath or PreservCyt® vials can be uncapped using these or other methods. Where the cap grip 616 must accommodate caps of different sizes and bottles of different lengths, the cap grip 616 may be controlled in any suitable way. In one embodiment, in which two bottles are addressed, with one being taller and narrower and the other being shorter and wider, the difference in shape can be accounted for simply by making the cap grip 616 jaws stepped to hold the tall, narrow bottle at an upper location, and the wide, short bottle at a lower location. the embodiment of FIGS. 6A and 6B may provide this functionality.

Recapping is accomplished essentially by reversing the steps of uncapping. Preferably the base of the opening of the cap is slightly wider than the top of the bottle such that alignment is simplified. Alignment of the base and cap may be assisted or accomplished by sensors (e.g., optical or ultrasonic sensors that directly or indirectly determine the position of the base or cap) or by controlling the positions of the grips 614, 616 using accurate motion control mechanisms such as stepper motors or servos.

While the shown embodiments generally refer to decapping and capping operations for threaded twist-off caps, it will be understood that, in other embodiments, the DCU may be adapted to perform these operations on pushcaps instead of or in addition to threaded caps. In such an embodiment, the grips 614, 616 may be adapted to apply a force to pull the cap off a bottle. Such modifications should be apparent based on the present disclosure. Exemplary embodiments of such pushcaps are found, for example, in U.S. Application No. 61/272,603, entitled "Closure and Method of Using Same" and filed on Oct. 9, 2009, which is incorporated herein by reference in its entirety.

As noted above, the decapper/capper unit 222 may be mounted on a rotating platform 618. The platform 618 may be rotated as needed by any suitable drive mechanism and control system. As explained in more detail in the below exemplary process examples, the platform 618 may be rotated to positioned the bottles contained in the bottle grips 614 at various locations for various processing steps. For example, the platform may be rotated 90 degrees to locate a bottle at a pipetting station where an pipette is used to aspirate a sample from the bottle. The decapper/capper unit 222 is shown in the decapping (and capping)-position in FIG. 6A, and in the aspirating position in FIG. 6B.

To avoid crashing the pipette tip into the bottom of a tube, aspiration may take place with a pipette at some distance from the bottom of a tube. Samples may be provided in a flat-bottom bottle or tube or other configuration from which it is difficult to automatically pipette the entire sample, resulting in a high dead volume. In an exemplary embodiment, the input sample bottle 604 may be tilted (for example, held at an angle between about 15 and 20 degrees from vertical) during pipetting, such that dead volume is reduced by causing the sample to collect at the lowered part of the tube. For example, pipetting may be performed with the pipette tip approximately 1 millimeter from the bottom of a standard PreservCyt vial, resulting in approximately 1 mL of dead volume due to the flat tube bottom. By tipping the vial, the same approximately 1 mm separation between pipette tip and the bottom of the tube results in a dead volume of only approximately 0.1 mL. Thus, tipping allows approximately 0.9 mL of additional sample volume to be recovered. As the required assay volume typically is only a few milliliters (depending on the particular assay performed), increased recovery of an additional 0.9 mL can greatly decrease the fraction of samples that might otherwise be rejected (or require manual intervention) due to insufficient volume.

Tipping can be accomplished by standard methods known in the art. In the shown embodiment, the bottle grips 614 are mounted on hinged portions of the rotating platform 618. Pneumatic linkages 622 are connected to platform 618, and adapted to raise the platform 618 at the pipetting station, such as shown in FIG. 6B. When tilting is not required, the hinged portions of the platform may be held in a horizontal position be the linkages 622 or simply by gravity. Just prior to pipetting, the pneumatic linkage is activated to tilt the platform 618, grip 614, and bottle 604.

Figure 7D:
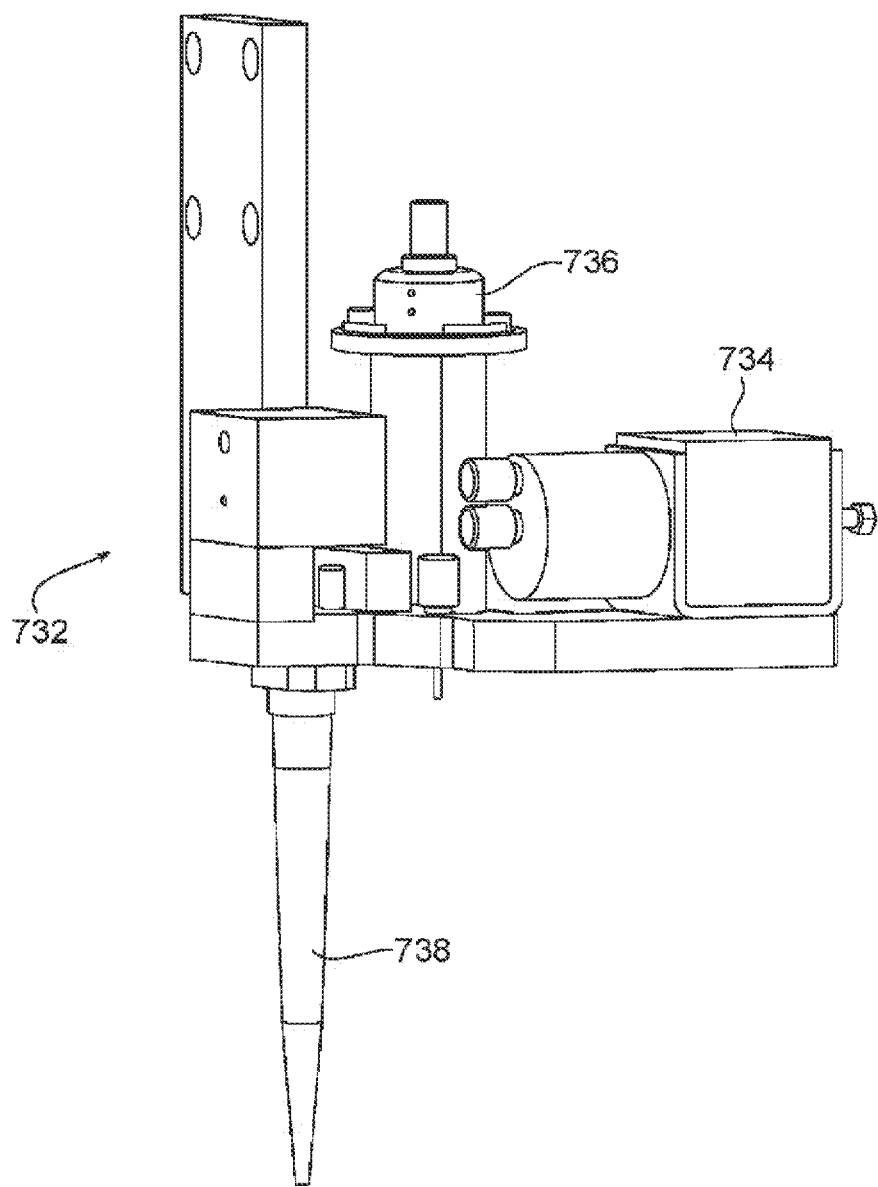
FIG. 7D is an isometric view of an exemplary combined aspirator/reagent pump.

The decapper/capper unit 222 may be provided with other features and functions. For example, a process flow may be used to ensure that only one input sample container is opened at any given time to minimize the risk of cross-contamination or of inadvertent mis-placement of a cap on a different input sample container than its original input sample container. Also, the pipette that aspirates the sample from the bottle 604 may be adapted to add an additional reagent to the bottle. An example of such a pipette is shown in FIG. 7D. Here, a standard pipettor (e.g., a 5 ml pipettor) has been modified to include an integral reagent dispensing pump 734 (e.g., a Z-series pump available from Tricontinent Scientific, Inc. or Grass Valley, Calif.). A pneumatic cylinder 736 is also provided to eject used pipette tips 738.

Exemplary Open Platform DCU ("DCU-OP")

As noted above, in one embodiment, a DCU may be provided in an open-platform format. For ease of reference, an open platform DCU is referred to herein as a "DCU-OP." A DCU-OP may be desirable, for example, where it is desired to pre-process a large number of samples for later testing, but the pre-processing steps generally do not include intensive sample processing steps such as incubation and multiple aspirations. A DCU-OP also may be desirable, even in relatively low-volume applications, where it is desired to avoid direct exposure to a sample or to reduce ergonomic hazards such as repetitive stress disorders.

A DCU-OP may be controlled as described above with respect to the PAS 100, or using any other suitable means. In one embodiment, a DCU-OP may be controlled by a computer running software and having a graphical user interface, touch screen, keyboard, barcode scanner, mouse, or other features. Data may be transferred between the DCU and the computer or other devices by any suitable means, such as flash drives, direct connection, wireless connection, and so on.

A DCU-OP preferably may be operated continuously or as a batch mode device. Samples and materials may be provided to the DCU-OP using mechanisms like those described above (e.g., sample rack, ETU rack, access arm, etc.), but other systems, including manual operation, may used in other embodiments. Output may be to ETUs or other sample racks. Examples of standard output racks (which also may be used in other embodiments described herein) include QIAsymphony racks and MST vortexer racks. A specific rack also may be developed for the DCU-OP system, or the system may be adapted to use any suitable generic rack.

A DCU-OP may be operated in any suitable way. For example, in one embodiment, a DCU-OP may be operated by powering on the machine, selecting the appropriate output tube type from a list of supported tube types, and selecting an output rack type from a list of supported output rack types. In order to provide broad open platform capabilities, the system may include an extensive library of suitable input and output sample formats. The DCU-OP input and rack handling system may be adapted to handle sample holding racks that hold numerous sample formats (e.g., cervical sample tubes, urine tubes, blood tubes, etc.), as well as additional alternative racks to hold other formats. To provide even greater flexibility, the DCU-OP may be programmed to permit a user to enter input tube, input rack, or output rack dimensions, such as height, diameter, width, length, sample spacing, well locations and dimensions, and so on, and the machine may use this input to calculate appropriate algorithms for finding and manipulating samples.

The operator may create matching barcodes for input and output tubes, and then label the tubes. The input tubes or samples may then be scanned and placed in a rack in an order specified by the software (the rack also may be specified by the software), so that the software has an accurate map of the rack contents. The output tubes also may be scanned and placed in a rack in an order specified by the software. These steps may help ensure that the software has an accurate map of the rack contents. The loaded racks may then be placed in the DCU-OP, along with any necessary reagents and consumables, such as pipette tips. Before a run begins, the operator also may empty the solid and liquid waster containers. The operator also may enter values for reagent deposition volumes, mixing times, sample volumes, and so on. After preparations are complete, the operator initiates a processing run, and may monitor the run, review the run report, and edit, save and print the report as necessary. The report also may be automatically saved and transmitted to other processing stations, such as a sample analyzer into which the processes samples are eventually loaded or a central control unit that communicates with the DCU-OP and the analyzer.

During the run, the DCU-OP may use a PLC controller or other control logic to select and use sensors that monitor some or all of the processing steps to assure quality control and correct handling of the samples. Any suitable barcode or other sensor may be used to assist with this monitoring. Anomalies in the workflow or scans may be reported and traced as well. These features are of particular interest in clinical markets, in which control and monitoring of samples assures correct diagnosis or health status reporting of patients.

Figure 26:
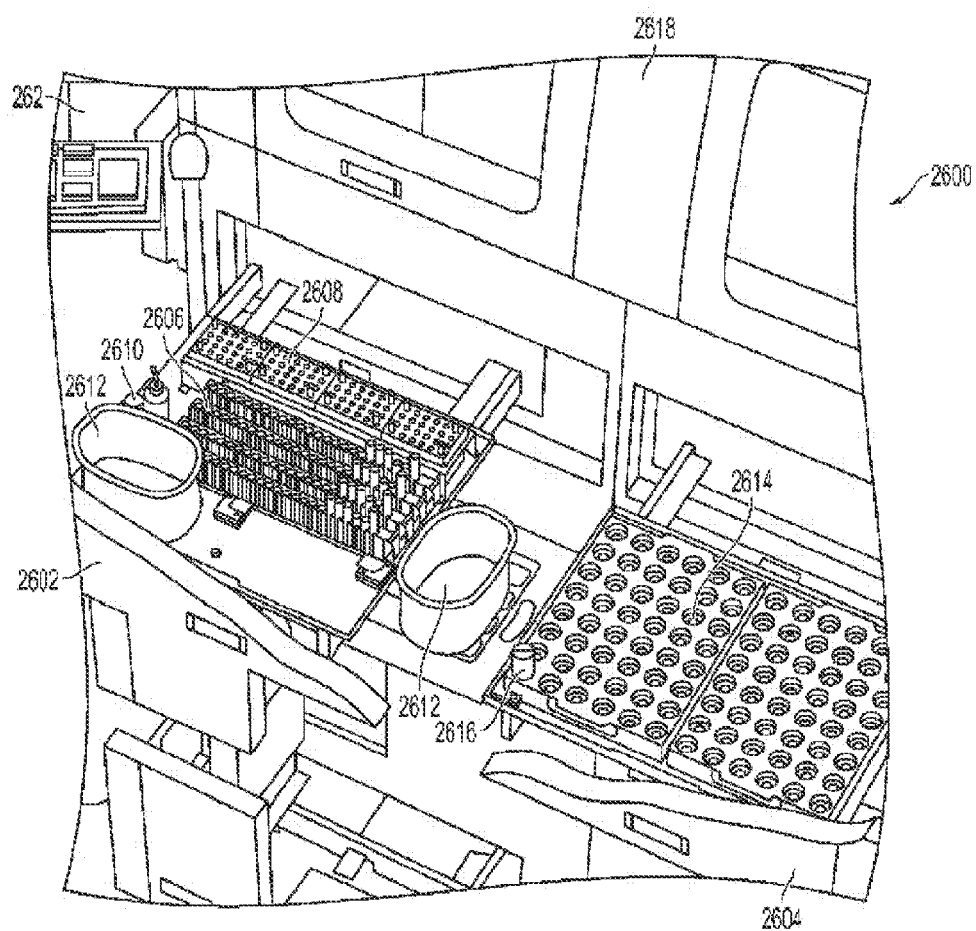
FIG. 26 is a partial isometric view of an exemplary embodiment of an open platform DCU.

FIG. 26 illustrates an exemplary embodiment of a DCU-OP 2600. Here, the DCU-OP includes two loading racks 2602, 2604. The left rack 2602 holds pipette tips 2606 and output trays 2608, reagent bottles 2610, and a solid and liquid waste containers 2612. The right tray 2604 holds sample racks 2614, each of which holds a number of bottles 2616 (e.g., Preservcyt™ sample bottles available from Hologic, Inc of Bedford Mass.). The trays 2602, 2604 are slid into place in the DCU-OP housing 2618 for operation. An associated computer 2620 may be provided adjacent to the housing 2618. Preferably, the racks 2602, 2604 are configured to allow manual scanning operations to occur as the various components are loaded in them, and they may be arranged to be at about the same height as a standard lab bench or cart to assist with scanning and loading. If desired, the entire DCU-OP may be mounted on wheels to be movable.

While the DCU-OP may output samples to ETUs or sample plates such as 96-well plates, it also may be adapted to output samples to individual test tubes. Examples of output tubes include: 15 mL vials having conical bottoms, threaded tops, a diameter of 17 mm and a length of 118 mm; 10 mL vials having round internal bottom ends, threaded tops, a diameter of 16 mm and a length of 79 mm; 14 mL vials having round bottom ends, flanged tops, a diameter of 17 mm and a length of 100 mm; 10 mL vials having round bottom ends, unthreaded tops, a diameter of 16 mm and a length of 100 mm; 9 mL vials having round bottom ends, unthreaded tops, a diameter of 13 mm and a length of 100 mm; and 4 mL vials having round bottom ends, threaded tops, a diameter of 15 mm and a length of 75 mm. Preferably, a DCU-OP can be configured to process all of these different output vial types, and may be able to process more than one output vial type in a single operation run. Of course, embodiments of other systems described herein, such as the PAS 100, also may output to individual tubes such as those describe above or constructed otherwise.

During operation, the DCU-OP may perform any of the processes described herein, and may perform other processes as well.

Exemplary DCU Process Flow

Figure 8:
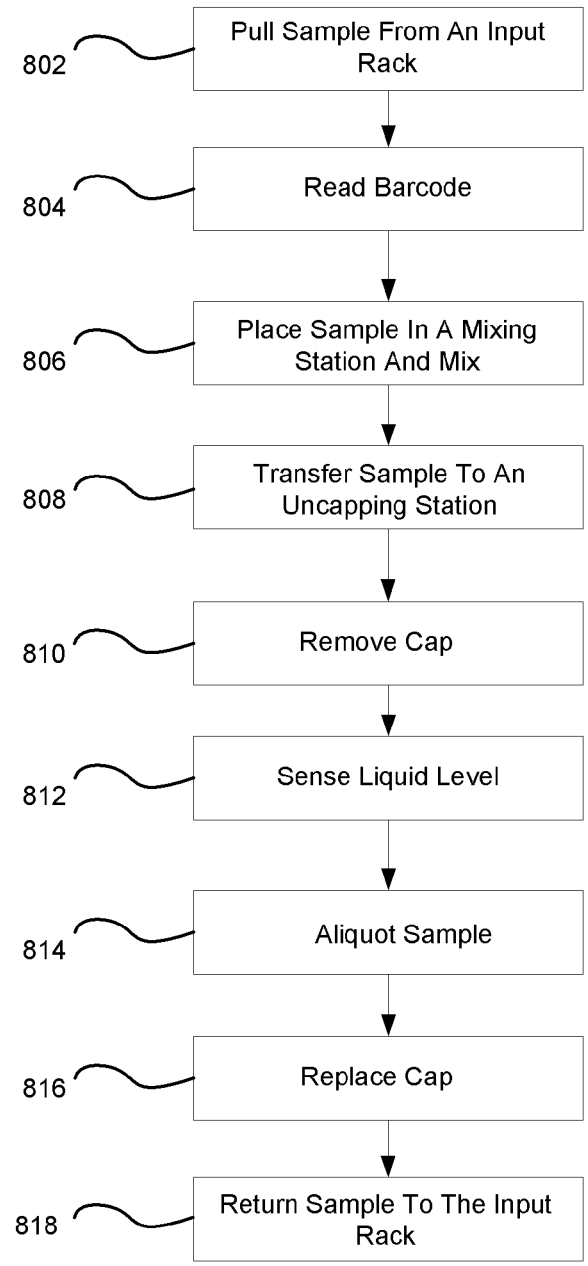
FIG. 8 is a schematic diagram of a DCU flowpath.

FIG. 8 illustrates a process flow for extracting and processing a sample container. This process may be used by the DCUs or DCU-OPs described above or other systems. In this exemplary embodiment, the sample is accessed and transferring the sample to an output container. Many variations and arrangements of the process may be made. For example, a sample adequacy determination may be made using techniques known in the art or described or referenced elsewhere herein. Although FIG. 8 depicts a process flow for a single sample container it should be understood that in some embodiments, different sample containers may be processed concurrently. In these embodiments, one or more secondary sample containers may be processed during the processing of a first sample. Redundant components or components with capacity to handle a plurality of samples may be used to facilitate concurrent processing of samples and to increase sample processing throughput. For example, a mixing station may contain a plurality of mixers which may allow a plurality of samples to be mixed concurrently. An uncapping and recapping station may also contain a plurality of grippers and uncappers. Processes that handle multiple samples concurrently may take one or more precautions to prevent sample contamination. For example, the system may be operated such that only one sample is uncapped at any time. Furthermore, a cap from a sample container may not be released from the sample container or otherwise put in contact with a surface other than the corresponding sample container.

Returning to the exemplary process of FIG. 8, the process may begin at step 802. At step 802, a sample container may be pulled from an input rack by and transfer arm having a gripper adapted to hold the sample container. The transfer arm may be capable of moving on one, two, or three axes, and may be operated by any suitable electric, hydraulic, pneumatic or other actuators. Components of an transfer arm may provide further positioning and sample manipulation capabilities (e.g., a gripper may be capable of rotating or tilting a sample). An input rack may be of one or more standard sizes, and may hold samples of various sizes.

The size of an input rack and the size and coordinates of one or more sample containers associated with the rack may be known or determined by a processor communicatively coupled to the transfer arm, as known in the art. According to some embodiments, the transfer arm may contain additional sensors to facilitate positioning of an the gripper to retrieve the sample container. Such sensors may include, but are not limited to, optical sensors, ultrasonic sensors, and pressure sensors. Position assurance systems such as, for example, mechanical stops, may also be used. Once the transfer arm is located over a desired sample, the gripper may be used to retrieve the sample.

At step 804 of the exemplary process, a barcode may be read, an RFID tag may be detected or other methods may be performed to verify the identity of a retrieved sample container. The transfer arm retrieving the sample container may contain a barcode reader or it may pass the sample container in front of a barcode reader. In such embodiments, the gripper may be configured with a rotating head that can rotate the sample container in front of the barcode reader, wherever it is positioned, to facilitate barcode scanning. In this way, barcode scanning may be performed in transit from an input sample rack to a desired location. The barcode reader also may comprise a separate station in which the sample container is placed, such as described above.

At step 806 a sample may be placed in a mixing station. A mixing station may contain one or more mechanisms for mixing or agitating a sample (e.g., an orbital mixer). A mixing station may be of a known location so that a processor communicatively coupled to an transfer arm may provide coordinates to an transfer arm. A mixing station may contain one or more mixers or agitators capable of receiving a sample container. Mixing times may be specified by a process communicatively coupled with the mixing station or may preset at a component of the mixing station.

According to some embodiments, a mixing or agitating apparatus may be incorporated into an transfer arm so that a sample may be mixed during transit. In these embodiments, transfer to a mixing station may not be necessary and a sample may be placed in an uncapping station after retrieval from an input tray.

At step 808, after completion of mixing, a sample may be transferred to an uncapping station. According to some embodiments, transfer from a mixing station may be performed by a second transfer arm which may be separate from and operate independently of a transfer arm retrieving samples from an input tray. According to other embodiments, the same transfer arm may retrieve samples from an input tray and place samples in an uncapping station.

An uncapping station may contain one or more grippers for receiving, holding, and releasing a sample container. An uncapping station may also contain one or more uncappers. An uncapping station may be capable of rotating a received sample between two or more positions. For example, a first position may be used for receiving a sample from a transfer arm, a second position may be located beneath a first uncapper, a third position may be used for pipetting or otherwise accessing a sample, and a fourth position may be located beneath a second uncapper. After receiving a sample from a transfer arm, an uncapping station may rotate or otherwise transport the sample beneath an uncapper.

At step 810, the sample container cap may be removed. After removal of the sample cap, the sample may be rotated or otherwise transported to a position for sample access. The position may be accessible by a pipetting arm.

Prior to pipetting one or more additional steps may be performed. At step 812, a liquid level in a sample container may be sensed. The liquid level in a sample vial is optionally sensed (e.g., with an optical, ultrasonic, or mass-based sensor, or by measuring the liquid volume pipetted from the vial) to determine whether tilting is required to obtain the desired sample volume and/or to ensure that the sample volume is low enough to permit tilting to a given angle without causing a spill.

At step 814, the sample may be aliquoted by a pipetting arm. The aliquoted sample may be transferred to an output container (e.g., an open position on an ETU).

After the sample has been withdrawn, the uncapping station may rotate the sample under the same uncapper that removed that sample cap. At step 816, the sample container may be recapped by essentially reversing the same steps used for uncapping.

After recapping, the uncapping station may rotate the sample to a position accessible by a transfer arm for return to the input rack. At step 818, the sample may be returned to the input rack.

Figure 9A:
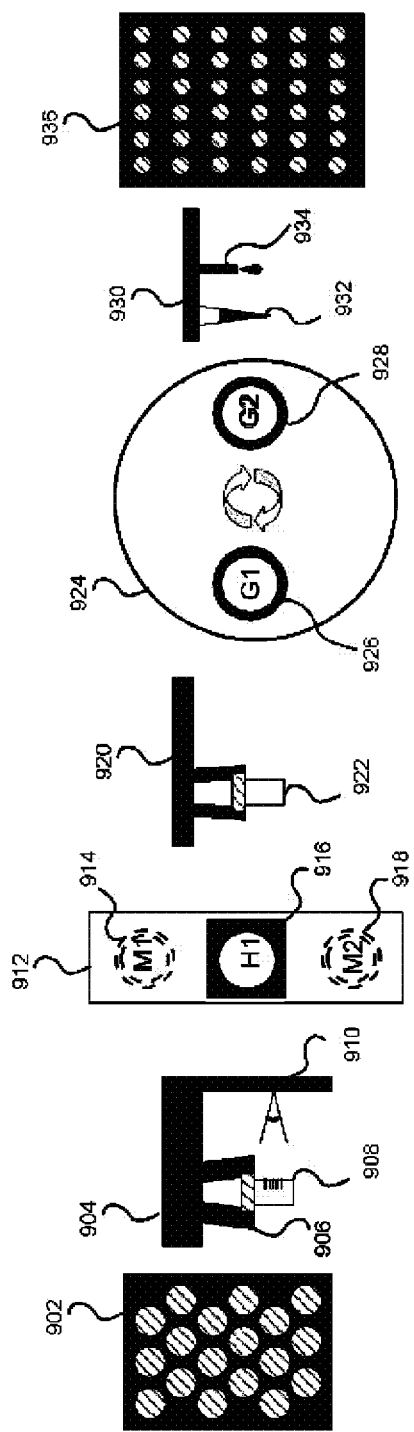

FIG. 9A provides an overview of an exemplary station that provides input sample uncapping and transfer to ETUs. The samples are provided in tubes that are held in a sample rack 902 of any suitable type. A mixing station 912 is provided having as mixers M1 and M2 that are able to grip a tube and agitate its contents by an orbital platform motion. H1 is a holding station able to grip a tube. G1 and G2 are grippers 926 and 928 (for example, bellows grippers) that hold the lower part of a tube for uncapping. The grippers 926 and 928 are mounted to an uncapping station 924 that rotates to different positions to permit the sample contained in each gripper to access different functions (sample ingress or egress, uncapping, pipetting). Variant forms of the output rack 936 may employ different container formats, such as 15 mL conical tubes, ETUs, 96-well plates, 384-well plates, etc. Note that the word "output" refers to being the output of the uncapping and sample transfer process, and, accordingly, the output may be used as the input of a subsequent automated processing step.

As illustrated in FIG. 9A, input rack 902 may be accessible by transfer arm 904. Transfer arm 904 may contain gripper 906 for retrieving, holding, and releasing sample 908. Transfer arm 904 may retrieve one or more samples as described in reference to step 802 of FIG. 8. Transfer arm 904 may also contain barcode reader 910 for reading a sample barcode in accordance with step 804 of FIG. 8. At step 806 transfer arm 904 may place a retrieved sample in either mixer 914 or mixer 918 of mixing station 912. Mixing station 912 may also contain a holding station H1 at a holding location 916 which may receive, hold, and release samples from one or more transfer arms. Samples received at mixing station 912 may be mixed in accordance with step 806.

As described above in reference to FIG. 8, in step 808, transfer arm 920 may retrieve one or more samples, such as sample 922, from mixing station 912 for transport to uncapping station 924. Grippers 926 and 928 of uncapping station 924 may be accessible by one or more uncappers for uncapping as described in step 810. Uncapping station 924 may also rotate allowing access to pipetting and dispensing arm 930. Pipetting and dispensing arm 930 may contain one or more sensors for detecting a sample level in accordance with step 812 of FIG. 8. Pipetting and dispensing arm 930 may contain pipette 932 for aliquotting from a sample as described in reference to step 814 of FIG. 8. Pipetting and dispensing arm 930 may contain dispenser 934 for dispensing reagents or other materials into one or more output containers such as for example, a container, or a portion of output rack 936. Dispensing may occur when all sample containers are capped to reduce a chance of contamination. According to some embodiments, dispensing may occur for a plurality of containers on an output rack after the output rack has been filled.

After withdrawal of a sample has completed, uncapping station 924 may rotate a sample container back to a position under an uncapper so that the container may be recapped. Recapping may occur as described above in reference to step 816 of FIG. 8. After recapping is completed, transfer arm 920 may retrieve a sample from the uncapping station and place the sample in holding location 916 of mixing station 912. Transfer arm 904 may return the sample to input rack 902.

FIG. 9B shows functions provided by an exemplary uncapping station. FIG. 9B illustrates rotation of the grippers to different positions to provide access of the sample tubes for different functions. FIG. 9C shows the functions available at each position. Uncapper 1 (U1) and Uncapper 2 (U2) are independently activated to uncap or recap a sample vial. A system may be configured to ensure that only one vial is uncapped at a time, which decreases the possibility of cross-contamination and prevents caps from being replaced on a different vial than they came from. Transfer arm refers to access for ingress or egress of sample vials. Pipetting arm refers to access of a pipettor, e.g., to draw a volume of the sample out of the sample vial. Optionally, before or during pipetting of the sample out of the sample vial, the vial is tilted at an angle, such as an angle between about 10-20 degrees or about 10-35 degrees, such that sample dead volume is decreased. The exact tilt angle may vary depending on the particular sample bottle and pipette geometry, and, while these ranges are believed to have a particular beneficial use in some circumstances, they are meant to be exemplary. The liquid level in a sample vial is optionally sensed (e.g., with an optical, ultrasonic, or mass-based sensor, or by measuring the liquid volume pipetted from the vial) to determine whether tilting is required to obtain the desired sample volume and/or to ensure that the sample volume is low enough to permit tilting to a given angle without causing a spill.

Figure 10B:
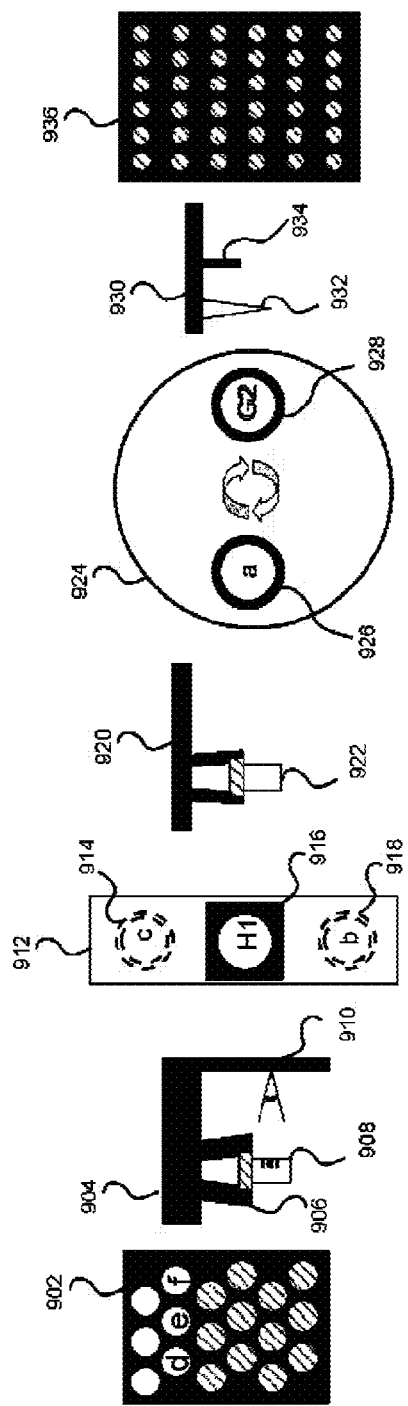

FIGS. 10A-F illustrate an exemplary uncapping and sample transfer work flow. Sample vials are shown with lower-case letters a through f. System throughput is illustrated by subsequent samples moving sequentially behind one another through the various stations. The use of station H1 for sample holding is optional; for example, the first transfer arm may directly reach the transfer position in the uncapping station. The barcode reader may be attached to the first transfer arm as depicted, or may be located in a fixed position; additionally, a separate transfer arm may pick up samples for barcode reading. Problems with a particular sample, such as barcode not recognized, sample volume insufficient, sample turbidity insufficient, unable to open cap, etc. may result in a sample being returned to its vial (if it already been drawn) and the vial being deposited in a "reject tray" rather than back in its original position in the input rack. As illustrated in FIG. 10A, sample a may be mixed in mixer 914 separately and independently from sample b. Sample b may be mixed concurrently in mixer 918.

Figure 10C:
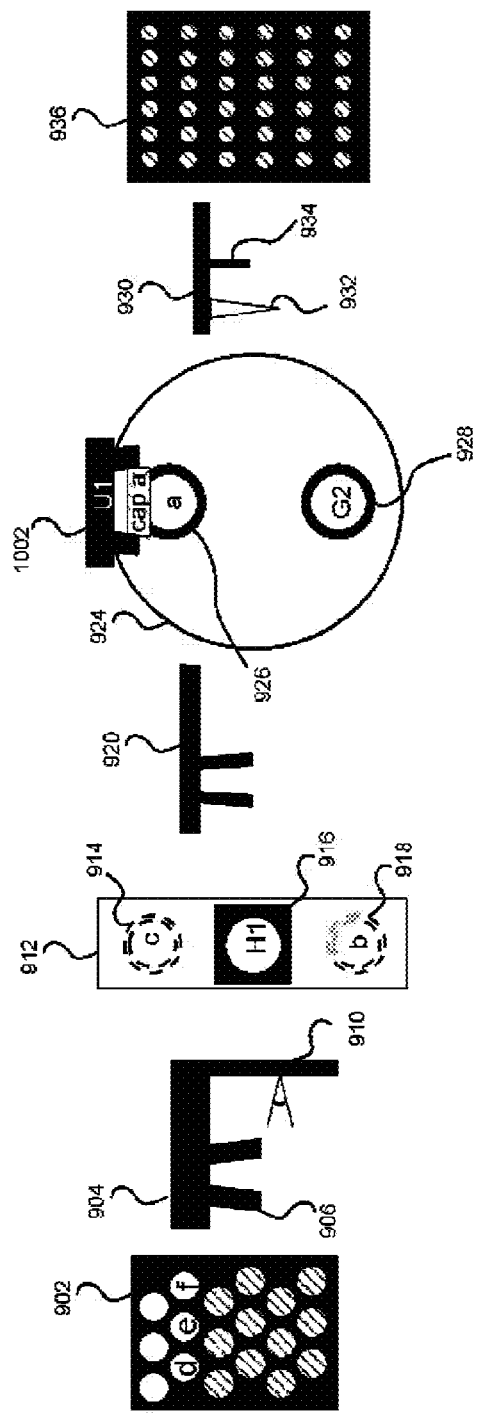
Figure 10D:
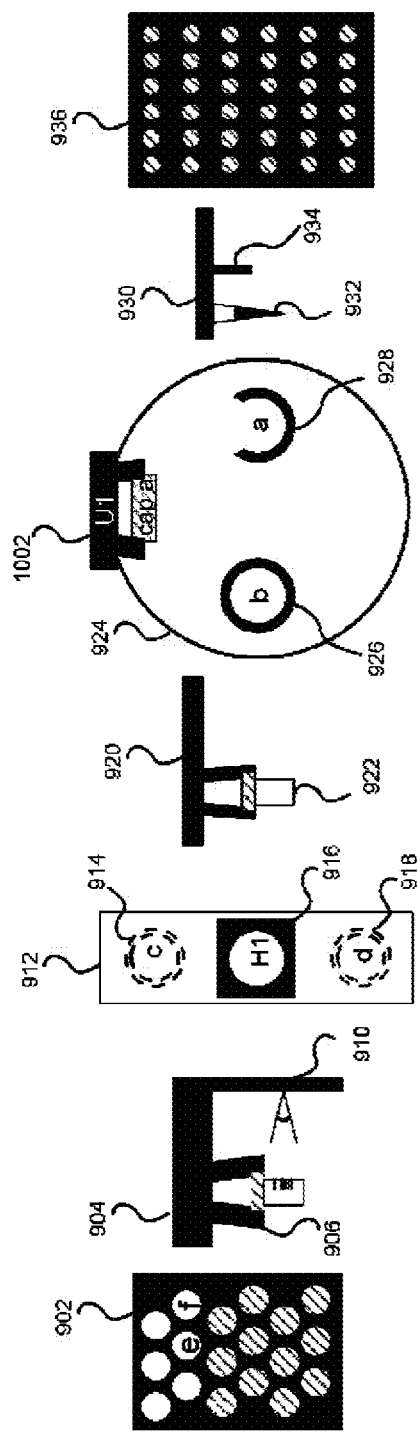

As illustrated in FIG. 10B, sample a may be transferred to gripper 926 after completion of mixing. This may allow the transfer of sample c from input rack 902 to mixer 914. As shown in FIG. 10C, uncapping station 924 may receive sample a in gripper 926 and rotate sample a beneath uncapper 1002. Uncapper 1002 may remove cap a. As shown in FIG. 10D, uncapping station 924 may be rotated so that sample a may be accessed by pipetting and dispensing arm 930. In this position, gripper 928 may be accessible to transfer arm 920. Transfer arm 920 may place sample b in gripper 928. After the removal of sample b from mixer 918, transfer arm 904 may retrieve sample d, scan a barcode of sample d, and place sample d in mixer 918. Mixing of sample d may commence.

Figure 10E:
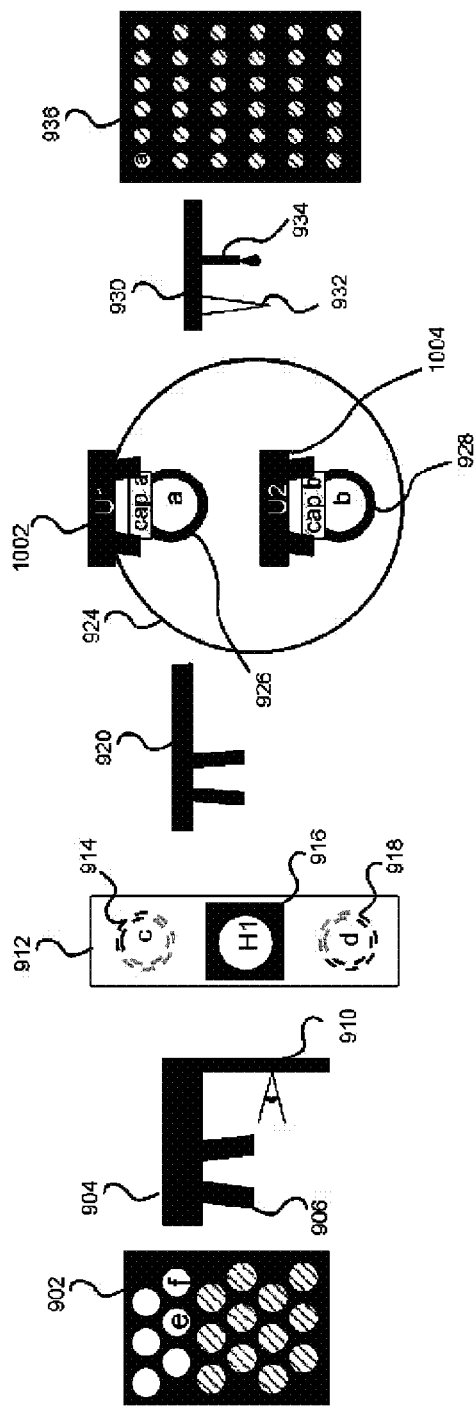

As illustrated in FIG. 10E, after completion of sample extraction from sample a by pipetting and dispensing arm 930 and depositing of sample b in gripper 928, uncapping station 924 may rotate sample a back beneath uncapper 1002. Sample a may be recapped. After recapping, according to some embodiments, pipetting and dispensing arm 930 may add one or more reagents to sample a in output rack 936. After capping of sample a, uncapper 1004 may uncap sample b. Once sample b is uncapped, uncapping station 924 may rotate allowing sample a to be retrieved by transfer arm 920 and placed in holding location 916 of mixing station 912. After sample a is placed in holding location 916, transfer arm 920 may retrieve sample c from mixer 914.

Figure 10F:
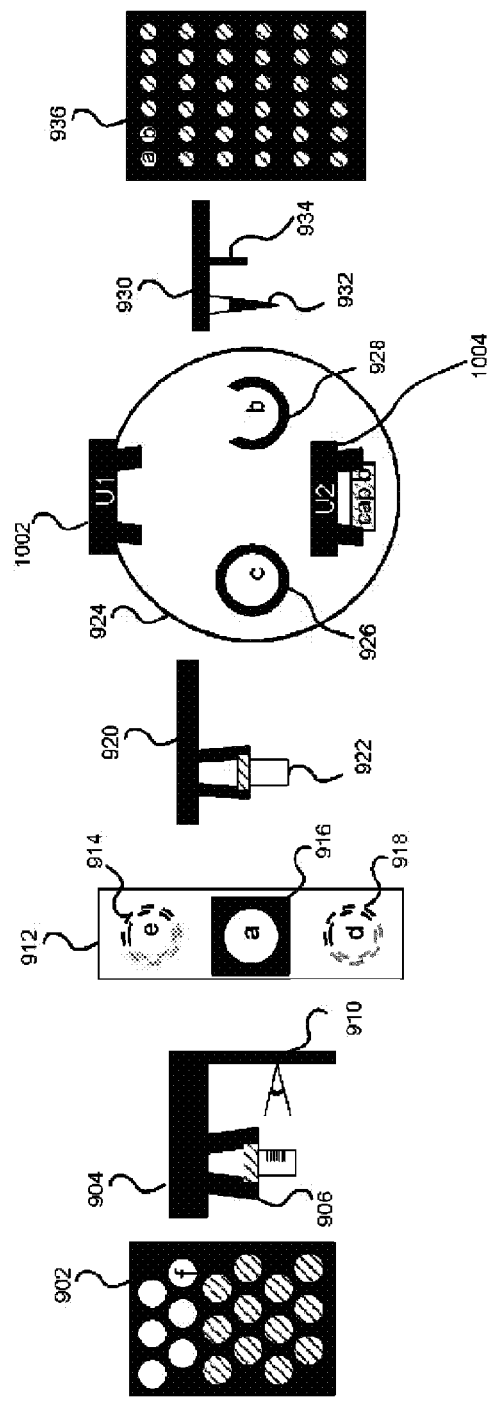

As shown in FIG. 10F, transfer arm 920 may place sample c in gripper 926 of uncapping station 924. Sample b may be accessed concurrently by pipetting and dispensing arm 930 to allow drawing of a sample and depositing of the sample into output rack 936. Transfer arm 904 may retrieve sample e, scan a barcode of sample e, and deposit sample e in mixer 914. Mixing of sample e may commence. Transfer arm 904 may return sample a from holding location 916 to input rack 902.

As with other features, processes and devices described herein the foregoing embodiments of a DCU and its processing steps may be used in other embodiments, and may even be provided as a standalone unit that is used for upstream sample processing.

Exemplary Extraction Tube Units and Grippers

Figure 11:
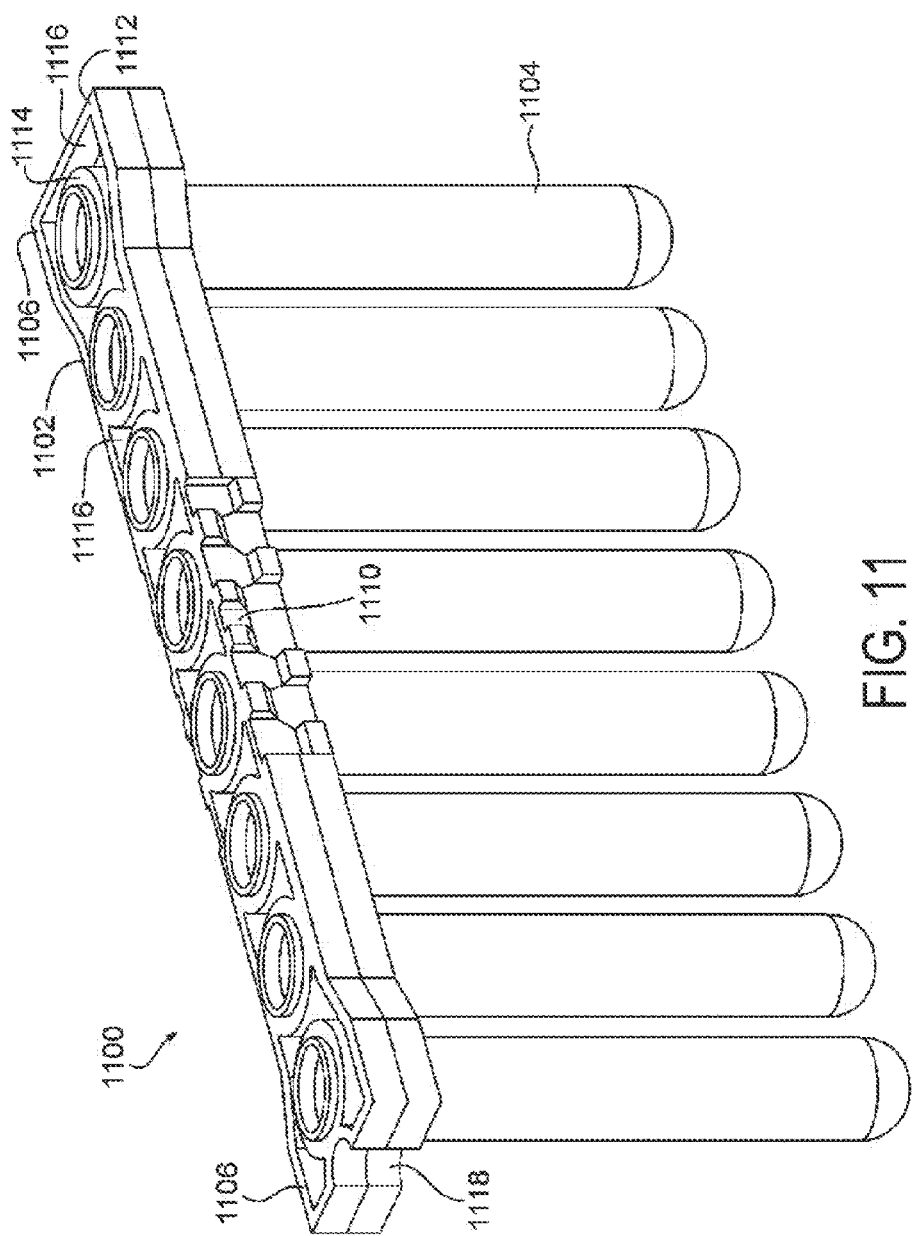
FIG. 11 is an isometric view of an exemplary extraction tube unit.

FIG. 11 illustrates and exemplary embodiment of an extraction tube unit ("ETU") 1100 that may be used as an intermediary vessel in the processes and systems described herein or in other systems. This ETU 1100 may be similar or identical to the one described above with respect to FIGS. 1 and 2. Typically an ETU will include an identifying feature, such as a barcode, and a gripping surface that facilitates holding and/or movement of the ETU by an automated system. An individual sample position or test tube within an ETU may be referred to as an ETU tube or ETU position.

The exemplary ETU 1100 comprises a frame 1102 and a number of test tubes 1104. In this embodiment, eight test tubes 1104 are provided, and each ETU corresponds to a column of a typical 96-well sample plate. However, twelve-tube ETUs and ETUs having other numbers of test tubes may be used in other embodiments. The frame 1102 may comprises a rigid structure that has suitable strength to convey the tubes 1104 and samples contained therein throughout the processing steps without substantially deforming under applied loads. The material also should be stable and sufficiently strong at the operating temperatures within the system. Suitable materials may include, for example, metal, wood, or plastic (e.g., nylon, polyvinylchloride, polypropylene, polystyrenes such as ABS and HIPS, etc.).

The tubes 1104 may comprise any suitable shape. The embodiment depicted has a round bottom which facilitates vortex mixing and minimizes pipetting dead volume. Conical bottom tubes would also share these characteristics. Other shapes, such as flat-bottomed shapes, may be used in other embodiments. The tubes 1104 may be configured to facilitate upstream or downstream processing. For example, the distance between each tube 1104 may be about 18 mm, which corresponds to about twice the space between the wells in a standard 96-well microplate. This spacing permits a fixed-width 4-channel pipettor to draw samples from 4 tubes within the ETU and dispense the samples into alternating positions in a 96-well microplate such as described below, which facilitates transfer of samples. The tubes 1104 may be made of any suitable material, such as glass or plastic. Where optical testing is conducted, such as in a turbidity test, the test tubes 1104 preferably is formed in part or entirely from a transparent or semi-transparent material having sufficient clarity and transparency to permit the desired testing. The test tubes 1104 may be formed integrally with the frame 1102 (such as by forming them from the same material that forms the frame 1102 or molding them in place within the frame 1102), or formed separately and joined to the frame (such as by press-fitment, adhesives, fasteners, threads formed on the test tubes 1104, and so on).

The test tubes 1104 are arranged in a line along the length of the frame 1102, but in other embodiments, in which the frame 1102 may have different shapes, the test tubes 1104 may be arranged in any other suitable array or pattern.

As shown in FIG. 11, frame 1102 is elongated, and may have enlarged ends 1106 that result in recesses being formed along one or both long sides of the frame 1102. In the shown embodiment, the frame has a "dog bone" shape as viewed from above. As a result of providing the enlarged ends 1106, the recesses create spaces between adjacent ETUs when multiple ETUs are tightly packed together. This permits a gripper 1200, described below, to access and individually grasp each ETU 1100. The ETU 1100 also may include registration features that help the user properly align the ETU in the system. For example, where it is desired for the ETU 1100 to be placed in the PAS 100 in only one orientation, the frame 1102 may have a notch 1118 at one end that helps identify the proper orientation. The notch 1118 or other registration feature may also engage a corresponding feature in the PAS 100 or other equipment to prevent installation in the incorrect orientation.

The frame may have a horizontal groove 1108 and a vertical groove 1110 on each long side. The grooves 1108, 1110 may be formed using any suitable manufacturing process. In the shown embodiment, the ETU frame 1102 is molded from plastic in a 2-part mold. An upper mold half forms the top of the frame 1102, and a lower mold part forms the bottom of the frame 1102. This arrangement has been found to be favorable in at least some embodiments because it permits the frame 1102 to be easily and inexpensively formed with a rigid outer perimeter wall 1112, cylindrical bosses 1114 to support each tube 1104, and one or more cutouts or recesses 1116 between the perimeter wall 1112 and bosses 1114. This produces a frame 1102 that is rigid, but lightweight and consumes less plastic or other fabrication materials. While the vertical grooves 1110 are readily formed using a simple 2-part molding process, it may be necessary to use an side insert form the horizontal grooves 1108. The need for such additional molding steps and expense has been eliminated in the embodiment of FIG. 11 by forming the horizontal groove 1108 in staggered segments. In this embodiment, upper faces formed on the bottom half of the mold form the downward-facing portions (i.e., the upper edge) of the horizontal groove 1108, and downward faces of the upper mold half form the upward facing portions (i.e., the lower edge) of the horizontal groove 1108. Of course, any other suitable manufacturing method may be used in other embodiments.

Figure 12:
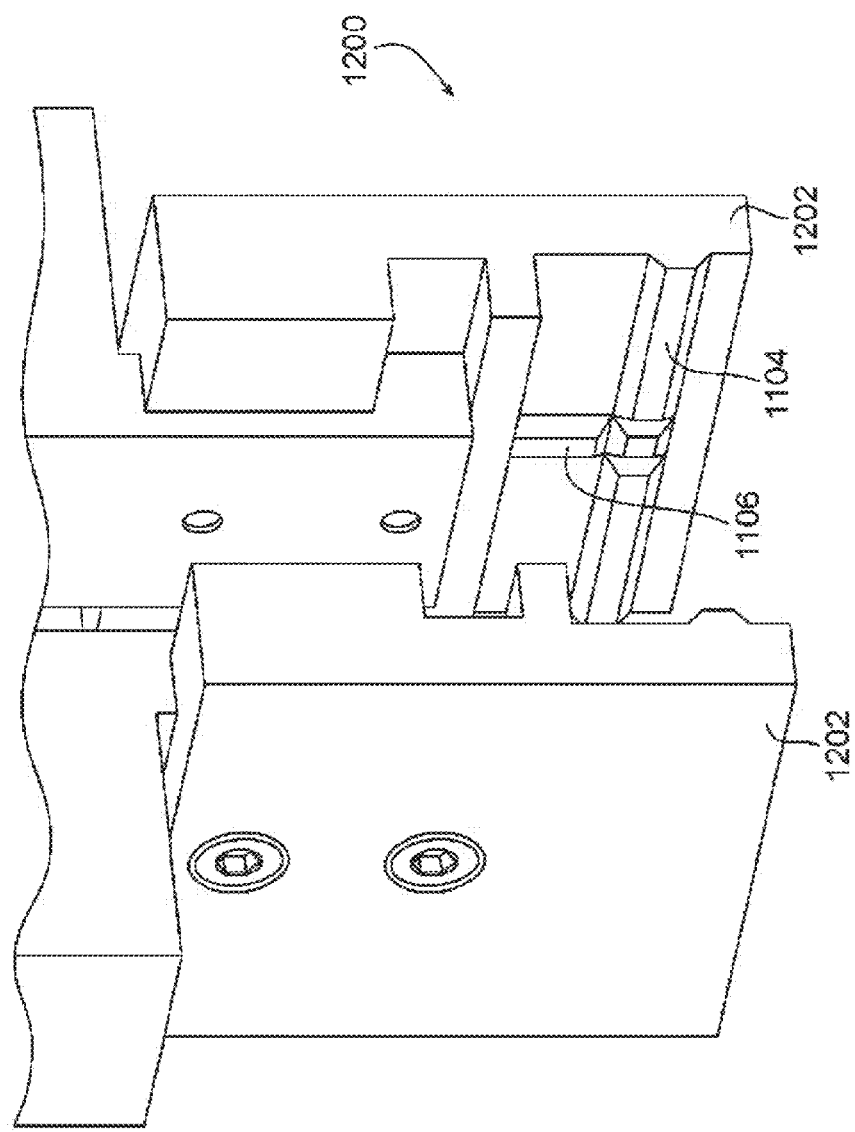
FIG. 12 is an isometric view of an exemplary extraction tube unit gripper.

The grooves 1108, 1110 on the ETU 1100 correspond to similar structures on a gripper 1200, shown in FIG. 12, that is used to move and manipulate the ETU 1100. As shown in FIG. 12, the exemplary gripper 1200 comprises two opposed jaws 1202 that can be moved together when necessary to grasp the ETU 1100 along its long sides. As with other grippers described herein, one or both jaws 1202 may be moveable by any suitable means, such as a servo-motor or pneumatic or hydraulic drive piston, and the gripper 1200 may have alternative shapes and constructions. The jaws 1202 also may simply be spring loaded to flex over and clamp onto the ETU by spring force, in which case some kind of clamp or other gripping member may be used to hold the ETU when its desired to release it from the jaws 1202, or the jaws 1202 may include an actuator that forces them open to release the ETU. Other variations will be readily apparent in view of the present disclosure.

Each jaw 1202 has a horizontal rib 1204 and a vertical rib 1206. The horizontal ribs 1204 are shaped and sized to extend into the horizontal grooves 1108, and the vertical ribs 1206 are shaped and sized to extend into the vertical grooves 1108. When so positioned, the gripper jaws 1202 securely hold the ETU frame 1102. In addition, some or all of the ribs 1204, 1206 and grooves 1108, 1110 may be chamfered, rounded or beveled to help them fully and properly engage even if there is some misalignment between the jaws 1202 and the frame 1102. An example of such a chamfer is shown in the Figures. In this embodiment, the gripper and ETU are configures such that the jaws 1202 will realign and grasp the ETU 1100 even if they are misaligned by up to about 1 to 2 millimeters. This helps to hold the ETU tightly during high speed motion and can tolerate a relatively large mismatch in ETU position. This keyed configuration may allows the grippers to operate without the use of addition of a compliant material which may be subject to wear, but it will be understood that removing any compliant material is not required in all embodiments.

Exemplary ETU Transport Mechanism

As noted above, any suitable mechanism may be used to transport the ETUs through an exemplary processing system. For example, the ETUs in the embodiment of FIGS. 1 and 2 may be loaded into the PAS 100 a rack on that holds the ETU 1100 by each end of the frame 1102. Such a rack may have any suitable springs, arms, conveyors and the like that move the ETU 1100 along the rack from the input location 110, to the loading location where it receives samples, to the output location where it is transferred by a transfer unit 224 to a processing area 226. The transfer unit 224 may comprise any suitable articulating mechanism, such as known in the art, and may include jaws such as those described with respect to FIG. 12, to grip the ETUs 1100. Once in the processing area 226 one or more ETU movers may be used to convey the ETUs between the various processing stations. Where multiple ETU movers are used, the movers may operate on parallel tracks and each have access to all positions or stations, or multiple movers may be provided on the same or different tracks and have access to only some of the positions.

Figure 13:
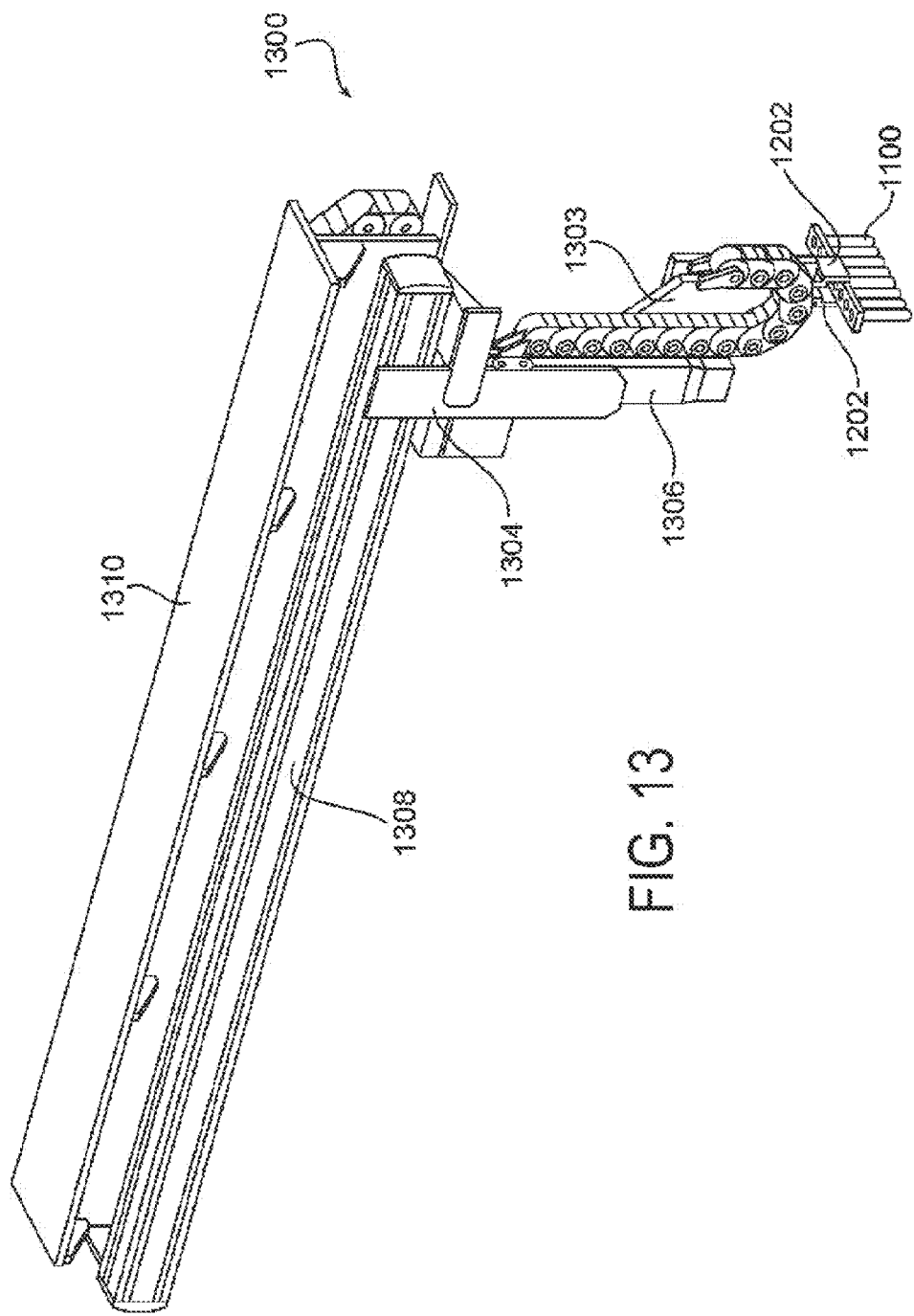
FIG. 13 is an isometric view of an exemplary extraction tube unit transport mechanism.

FIG. 13 illustrates one example of an ETU mover 1300 that may be used as a single unit that transfers all of the ETUs between the various stations. The ETU mover comprises a gripper head 1302 that is connected to a shuttle 1304 by a servo-operated machine screw 1306, hydraulic or pneumatic cylinder, or by any other suitable device, to allow the head 1302 to move vertically with respect to the shuttle 1304. The shuttle 1304 is movably connected to a track 1308 that is attached to the PAS frame 1310 above the processing area 226, and provided with suitable means to traverse the shuttle 1304 laterally along the track 1308. Such traversing devices are well-known in the art and need not be described here. The gripper head 1302 includes a grip, such as the jaws 1202 described above, for grasping and moving the ETUs.

In use, the ETU mover 1300 operates throughout the clock cycle to move ETUs from one station to the next. Typically, the ETU mover 1300 begins at the last process (e.g., moving ETUs to a solid waste receptacle) to free the last processing station, then progresses backwards through the flow path to move each ETU into the next position. The ETU mover preferably completes all necessary ETU movements once per clock cycle. During startup and the last stages of operation during a shift, ETUs may not be present at all stations. For example, the first ETU that is processed remains in the incubator for multiple clock cycles. Under these circumstances, the ETU mover 1300 may be programmed to skip operations, or it may simply continue to operate as if ETUs were in all of the stations. The latter option may be preferred to simplify operation and reduce the likelihood of errors.

Exemplary Magnets

Figure 14A:
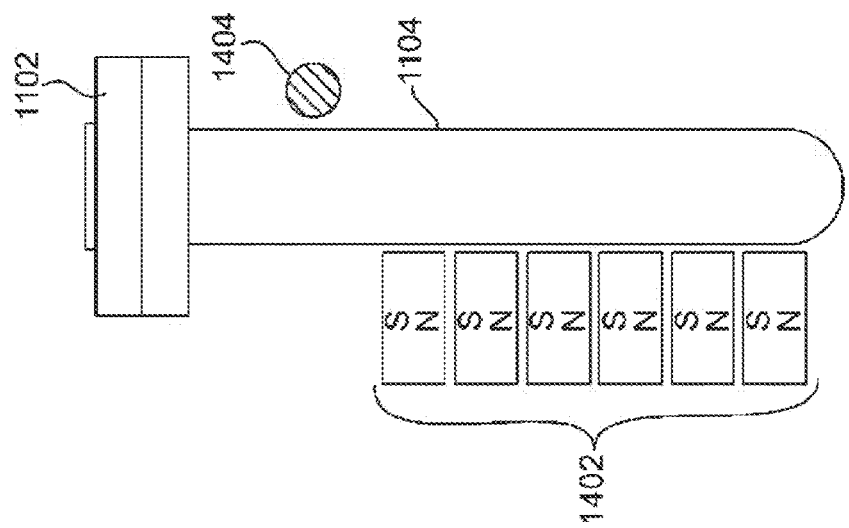
FIGS. 14A and 14B are side elevation views illustrating exemplary configurations of magnets located adjacent an extraction tube unit.
Figure 14B:
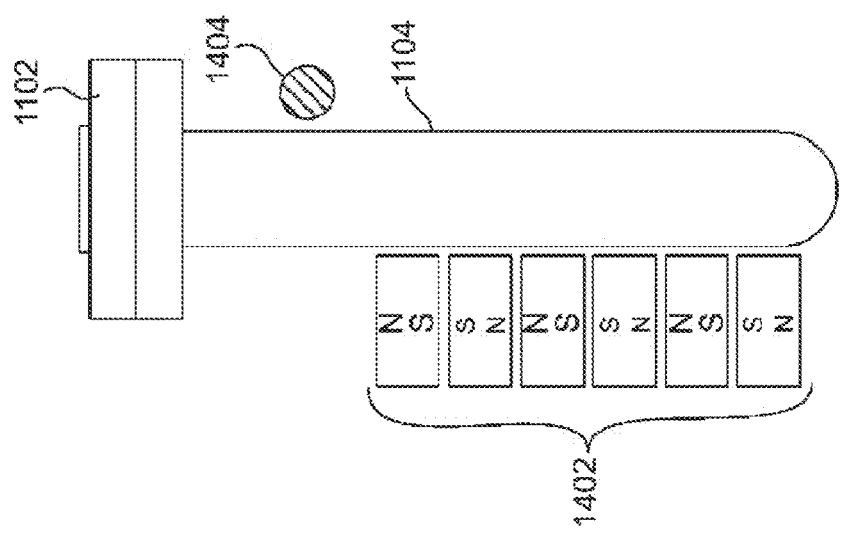

FIGS. 14A and 14B show exemplary arrangements of magnets for use in an aspiration station, such as the first and second aspiration stations 238, 240 described above. The depicted systems use multiple bar magnets 1402 of the rare earth type (e.g., neodymium-iron-boron), but any other suitable type of magnet may be used (e.g., electromagnets, ferric magnets, ceramic magnets, plastic magnets, etc.).

The magnets 1402 are located on one side of the ETU tubes 1104 to attract paramagnetic beads inside the tubes 1104. While a single strong magnet may be used for one or more tubes 1104, multiple magnets 1402 may be used for each tube, or across a number of tubes. A crossbar 1404 may be positioned opposite the magnets 1402 to help press the tubes 1104 towards or against the magnets 1402. Typically, the magnet array has two or more magnets depending on the volume of the paramagnetic bead solution. To enhance the attraction of paramagnetic beads, a small space may be set between the magnets at the areas between adjacent magnets. The precise spacing may be maintained using an aluminum spacer. This arrangement helps to attract the beads along the wall of the tube quickly. The magnets 1402 may be arranged in any suitable manner. For example, the orientation as shown in FIG. 14A has the adjacent magnets arranged North-to-North and South-to-South. This arrangement is believed to attract beads faster than the North-to-South arrangement shown in FIG. 14B, but either configuration may be used. Without being limited by any theory of operation, it is believed that the North-to-North and South-to-South orientation shown in FIG. 14A causes the magnetic field to extend further into the sample than a North-to-South orientation such as is shown in FIG. 14B, resulting in greater attractive force and faster attraction. Additional possible configurations include using magnets on both sides of the tube or surrounding the tube. Another configuration would use a magnetic probe inserted into the tube to attract the beads, which could then be either withdrawn or simply held to allow liquid aspiration. For example, a magnetic probe could also include an aspiration inlet. Optionally a magnetic probe comprises a magnetic material that can be moved in an out of a sheath, such that the beads are captured against the sheath and then released when the magnet is withdrawn. A magnetic or paramagnetic probe may be moved within the sample volume to increase the rate at which beads encounter the magnetic field and are pulled to the probe, causing faster attraction of the sample.

It has been found that bar magnets that are 6" long×⅛" tall by $\frac{5}{16}$" deep may be used. The 6 inch length extends the entire length of an exemplary ETU 1100. Alternatively, two 3-inch magnets may be used end to end. Without being limited to particular sizes, the vertical thickness of the magnets in the exemplary embodiment may comprise around a ⅛" minimum dimension, with the maximum being about the length of the test tube 1404, or about 3 inches.

Exemplary Aspirator Assemblies

Figure 15A:
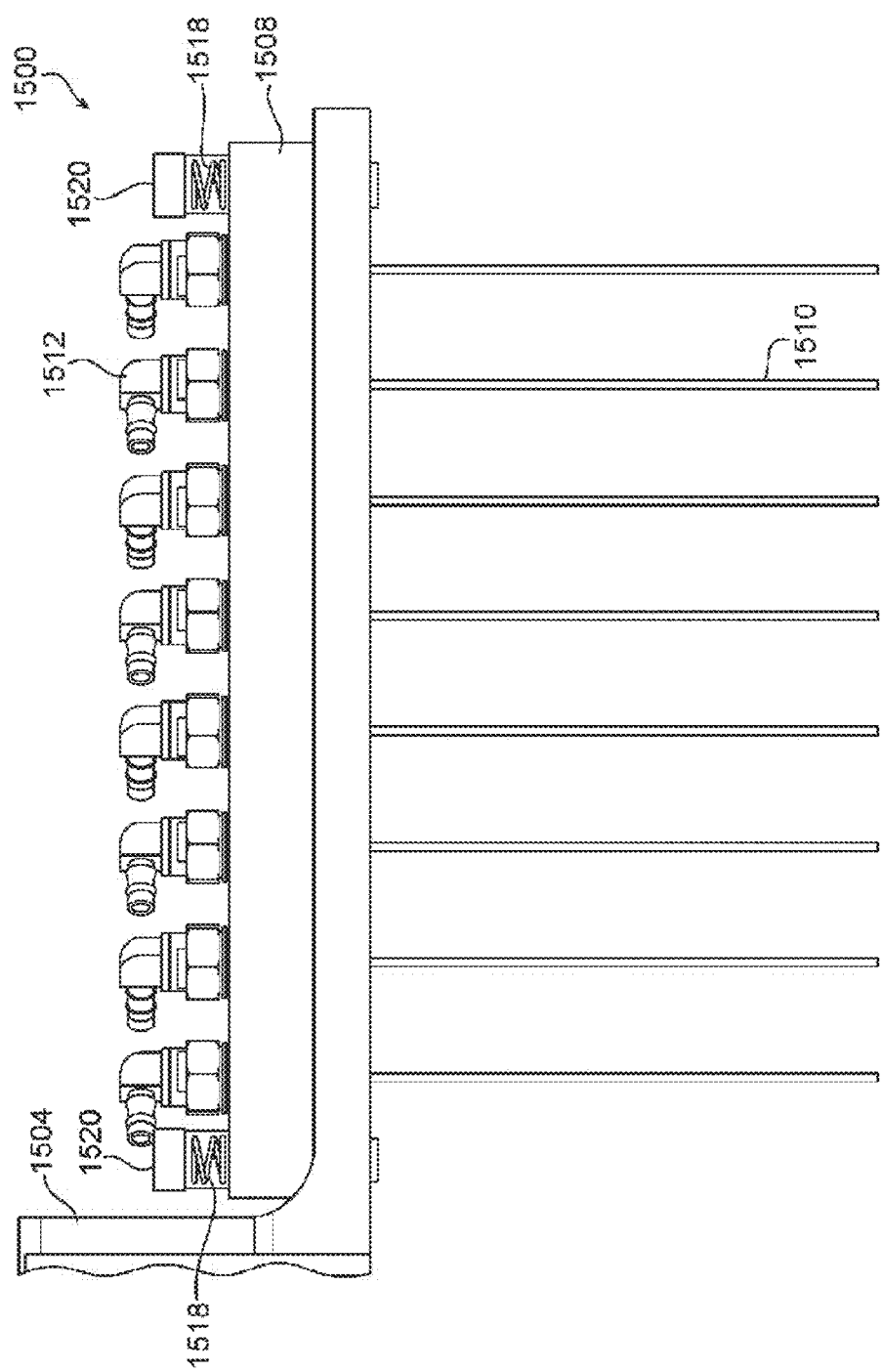
FIG. 15A is a side elevation view of an exemplary aspirator.
Figure 15B:
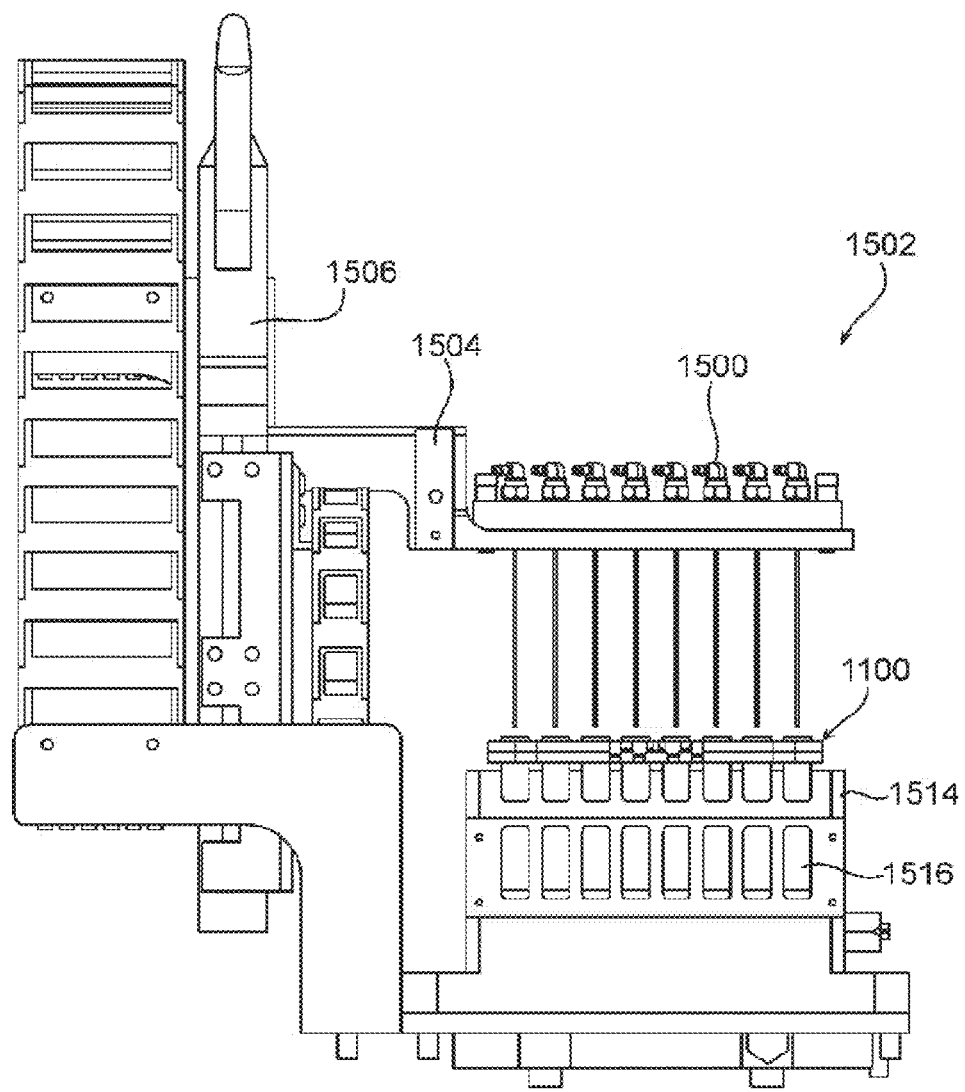
FIG. 15B is a side elevation view of an exemplary aspirator station employing the aspirator of FIG. 15A.

FIGS. 15A and 15B illustrate an exemplary aspirator 1500 and aspirator station 1502 that may be used with various embodiments of the invention. The aspirator 1500 is mounted to an aspirator frame 1504 that is connected to a suitable actuating arm 1506 to move the aspirator 1500 laterally to various processing stations and vertically into and out of the ETU tubes 1104. The aspirator 1500 comprises an aspirator body 1508 that is mounted to the aspirator frame 1504, a number of hollow aspirator tips 1510 that are shaped and sized to extend to the bottoms of the tubes 1104, and fittings 1512 that fluidly connect the tips 1510 to one or more suction sources.

As noted above, the aspirator 1500 may be used during a processing step in which magnets are used to attract magnetic beads in the tubes 1104. Such an arrangement is shown in FIG. 15B, in which the ETU 1100 is mounted in an aspirator station 1514 having openings 1516 through which the tubes 1104 are exposed to magnets (not shown). As such, if the tips 1510 comprise a magnetic material, they could deflect during aspiration. To overcome this potential difficulty, the tips 1510 may be made of Inconel™ (Special Metals Corporation, New Hartford, N.Y.), an austenitic nickel-chromium-based superalloy. Other designs could employ other nonmagnetic materials, such as plastic, aluminum or austenitic steel, use magnetic materials having lateral reinforcement to avoid deflection, or be curved away from the magnet position such that deflection towards the magnets does not draw their openings away from the desired position. A non-wetting coating, such as Teflon™ (polytetrafluoroethylene) or ceramic vapor, may be applied to the tips to reduce the likelihood of carryover from one sample to another.

One or more pumps (not shown) may be used for all of the tips 1510, but a configuration using a single pump may lose suction in some or all of the tubes when one tube is emptied. As such, in one embodiment, each aspirator fitting 1512 may be connected to one head of a two-headed pump. Although this requires multiple pumps (e.g., four pumps for an aspirator having eight tips, as shown) This ensures that all of the tubes will be aspirated generally independently, even if one tube is emptied before others are, and provides greater independence of operation. During aspiration, the tips 1510 are pressed to the bottoms of the ETU tubes 1104. To at least partially accommodate slight variations in the tube lengths or uneven placement of the ETU 1100, the aspirator body 1508 may be movably mounted on the aspirator frame 1504 by one or more springs 1518 that allow the tips 1510 to conform to the ETU position. The springs 1518 are captured between the aspirator body 1508 and end caps 1520 to allow the aspirator body 1508 to move upwards by compressing the springs 1518. In the shown embodiment, one spring 1518 is provided at each end of the aspirator body 1508, which allows the aspirator body 1500 tips 1510 to rock along the length of the frame 1506. While this amount of movement is believed to be suitable to obtain acceptable aspiration across an 8-tube ETU, in if greater accuracy or more independent controls is desired the each aspirator tip 1510 or groups of the tips 1510 may mounted on separate springs in other embodiments.

Exemplary Final Transfer Unit and Methods

Figure 16:
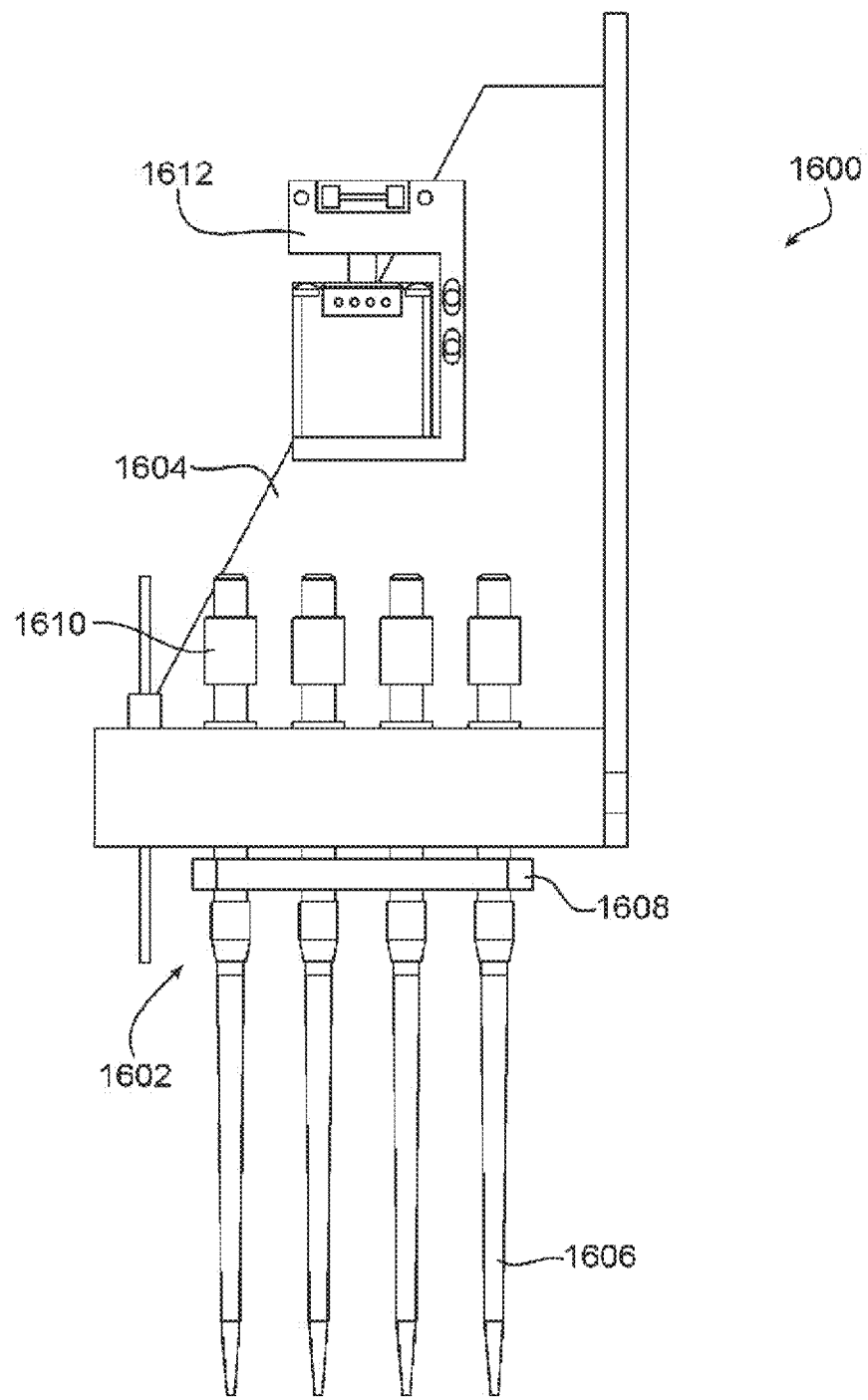
FIG. 16 is a side elevation view of an exemplary four-channel, fixed-separation pipettor.

FIG. 16 depicts an example of a final transfer unit 1600 that may be used with exemplary embodiments to transfer processed samples from an ETU to a sample tray. While the shown final transfer unit 1600 has particular application in a PAS, it may of course be used in other contexts and with other systems and processes. The exemplary final transfer unit 1600 comprises a four-channel, fixed-separation pipettor 1602 that is mounted on a moveable platform 1604. The pipettor 1602 can mount up to four pipette tips 1606, each of which is releasably and fluidly connected to a pipette channel 1610. To facilitate automation, the tips 1606 may be engaged by lowering the channels 1610 into the tips 1606 and applying pressure to secure them together, and disengaged using a motorized tip ejector 1612 that pushes on an ejector plate 1608 to slide the tips 1606 off the channels 1610. The relationship between the ejector plate 1608 and pipette tips 1606 is shown in FIGS. 17A and 17B, which show the ejector plate having bores 1712 that are large enough to pass over the pipette channels 1610, but small enough to abut and end of the pipette tip 1606 to push it off the channel 1610. Also shown in these figures are channel tips 1714 that are attached to each channel 1610 and comprise a deformable material disposed on its outer surface that compresses against an, inner surface of the pipette tip when inserted, thereby securing the tip 1606 to the channel 1610 and creating a suitable air-tight seal. Replaceable pipette tips and ejectors are known in the art and need not be described in detail here.

As best shown in FIGS. 17A and 17b, the pipettor channels 1610 may be mounted within respective bores 1702 through the pipette platform 1604. The channels 1610 can slide at least some distance along the bores 1702, but are captured in place by, for example, upper and lower retainer rings 1704, 1706, that prevent the channels 1610 from escaping the bores 1702. A spring 1708 is captured between the lower retainer ring 1706 and the pipette platform 1604 and is dimensioned to apply a restoring force that biases the channels 1610 downward, as shown in FIG. 17A. In use, these springs 1708 provide a degree of independent vertical movement for each pipette channel 1610. When the pipettor 1602 is fully lowered into the ETU 1100, such as shown in FIG. 17B, the springs 1708 may independently compress as the pipettor tips 1606 contact the bottoms 1710 of each ETU tube 1104. Provided the spring travel distance on each pipettor channel 1610 is sufficient to accommodate the difference in tube lengths or any offset in the ETU, this independent movement should allow all of the pipettor tips 1606 to contact the bottom of their respective ETU tubes 1104. In this position, an over volume aspiration may be performed, and there is significant assurance that all of the fluid in each tube will be aspirated.

The foregoing arrangement, or similar arrangements in which one or more tips may be independently moveable with respect to the others, may be particularly helpful where the volume in the tubes may be small, and liquid level detection may not be suitable to assist with liquid transfer. For example, in the PC and Surepath protocols discussed above, the final transfer unit 1600 transfers extracted nucleic acids contained in the ETUs to the corresponding column of a 96-well plate, however the volume of the final concentrated nucleic acid solution may be less than about 100 ul. It has been found that, despite the low volume, the use of independently moveable pipettor tips 1606 enables consistent and complete transfer of such fluids. In this case, liquid level detection, which is difficult to implement when there is less than about 100 ul liquid in a tube, is not required.

Where the transfer volume is the same for all of the tubes, the final transfer unit 1600 may use a pipetting mechanism comprising a series of air and/or liquid cylinders that are driven by a single motor or pump. In other embodiments, however, multiple pumps may be used to ensure accurate aspiration and dispensing for each pipette.

Figure 18:
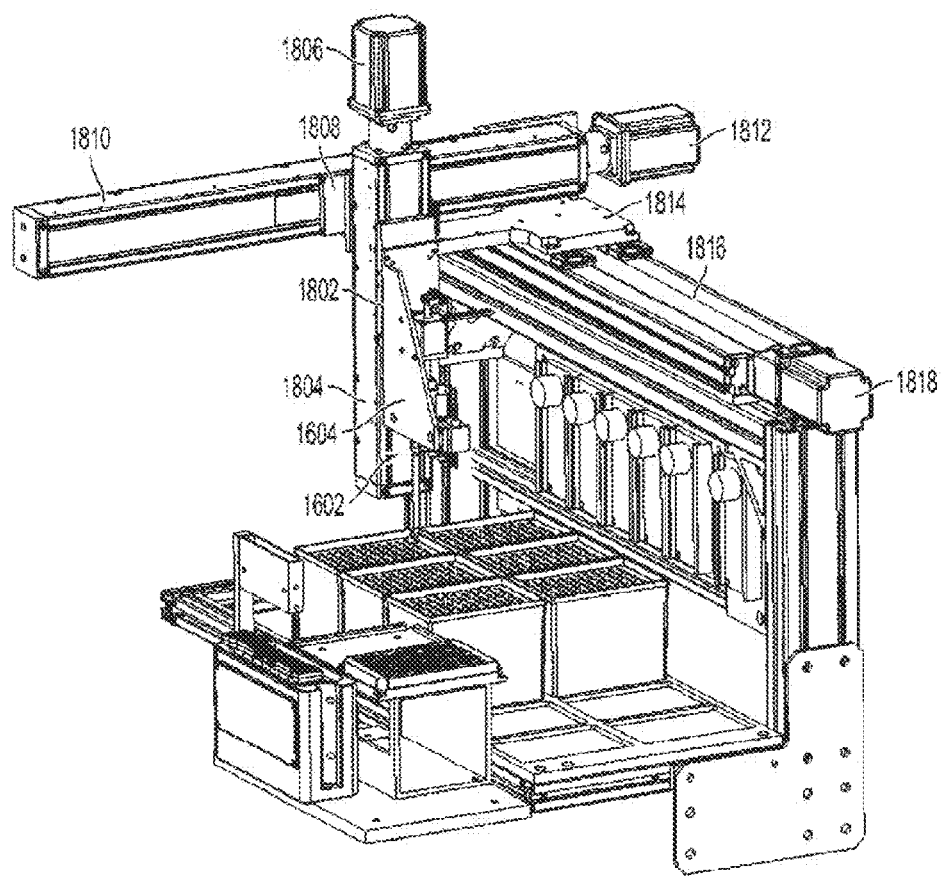
FIG. 18 is an isometric view of a manipulation system for an exemplary final transfer unit including the pipettor of FIG. 16.

Referring now to FIG. 18, an example of a manipulation system for an exemplary final transfer unit 1600 is shown. Here, the pipettor platform 1604 is mounted to a first shuttle 1802 that is adapted to move vertically on a first track 1804. A servo-motor 1806 or any other suitable drive mechanism may be used for this purpose. The first track 1804 is, in turn, mounted to a second shuttle 1808 that is laterally moveable along a second track 1810 by its own motor 1812. The second track 1810 is mounted to a third shuttle 1814, which is laterally moveable along a third track 1816 in a direction perpendicular to the second track 1810. A third motor 1818 is provided to control the movement of the third shuttle 1814. The foregoing arrangement provides three dimensional movement for the final transfer unit 1600. If desired, mechanisms may be provided to control rotation about any axis. In addition, in other embodiments, different mechanisms and control devices may be used to manipulate the final transfer unit 1600 though its desired range of motion. For example, it may not be necessary to provide movement along one horizontal axis in the embodiment of FIGS. 1 and 2, in which case the third shuttle, track and motor may be omitted. Other variations will be readily apparent in view of the present disclosure.

In order to complete the final transfer operation, the final transfer unit 1600 must move samples from the relatively large and widely-spaced ETU tubes into the relatively small and narrowly-spaced wells of a typical sample plate. One way to accomplish this may be to use a "varispan" arrangement, in which the width between the pipettor tips can be varied. This requires additional mechanisms and controls, but is possible in some embodiments. It has been found that, by properly selecting the distances between the pipette tips and ETU tubes and using a unique transferring protocol, the use of varispan pipettors may not be necessary. This may simplify the design, reduce costs, and improve reliability by eliminating a potential point of failure. Examples of this construction and protocol are shown in FIGS. 19A-19D, which are schematic diagrams illustrating two exemplary sample transfer operations in which samples are transferred from an exemplary extraction tube unit to a standard sample plate using fixed-width pipettors.

In the exemplary embodiment, the final sample plates comprise standard 96-well plates 208 in which the wells are spaced about 9 mm apart. The ETU tubes are spaced about 18 mm apart, which is twice the distance between the wells. In a first step, shown in FIG. 19A, the final transfer unit aspirates liquid from four adjacent tubes 1104 on the ETU 1100, and deposits the liquid into four alternating wells 1900 in the sample plate 208. In the next step, shown in FIG. 19B, the final transfer unit aspirates liquid from the other four adjacent tubes 1104 on the ETU 1100, and deposits the liquid into the other four alternating wells 1900 in the same row of sample plate 208. As explained above, after each step, the final transfer unit may discard the used tips into the empty ETU tubes to reduce solid waste volume. In an alternative embodiment, shown in FIGS. 19C and 19D, a similar process is used to transfer liquid from a twelve-tube ETU 1902 to the 12-row side of a standard 96-well plate, using a six-channel fixed-width pipettor. To facilitate these embodiments, the distance between centers of adjacent ETU tubes are approximately equal to a whole multiple "N" of the distances between adjacent positions in the output container. Transfer of all ETU samples can be performed by a fixed-width pipettor in N transfers. Moreover, both the number of tubes in an ETU and the number of positions in a column in the output container are divisible by N, such that all positions in an output container are used. It will be understood that the capacity of an ETU and the capacity of a column in the output container need not be equal; rather, all positions in the ETU tube can be drawn and all positions in the output container can be filled with a fixed-width multi-channel pipettor, as long as the number of channels is a common divisor of (a) the number of positions in a column in the ETU tube, and (b) the number of positions in a column in the output tray divided by N. It will also be appreciated that, in other embodiments, the distance between adjacent tubes may be any whole multiple of the distance between adjacent wells in a sample plate. For example, a fixed-width, two-channel pipettor can be used to transfer fluid from a six-tube ETU to a plate having six wells, provided the spacing between the tubes is either three times the spacing between the wells. Other variations will be understood in view of the present disclosure without undue experimentation.

Alternative Exemplary Processing System

Figure 20:
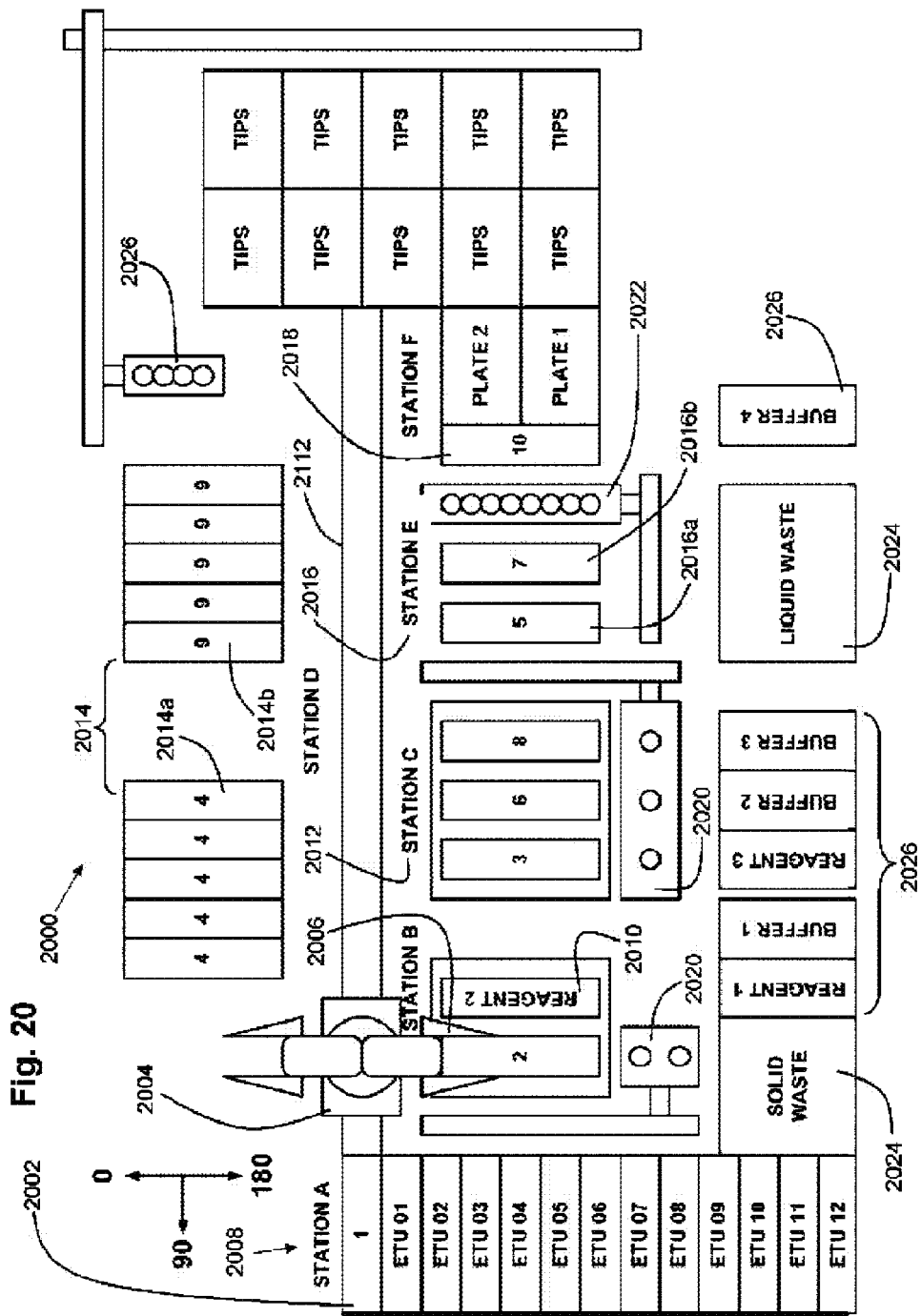
FIG. 20 is a schematic top plan view of alternative embodiment of a processing system.
Figure 21:
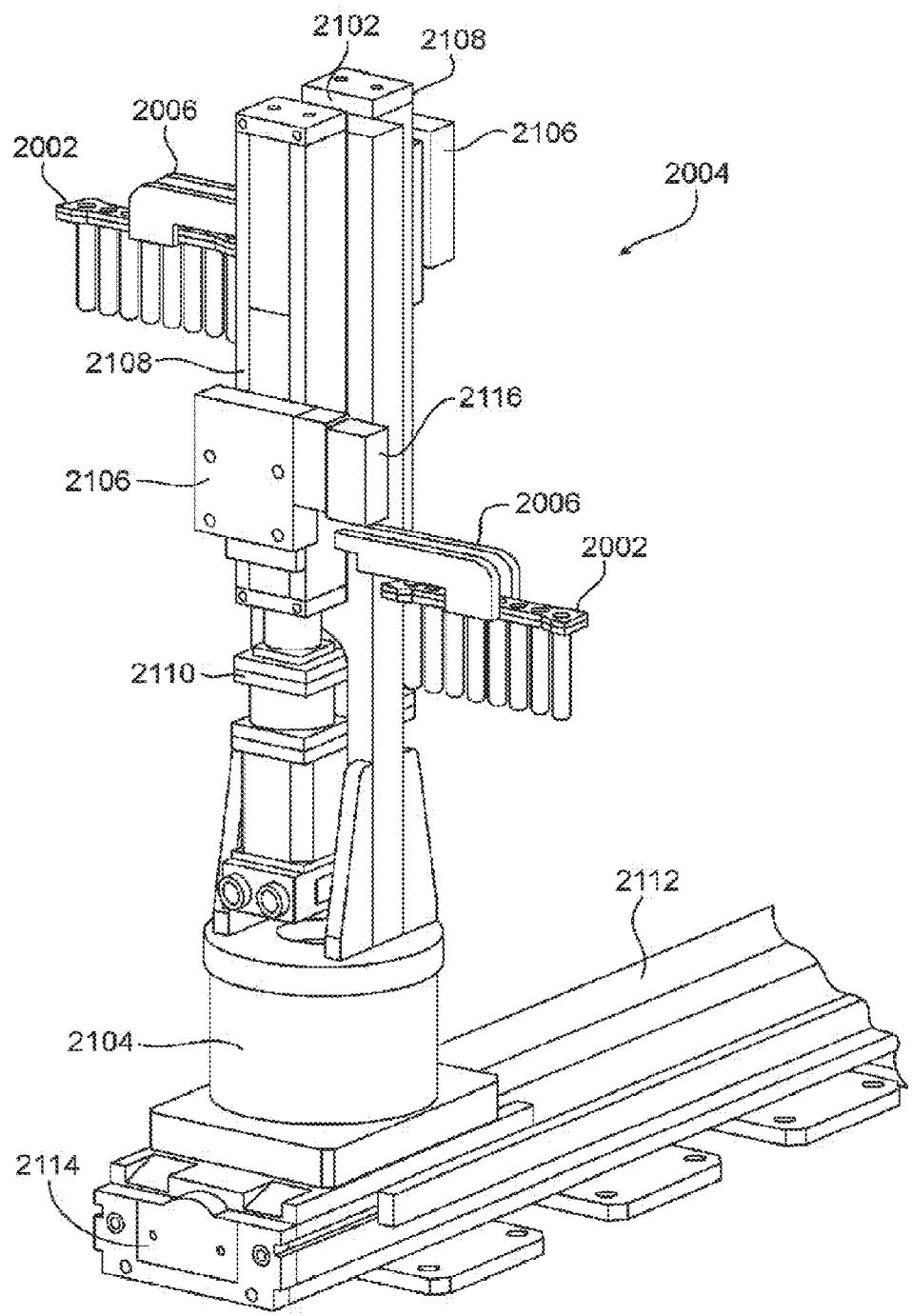
FIG. 21 is an isometric view of another exemplary ETU transport mechanism.

An alternative exemplary processing system is shown in FIG. 20. In this embodiment, the system 2000 is provided in a generally linear arrangement. Samples are provided in ETUs, and conveyed through the system by a six-axis ETU mover 2004. As shown in FIG. 21, the ETU mover 2004 has two grippers 2006, on opposite sides of a central column 2102. The central column rotates 180 degrees or more on a pedestal 2104, to permit the grippers 2006 to swap positions when needed. Each gripper 2006 is mounted on shuttle 2106, which, in turn, is mounted on a respective vertical track 2108. Suitable linear actuators 2110 are provided to move the grippers 2006 up and down, as required during processing. If desired, an angular actuator 2116 or other linear actuators may be provided to give the grippers 2006 even greater maneuverability. The entire ETU mover 2004 is mounted on a track 2112 and a linear actuator 2114 is provided to move the ETU mover 2004 back and forth along the track 2112.

Referring back to FIG. 20, the processing stations are arranged generally along a linear axis, with the ETU mover 2004 and its track 2112 located between the stations. During operation, the ETU may begin at the ETU station 2008 with two empty grippers, pick up a new ETU in one gripper, move to the first processing station 2010, pick up the ETU at that station, turn, and deposit the new ETU into that station. The ETU mover 2004 then carries the ETU it retrieved from the first processing station 2010, moves to the next station 2012, retrieves the ETU at that station 2012, and turns and deposits the ETU from the prior station 2010 into that station 2012. This process continues in this manner until all of the necessary ETUs are moved. The ETU preferably completes all of the transfers during the course of one clock cycle. In one embodiment, the clock cycle may be about 2 minutes, but other cycles are possible.

The processing stations may include an ETU supply station 2008, a first mixing station 2010, a second mixing station 2012 having three substations 2012a, 2012b, 2012c, an incubation station 2014 having multiple substations 2014a, 2014b, and aspiration station 2016 having two substations 2016a, 2016b, and a final transfer station 2018. These stations may operate like the ones described with respect to FIG. 2, or in other ways, as will be appreciated in view of the present disclosure. The system also may include various reagent dispensing arms 2020, an aspirator 2022 and a final transfer unit 2026, such as those described previously herein or according to other constructions. Waste containers 2024 and reagents also may be provided, such as described elsewhere herein.

As with previously discussed embodiment, some of the stations may include multiple substations or slots to hold ETUs for multiple cycles. A simplified version of this embodiment may eliminate the rotary axis, in which case the two grippers 2006 and all of the processing stations may be arranged on one side of the track 2112. A further simplified version of this system may have only one vertical movement component. In this embodiment, which is similar to the one described above with respect to FIG. 13, the robot may start from the last processing step and pick up ETUs from the previous processing slot and loads them to the current processing slot. Again, this is repeated for all the processing steps in about a 2 minute interval, but other intervals may be used.

Sample Tracking/Barcode Integration

As noted above barcoding or other identification technology may be integrated into various embodiments of processing systems. In the exemplary embodiment of FIG. 1, barcoding may be used extensively to identify samples, track the samples' location on input, output and intermediate processing containers (such as ETUs and output sample plates), and generally help assure quality control. For example, all sample bottles loaded in each sample rack may be barcoded, and the barcode is read as each sample is initially accessed. This can be used to guarantees both that the system identifies the sample as being one that is intended to be tested in the system, and that the sample can be identified for processing. Using this protocol, a sample may be placed in the reject tray if it is recognized, but determined to be a sample intended for some other process, or not recognized due to an unknown or missing barcode. The system may receive information about whether a particular barcode is to be analyzed from the CCU or another computer system or data file. If a sample with an unknown of missing barcode can be otherwise identified, it may be barcoded and processed. The system also may be operated in a forced testing mode that allows samples to be processed whether or not a barcode is recognized.

Reagents also may be barcoded. Preferably, the lot numbers and/or expiration dates of reagents are coded into the barcode and recognized by the system. Optionally (such as if local regulations require), barcodes may be used to ensure that old reagents are completely flushed whenever a new reagent is added from a new lot to prevent mixing of lots. Barcode tracking also may be used to better track reagent usage, and ensure that expired reagents are not used. A barcode scanner for the reagents may be provided, for example, in the chamber that holds the reagent, as a separate device, or as a scanner that is flexibly connected to the system by a tether or electric cord.

In one preferred embodiment, each ETU may be barcoded. The ETUs may be scanned before, as or after the samples are added to them, and a map may be generated to associate the samples to their particular locations (i.e., tubes) in the ETU. The ETU may be scanned again just before the samples are transferred to a 96-well plate or other output vessel. Additional scans may be performed at other locations. This provides further assurance of proper machine operation and a lack of outside interference, and helps confirm that each ETU has been fully processed through all process steps and that each sample in the output tray exactly corresponds to the expected sample. Barcoding the ETU or other sample processing containers also may permit recovery of a machine that fails or is interrupted during operations, by allowing either automated or manual scanning to associate each sample with its particular stage of processing. In such a system, it may be possible to precisely resume processing for each sample either after the machine is repaired or otherwise returned to operating condition, or by transferring the samples to a working machine or by continuing the processing manually from the last processing operation.

In addition, each 96-well plate may be barcoded and scanned before, during or after samples are transferred to it. This may be done to relate each sample from the ETU (and, by correlation, from each sample container) to a particular plate position via a map that is generated by the system and transmitted to a central control unit.

Other components, such as the sample racks, also may be barcoded to track their use or movement, or to identify their contents.

Any suitable barcode readers may be used to scan the various barcodes, and such readers may be located at any suitable location. For example, a barcode reader may be placed in a fixed position, with barcodes being read as they are moved past the reader. In other embodiments, a barcode reader may be attached to a robotic arm, which may be moved to permit scanning of samples from different positions and angles. In other embodiments, a barcode reader may be attached to a robotic arm or other mechanism that transports the object, in which case the barcode reader may scan the object as it is being transported. Such devices may hold the object on a rotating or moving platform that repositions the object to bring the barcode within sight of the reader. For example, a rotating head that holds an object may facilitate barcode reading with a fixed barcode reader or with a barcode reader attached to a robotic arm. Other exemplary embodiments employ mirrors and/or other optics to permit scanning of barcodes in different locations, on objects situated at different angles, on objects located at different distances from a reader, and so on.

The construction and operation of suitable barcode readers are well known in the art, and need not be explained in detail here. It will be understood that any linear, omni-directional, 2-dimensional, holographic, pattern recognition, or other scanning system and format may be used. Furthermore, as used herein, the term "barcode" also encompasses not only any and all optical identification systems, but also non-optical systems, such as radio-frequency identification (RFID) systems. RFID systems may include an RFID tag and a reader, which may be employed in similar ways to optical barcodes, except that a line of sight may not be required. Methods known in the art may be used to avoid the ambiguities potentially created by the omnidirectional nature of the RFID signal, such as use of directional antennae for transmission or receipt of signals; use of systems effective only at short-range (permitting disambiguation through signal attenuation or through decreasing the number of tags within range of the receiver); use of RFID tags for objects of a type that are unique within a system; or use of RFID tags together with other spatial information (e.g., an RFID tag associated with an entire sample rack, together with known information about which sample is in which position in the rack).

Clinical Example 1

An exemplary embodiment was operated to process liquid based cytology specimens using Qiagen's Next Generation Hybrid Capture® High Risk assay. The system was adapted to accommodate specimens in PreservCyt® (PC) medium in the existing Hybrid Capture 2 (HC2) assay, which requires sample volumes of 4 mL. The pre-analytical system was developed to produce up to ten 96-well plates of extracted DNA in less than 5 to 6 hours for subsequent analysis in the Next Generation Hybrid Capture Assay® (NGA) (see U.S. Provisional Application 61/108,687 filed Oct. 27, 2008). From system start-up, the first fully processed plate was produced in 59 minutes with subsequent plates available every 24 min. The objective for this study was to compare manual nucleic acid extraction method from 1 ml of PC samples with the high-throughput automation method for recovery, carryover, throughput and reproducibility of HPV DNA processed.

In this example DNA-extraction chemistry was used in an automated version of the manual process of sample conversion (extracting nucleic acid from a cytology sample). HC2-positive PC specimens were spiked into pooled HC2-negative specimens and replicate aliquots were processed in the sample prep processing instrument or manually. Recovery was determined by comparative HC2 signal output from each method. Carryover was assessed by measuring the RLU/CO of negative specimens that were processed just before and just after a high positive specimen. Intra-plate reproducibility was measured with plasmid introduced into the sample preparation process and compared to plasmid tested directly in the NGA. Inter-plate reproducibility was measured by comparing known copies of HPV plasmid DNA processed from 10 plates.

In two separate runs of a PC positive clinical pool, (n=32 replicates each run) the percent signal recoveries from the automated method were 99% (9% CV) and 93% (6% CV). Results from negative pools run through the automated system were also comparable to those manual method results: the RLU/CO of the manually processed clinical pools (n=8) compared to automated-processed pools (n=40) from three separate runs were: 0.27 to 0.26 (11% CV); 0.28 to 0.32 (20%

CV); and 0.31 to 0.27 (15% CV). In carryover measurements, the average RLU/CO difference between negative specimens that were processed before (n=40, 16, 12) and after (n=40, 40, 52) a high positive were minimal: 0.26 to 0.32 (20% CV); 0.32 to 0.30 (20% CV); and 0.32 to 0.37 (32% CV). In another target carry-over study, $10^8$ copies of HPB16 DNA were added into a negative sample panel, and it was shown that neighboring samples did not give a positive signal. Intra-plate and inter-plate reproducibility was very good with low CV. Processing of 80 replicates of either negative or positive (HPV 16 DNA) samples showed very low sample-to-sample variability (CV 12% for negative samples and 5% for positive samples). High reliability and low variability of the magnetic beads was demonstrated by employing several lots of magnetic beads and observing comparable signal levels (RLU/CO values) between lots. Ten plates of individual clinical PC specimens were successfully run through the automated system in a continuous fashion in just over 4.5 hours.

This integrated system in this embodiment is believed to be particularly advantageous due to the low throughput of manual sample conversion protocol.

Clinical Example 2

A fully automated Next Generation Hybrid Capture® HPV DNA assay was performed on an automated analytical system. It was found that the analytical sensitivity for the automated system was 1875 copies (95% CI 1615-2290) of HPV 16 plasmid, as compared to 1950 copies (95% CI 1650-2800) of HPV 16 plasmid in the manual assay. Assay specificity was evaluated with 22 HPV LR types in the Next Generation Hybrid Capture Assay® (NGA) (see co-pending provisional application 61/108,687 filed Oct. 27, 2008, which is incorporated by reference herein) assay and compared to the current HC2 HPV DNA Test. All 22 HPV LR types were tested at a high concentration of 2.0 ng/mL. Results of the analytical testing show that the number of HPV low risk types that cross-hybridize with the NextGen assay is significantly reduced as compared to HC2 assay. Clinical specimens with 30% prevalence rates were used to evaluate the performance between the automated system and manual assays. The total, positive and negative agreements were 96% (95% CI 89-98%), 85% (95% CI 64-95%), and 99% (95% CI 7498%), respectively. The Kappa value was 0.87 for this study. The assay reproducibility on the automated system was improved over the manual assay using HPV 16 plasmids. The fully automated assay had consistent performance from plate to plate and day to day. No indication of target carryover was found when samples containing up to $7.5 \times 10^5$ copies/ml of HPV DNA type 16 were processed on the automatic system.

Overall the analytical and clinical data presented is believed to show that the fully automated Next Generation Hybrid Capture® HPV DNA assay on an automated analytical system can significantly improve assay specificity and assay reproducibility without compromising sensitivity of detection of HR virus. The automated system provides also full automation of the next-generation hybrid capture HPV DNA assay with a high throughput.

Clinical Example 3

In this study evaluated a novel extraction protocol that is compatible with various collection media and amenable to high throughput automation. A standard and reproducible HPV DNA test method that uses residual samples from Sure-Path media has not been previously reported. Most methods use cumbersome procedures and longer lysis incubation time, which is not suitable for high volume lab workflow. The desired extraction chemistry preferably takes no more than about 60 minutes for processing 96 samples and may be compatible with the ultra-high throughput next generation Hybrid Capture® system QIAensemble SP from Qiagen. A universal extraction chemistry protocol was developed for use with both PerservCyt and SurePath liquid based media.

Figure 22:
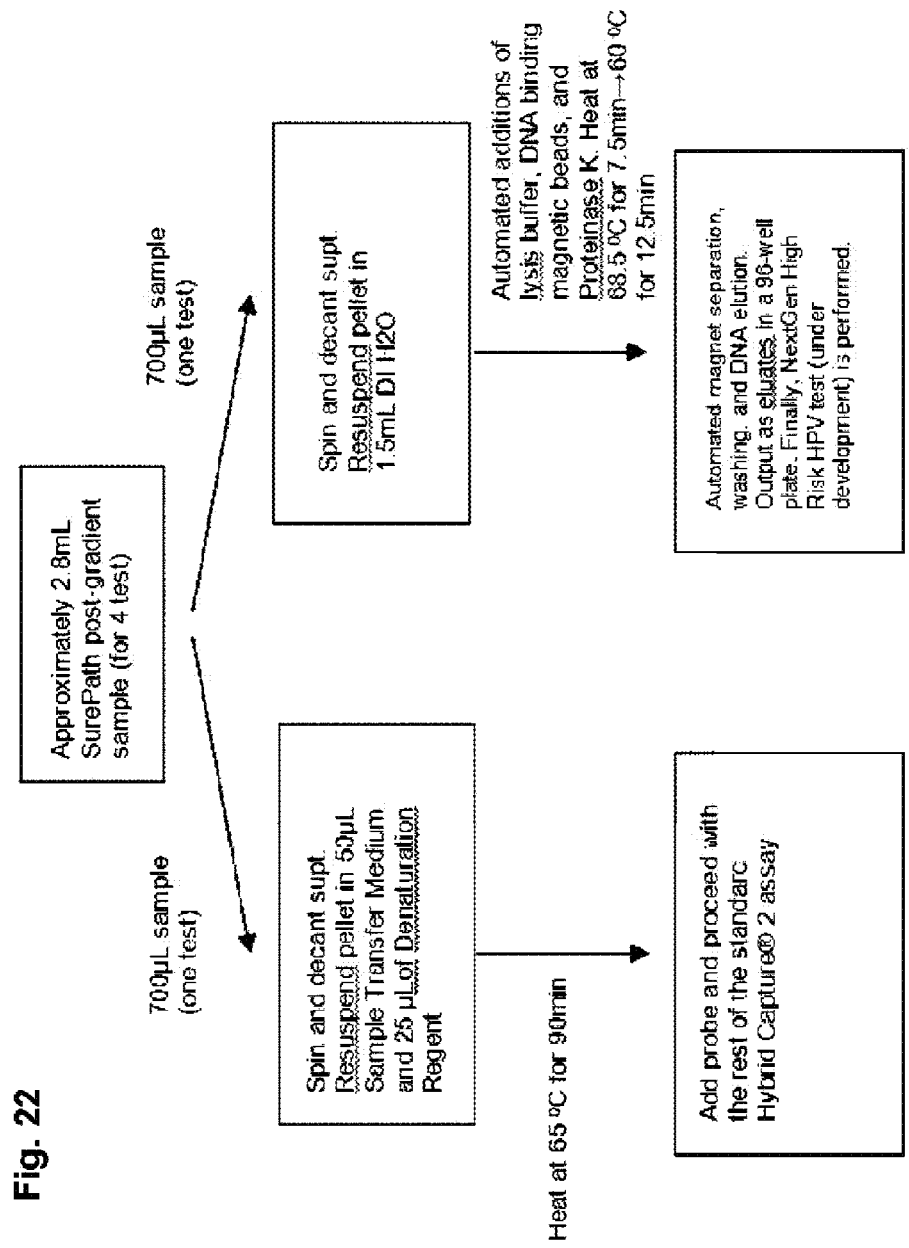
FIG. 22 is a flow diagram illustrating an exemplary assay protocol.

In this study, the novel sample processing chemistry was evaluated against the industry standard: Digene Hybrid Capture® 2 High-Risk HPV DNA Test® method. HPV16 positive SiHa cells (20,000 cells) were spiked into 4 mL of negative PC clinical specimen pool processed using a standard HC2 manual conversion method. The same amount of SiHa cells were spiked into a 1.5 mL PC pool and processed by the new extraction protocol. The same volumes of Surepath® HPV positive and negative clinical pools by HC2 were tested by both sample processing methods. Assay protocols are illustrated in FIG. 22. The centrifugation step may be performed as part of an automated system or manually. DNA eluates generated by both methods then were then re-tested side-by-side by the HC2 method. Recovery was determined by comparative HC2 signal output from each method. The new chemistry protocol was integrated with prototype instrumented and performance was evaluated with the HC2 method by testing individual clinical specimens.

Figure 23:
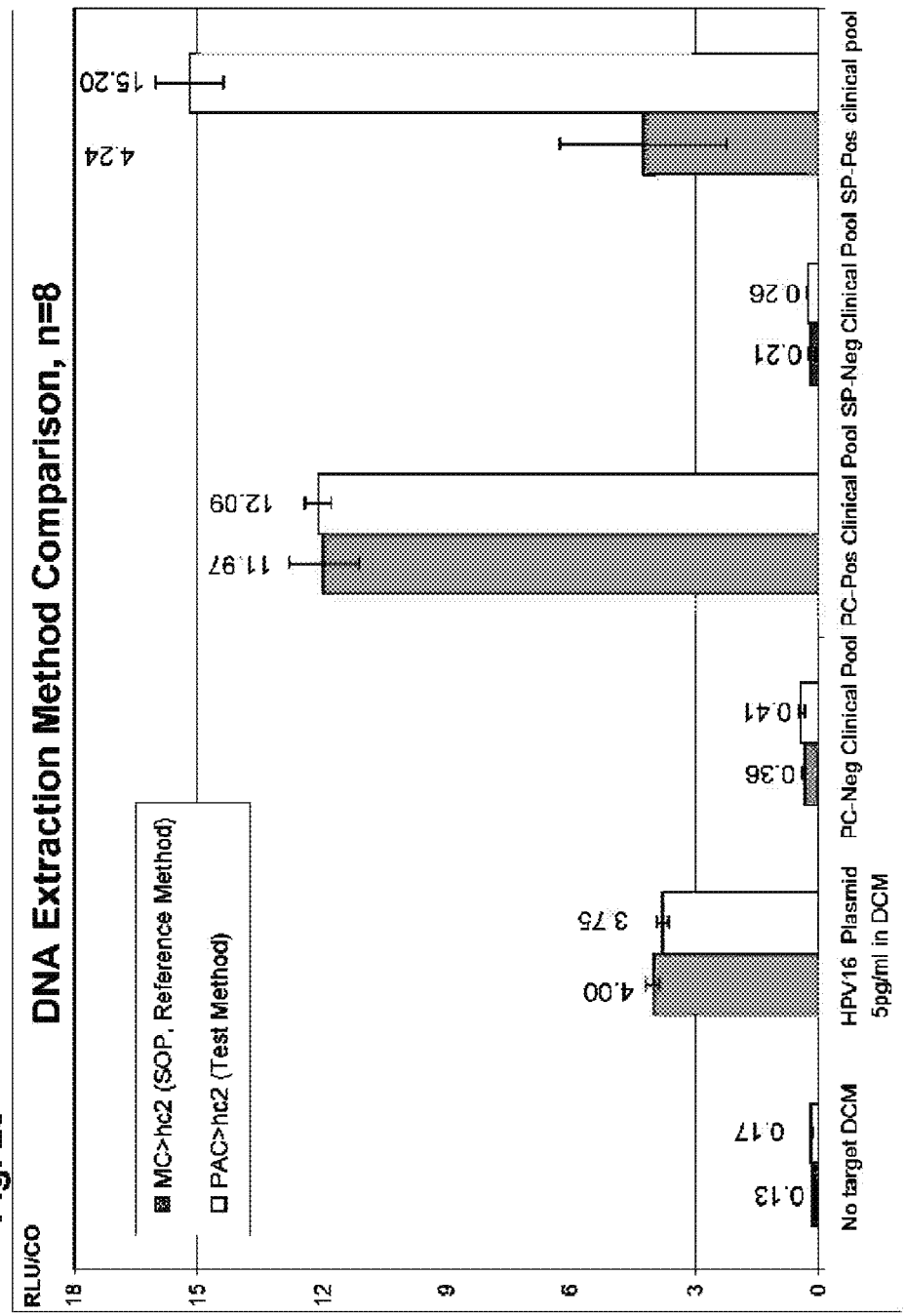

Referring now to FIGS. 23-25, the results with PC positive and negative pool show similar performance by both sample processing protocols with no increase in the background signal (left column in each group is the reference method; right column in each group is the test method). In SurePath® samples, the new extraction method resulted in a 3.5 fold increase in signal relative to the standard HC2 method ("SP-Pos clinical pool"), relatively low background with negative samples ("SP-Neg clinical pool") and good reproducibility. The new method showed 93% DNA recovery when compared to direct DNA input in HC2. The individual Surepath® clinical specimens (n=160) processed by NextGen automation and compared with HC2 manual process showed a greater than 90% assay agreement. This study is believed to established a novel universal protocol and automation solution for HPV DNA test with residual liquid-based cytology (LBC) specimens and demonstrates high throughput compatibility by processing 96 samples in 60 minutes. These results additionally demonstrate the flexibility of the automated systems provided herein.

While the invention has been described by way of examples and preferred embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

What is claimed is:

1. A continuous-loading sample processing system comprising:
    a sample input adapted to receive at least one sample container rack manually provided by a user;
    a consumable input adapted to receive one or more unused consumable supplies manually provided by a user;
    a waste output adapted to receive used consumable supplies;

an automated processing center comprising:
- a decapper adapted to remove a lid from at least one sample container provided in the at least one sample container rack, the at least one sample container having contents comprising a specimen,
- at least one shaker adapted to shake the at least one sample container and homogenize the contents,
- a pipettor adapted to remove the specimen from the at least one sample container and transfer the specimen to at least one output vessel, and
- a capper adapted to replace the lid on the at least one sample container; and a sample output adapted to receive the at least one output vessel and present the at least one output vessel to a user for manual removal.

2. The system of claim 1, wherein the decapper and the capper comprise at least one combination decapper/capper unit adapted to remove the lid from the sample container and replace the lid on the sample container.

3. The system of claim 2, wherein the decapper and the capper comprise two combination decapper/capper units.

4. The system of claim 3, wherein the sample output comprises at least one output rack adapted to receive a plurality of output vessels.

5. The system of claim 2, wherein the at least one combination decapper/capper comprises:
- at least one bottle grip adapted to hold a bottle portion of the at least one sample container; and
- at least one cap grip adapted to hold the lid;
- wherein the bottle grip and the cap grip are movable relative to one another to remove the lid from the bottle portion.

6. The system of claim 5, wherein the at least one bottle grip comprises a bellows grip having a flexible bellows with a variable-size bore adapted to receive the bottle portion along an axis of the variable-size bore, and one or more ribs mounted on the flexible bellows within and aligned with the axis of the variable-size bore.

7. The system of claim 5, wherein the at least one bottle grip is mounted on a platform, the platform being adapted to selectively move to a first location accessible to the at least one cap grip, and a second location accessible to the pipettor, and further being adapted to tilt the bottle portion relative to a vertical axis at the second location.

8. The system of claim 1, wherein the automated processing center further comprises a transfer arm adapted to remove the at least one sample container from the sample container rack and place the at least one sample container in the decapper.

9. The system of claim 1, wherein the automated processing center further comprises:
- a transfer arm system adapted to:
  - remove the at least one sample container from the at least one sample container rack and place the at least one sample container in the at least one shaker,
  - remove the at least one sample container from the at least one shaker and place the at least one sample container in the decapper, and
  - remove the at least one sample container from the capper and place the at least one sample container in the at least one sample container rack.

10. The system of claim 9, wherein the automated processing center further comprises a barcode reader adapted to read any readable barcode on the at least one sample container.

11. The system of claim 1, wherein the at least one sample container rack comprises one or more sample holders adapted to hold at least one first sample container having a first size, and at least one second sample container having a second size that is different from the first size.

12. The system of claim 1, further comprising a reagent input adapted to receive one or more unused reagents manually provided by a user.

13. The system of claim 12, wherein the automated processing center further comprises at least one reagent dispenser adapted to dispense at least one of the one or more unused reagents into the at least one sample container.

14. A sample processing system comprising:
- a sample input adapted to simultaneously receive a plurality of sample containers;
- a consumable input adapted to receive one or more unused consumable supplies;
- a waste output adapted to receive used consumable supplies;
- an automated processing center comprising:
  - a decapper adapted to remove a lid from at least one sample container, the at least one sample container having contents comprising a specimen,
  - at least one shaker adapted to shake the at least one sample container and homogenize the contents,
  - a pipettor adapted to remove the specimen from the at least one sample container and transfer the specimen to an output vessel, and
  - a capper adapted to replace the lid on the at least one sample container;
- a sample output adapted to receive the output vessel; and
- a user interface adapted to receive an input from the user to indicate the identity of the at least one sample container, and control at least one operation based on a physical property of the at least one sample container.

15. The system of claim 14, wherein the plurality of sample containers comprises at least one first sample container having a first size, and at least one second sample container having a second size that is different from the first size.

16. The system of claim 14, wherein the sample input is adapted to simultaneously receive a plurality of sample containers in a sample container rack.

17. The system of claim 14, wherein the sample container rack comprises one or more sample holders adapted to hold at least one first sample container having a first size, and at least one second sample container having a second size that is different from the first size.

18. The system of claim 14, further comprising a reagent input adapted to receive one or more unused reagents.

19. The system of claim 18, wherein the automated processing center further comprises at least one reagent dispenser adapted to dispense at least one of the one or more unused reagents into the at least one sample container.

20. A hybrid manual-automated method for processing samples, the method comprising:
- manually providing a plurality of sample containers in a sample input, the sample containers having contents comprising a specimen;
- manually providing unused consumable supplies in a consumables input;
- automatically shaking the sample containers to homogenize the contents;
- automatically removing a lid from each sample container using an automated system;
- automatically withdrawing the specimen from each sample container using the automated system;
- automatically transferring the specimen to an output vessel using the automated system;
- automatically replacing the lid on each sample container using the automated system;

automatically conveying the output vessel to an sample output location using the automated system; and manually removing the output vessel from the sample output location.

21. The method of claim 20, further comprising programming the automated system to control at least one operation based on a physical property at least a first sample container.

22. The method of claim 21, wherein programming the automated system comprises manually programming the automated system.

23. The method of claim 20, further comprising programming the automated system to control at least one operation in a first manner based on a physical property at least a first sample container, and in a second manner based on a physical property of at least a second sample container.

24. The method of claim 20, wherein the plurality of sample containers comprise at least one first sample container having a first physical dimension and at least one second sample container having a second physical dimension that is different from the first physical dimension.

25. The method of claim 20, further comprising manually providing one or more unused reagents in a reagent input, and automatically dispensing at least one of the one or more unused reagents into at least one sample container.

* * * * *